United States Patent
Spence et al.

(10) Patent No.: US 10,557,124 B2
(45) Date of Patent: Feb. 11, 2020

(54) COMPOSITIONS AND METHODS FOR OBTAINING STEM CELL DERIVED LUNG TISSUE, AND RELATED USES THEREOF

(71) Applicant: The Regents of the University of Michigan, Ann Arbor, MI (US)

(72) Inventors: Jason Spence, Ann Arbor, MI (US); Briana Dye, Ann Arbor, MI (US)

(73) Assignee: THE REGENTS OF THE UNIVERSITY OF MICHIGAN, Ann Arbor, MI (US)

(*) Notice: Subject to any disclaimer, the term of this patent is extended or adjusted under 35 U.S.C. 154(b) by 219 days.

(21) Appl. No.: 15/134,498

(22) Filed: Apr. 21, 2016

(65) Prior Publication Data

US 2016/0312191 A1   Oct. 27, 2016

Related U.S. Application Data

(60) Provisional application No. 62/151,238, filed on Apr. 22, 2015.

(51) Int. Cl.
   *C12N 5/071*   (2010.01)

(52) U.S. Cl.
   CPC ...... *C12N 5/0688* (2013.01); *C12N 2501/119* (2013.01); *C12N 2501/15* (2013.01); *C12N 2501/155* (2013.01); *C12N 2501/16* (2013.01); *C12N 2501/41* (2013.01); *C12N 2501/415* (2013.01); *C12N 2506/02* (2013.01)

(58) Field of Classification Search
   None
   See application file for complete search history.

(56) References Cited

U.S. PATENT DOCUMENTS

2014/0105870 A1*   4/2014   Niklason .............. C12N 5/0688
                                                   424/93.7

OTHER PUBLICATIONS

Kadzik et al, "Lessons from development for directing lung endoderm differentiation in pluripotent stem cells" Cell tem Cell, 2012, pp. 1-11.*
Kadzik et al., "Directing Lung Endoderm Differentiation in Pluripotent Stem Cells", Cell Stem Cell, 2012, vol. 10, pp. 355-361.*
Dye et al., "In vitro generation of human pluripotent stem cell derived lung organoids", eLife, Mar. 24, 2015, vol. 4, pp. 1-25.*
Ameri et al., "FGF2 specifies hESC-derived definitive endoderm into foregut/midgut cell lineages in a concentration-dependent manner", Stem Cells, epublished Nov. 3, 2009, vol. 28, pp. 45-56.*
Huang et al., "The In vitro generation of lung and airway progenitor cells from human pluripotent stem cells", Nat Protoc, Mar. 2015, 10(3), pp. 413-425.*
Monaghan AP, et al., "Postimplantation expression patterns indicate a role for the mouse forkhead/HNF-3 alpha, beta and gamma genes in determination of the definitive endoderm, chordamesoderm and neuroectoderm." Development. Nov. 1993;119(3):567-78.
Morrisey EE, et al., "Preparing for the first breath: genetic and cellular mechanisms in lung development." Developmental Cell.; Jan. 19, 2010;18(1):8-23.
Morrisey, et al., "GATA6 regulates HNF4 and is required for differentiation of visceral endoderm in the mouse embryo" Genes Dev., 1998, 12,3579-3590.
Motoyama J, et al., "Essential function of Gli2 and Gli3 in the formation of lung, trachea and oesophagus." Nat Genet. Sep. 1998;20(1):54-7.
Mou H, et al., "Generation of multipotent lung and airway progenitors from mouse ESCs and patient-specific cystic fibrosis iPSCs." Cell Stem Cell. Apr. 6, 2012;10(4):385-97.
Nakajima M, et al., "Immunohistochemical and ultrastructural studies of basal cells, Clara cells and bronchiolar cuboidal cells in normal human airways" Pathol. Int. Dec. 1998;48(12):944-53.
Nakano T, et al., "Self-formation of optic cups and storable stratified neural retina from human ESCs." Cell Stem Cell. Jun. 14, 2012;10(6):771-85.
Narumi S, et al., "Functional characterization of four novel PAX8 mutations causing congenital hypothyroidism: new evidence for haploinsufficiency as a disease mechanism." Eur. J. Endocrinol. Nov. 2012;167(5):625-32.
Offield, et al., "PDX-1 is required for pancreatic outgrowth and differentiation of the rostral duodenum." Development (1996) 122,983-995.
Okita et al., "Generation of mouse induced pluripotent stem cells without viral vectors." 2008, Science 322 (5903):949-953.
Okubo T; "Nmyc plays an essential role during lung development as a dosage-sensitive regulator of progenitor cell proliferation and differentiation" Development. Feb. 9, 2005;132(6)1363-74.
Prasov L, et al., "Math5 (Atoh7) gene dosage limits retinal ganglion cell genesis." Neuroreport. Jul. 11, 2012;23 (10):631-4.
Rankin SA, Zorn AM. "Gene Regulatory Networks Governing Lung Specification." J Cell Biochem. Aug. 2014;115 (8):1343-50.
Rawlins EL, et al., "The Id2+ distal tip lung epithelium contains individual multipotent embryonic progenitor cells." Development. Nov. 2009;136(22):3741-5.
Ringner M.; "What is principal component analysis?" Nat Biotechnol. Mar. 2008;26(3):303-4.
Rock JR, et al., "Basal cells as stem cells of the mouse trachea and human airway epithelium." Proceedings of the National Academy of Sciences. Aug. 4, 2009;106(31):12771-5.
Rockich BE, et al., "Sox9 plays multiple roles in the lung epithelium during branching morphogenesis" Proceedings of the National Academy of Sciences. Nov. 4, 2013, E4456-E4464.

(Continued)

*Primary Examiner* — Laura Schuberg
(74) *Attorney, Agent, or Firm* — Casimir Jones, SC; Robert Goetz

(57) ABSTRACT

The invention disclosed herein generally relates to methods and systems for converting stem cells into specific tissue(s) or organ(s) through directed differentiation. In particular, the invention disclosed herein relates to methods and systems for promoting definitive endoderm formation from pluripotent stem cells. The invention disclosed herein further relates to methods and systems for promoting ventral-anterior foregut spheroid tissue formation, 3-dimensional lung tissue formation, and lung organoid tissue formation produced in vitro from the described methods.

4 Claims, 30 Drawing Sheets

Specification includes a Sequence Listing.

(56) References Cited

OTHER PUBLICATIONS

Rossant, et al., "Expression of a retinoic acid response element-hsplacZ transgene defines specific domains of transcriptional activity during mouse embryogenesis." Genes Dev., 1991 5,1333-1344.
Schmitz G, et al., "Structure and function of lamellar bodies, lipid-protein complexes involved in storage and secretion of cellular lipids." J. Lipid Res. Oct. 1991;32(10):1539-70.
Serls AE.; "Different thresholds of fibroblast growth factors pattern the ventral foregut into liver and lung." Development. Dec. 2, 2004;132(1):35-47.
Si-Tayeb K, et al., "Highly efficient generation of human hepatocyte-like cells from induced pluripotent stem cells." Hepatology. Oct. 1, 2010;51(1):297-305.
Spence JR, et al., "Directed differentiation of human pluripotent stem cells into intestinal tissue in vitro." Nature. Feb. 3, 2011;470(7332):105-9.
Stadtfeld et al., "Induced pluripotent stem cells generated without viral integration." 2008, Science 322 :5904945-949.
Stafford and Prince, "Retinoic acid signaling is required for a critical early step in zebrafish pancreatic development." Curr. Biol. Jul. 23, 2002;12(14)1215-20.
Stahlman MT, et al., "Lamellar body formation in normal and surfactant protein B-deficient fetal mice." Lab. Invest. Mar. 2000;80(3):395-403.
Stott SRW, et al., "Foxa1 and Foxa2 Are Required for the Maintenance of Dopaminergic Properties in Ventral Midbrain Neurons at Late Embryonic Stages" Journal of Neuroscience. May 1, 2013;33(18):8022-34.
Suzuki R, et al., "Pvclust: an R package for assessing the uncertainty in hierarchical clustering." Bioinformatics. Jun. 15, 2006;22(12):1540-2.
Takebe T, et al., "Vascularized and functional human liver from an iPSC-derived organ bud transplant." Nature. Jul. 25, 2013;499(7459):481-4.
Thomson et al., "Embryonic stem cell lines derived from human blastocysts." 1998, Science 282 (5391):1145-1147.
Tiso, et al., "BMP signalling regulates anteroposterior endoderm patterning in zebrafish" Mech. Dev., 2002, 118, 29-37.
Treutlein B, et al., "Reconstructing lineage hierarchies of the distal lung epithelium using single-cell RNA-seq." Nature. May 15, 2014;509(7500):371-5.
Vilain C, et al., "Autosomal dominant transmission of congenital thyroid hypoplasia due to loss-of-function mutation of PAX8." J. Clin. Endocrinol. Metab. Jan. 2001;86(1)234-8.
Volckaert T, et al., "Localized Fgf10 expression is not required for lung branching morphogenesis but prevents differentiation of epithelial progenitors" Development Sep. 2013; 140(18):3731-42.
Wan, et al., "Compensatory Roles of Foxa1 and Foxa2 during Lung Morphogenesis" J. Biol. Chem. 2005, 280,13809-13816.
Weaver M, et al., "Bmp4 and Fgf10 play opposing roles during lung bud morphogenesis." Development. 2000; 127 (12):2695-704.
Weaver TE, et al., "Biogenesis of lamellar bodies, lysosome-related organelles involved in storage and secretion of pulmonary surfactant" Seminars in Cell & Developmental Biology. Aug. 2002;13(4):263-70.
Wells and Melton, "Early mouse endoderm is patterned by soluble factors from adjacent germ layers." Development, 2000, 127(8),1563-1572.
Wells JM, et al., "How to make an intestine." Development. Feb. 2014;141(4):752-60. PMCID: PMC3912826.
Wells, et al., "Vertebrate Endoderm Development" Annu. Rev. Cell Dev. Biol., 1999, 15,393-410.
Wickham H.; ggplot2: Elegant Graphics for Data Analysis—Hadley Wickham—Google Books. 2009, Table of Contents Only.
Woltjen et al., "piggyBac transposition reprograms fibroblasts to induced pluripotent stem cells" 2009, Nature 458:766-770.
Wong AP, et al., "Directed differentiation of human pluripotent stem cells into mature airway epithelia expressing functional CFTR protein" Nature Biotechnology, 2012, 30, 876-882.
Xue X, et al., "Endothelial PAS Domain Protein 1 Activates the Inflammatory Response in the Intestinal Epithelium to Promote Colitis in Mice" Gastroenterology. Jul. 13, 2013; 145(4): 831-841.
Yuan B, et al., "Inhibition of distal lung morphogenesis in Nkx2.1(-/-) embryos." Dev. Dyn. Feb. 2000;217(2):180-90.
Zhang et al. "Expression of SHH signaling pathway components in the developing human lung." Histochem. Cell Biol. Oct. 2010;134(4):327-35.
Zhou et al., "Generation of induced pluripotent stem cells using recombinant proteins." 2009, Cell Stem Cell 4 (5):381-384.
Abler LL, et al., "Conditional Gene Inactivation Reveals Roles for Fgf10 and Fgfr2 in Establishing a Normal Pattern of Epithelial Branching in the Mouse Lung" Dev. Dyn. Aug. 2009;238(8):1999-2013.
Agha, et al., "Fgf10-positive cells represent a progenitor cell population during lung development and postnatally" Development. 2014, 141, 296-306.
Andrews et al., "Embryonic stem (ES) cells and embryonal carcinoma (EC) cells: opposite sides of the same coin." 2005, Biochem Soc Trans 33:1526-1530.
Ang SL, et al., "HNF-3 beta is essential for node and notochord formation in mouse development." Cell. Aug. 26, 1994;78(4):561-74.
Bellusci S, et al., "Involvement of Sonic hedgehog (Shh) in mouse embryonic lung growth and morphogenesis." Development. Jan. 1997;124(1):53-63.
Boers JE, et al., "Number and proliferation of basal and parabasal cells in normal human airway epithelium." American Journal of Respiratory and Critical Care Medicine. Jun. 1998;157(6 Pt 1):2000-6.
Booth AJ, et al., "Acellular normal and fibrotic human lung matrices as a culture system for in vitro investigation." American Journal of Respiratory and Critical Care Medicine. Nov. 1, 2012;186(9):866-76.
Bort, et al., "Hex homeobox gene-dependent tissue positioning is required for organogenesis of the ventral pancreas." Development, 2004, 131(4),797-80.
Boucherat O, et al., "Decreased Lung Fibroblast Growth Factor 18 and Elastin in Human Congenital Diaphragmatic Hernia and Animal Models" American Journal of Respiratory and Critical Care Medicine. May 15, 2007;175(10):1066-77.
Carre A, et al., "Five new TTF1/NKX2.1 mutations in brain-lung-thyroid syndrome: rescue by PAX8 synergism in one case." Hum. Mol. Genet. Jun. 15, 2009;18(12):2266-76.
Chambers SM, et al., "Highly efficient neural conversion of human ES and iPS cells by dual inhibition of SMAD signaling." Nat Biotechnol. Mar. 1, 2009;27(3):275-80.
Chang DR, et al., "Evening use of light-emitting eReaders negatively affects sleep, circadian timing, and next-morning alertness" Proceedings of the National Academy of Sciences. Sep. 20, 2013, 1232-1237.
Chen L, et al., "Dynamic Regulation of Platelet-Derived Growth Factor Receptor α Expression in Alveolar Fibroblasts during Realveolarization. American Journal of Respiratory Cell and Molecular Biology." American Journal of Respiratory Cell and Molecular Biology. Oct. 2012;47(4):517-27.
Chen Y-J, et al., "De Novo Formation of Insulin-Producing "Neo-B Cell Islets" from Intestinal Crypts" Cell Rep.; Mar. 4, 2014;:1-13.
D'Amour KA, et al., "Efficient differentiation of human embryonic stem cells to definitive endoderm." Nat Biotechnol. Oct. 28, 2005;23(12):1534-41.
D'Amour KA, et al., "Production of pancreatic hormone-expressing endocrine cells from human embryonic stem cells." Nat Biotechnol. Nov. 2006;24(11):1392-401.
Delaforest A, et al., "HNF4A is essential for specification of hepatic progenitors from human pluripotent stem cells." Development. Oct. 2011;138(19):4143-53.
Desai TJ, et al., "Reconstructing lineage hierarchies of distal lung epithelium using single-cell RNA-seq" Nature. Feb. 5, 2014; Treutlein B, et al., Nature. May 15, 2014;509(7500):371-5.
Domyan ET, et al., "Signaling through BMP receptors promotes respiratory identity in the foregut via repression of Sox2" Development. Feb. 8, 2011;138(5):971-81.

(56) References Cited

OTHER PUBLICATIONS

Eisen, et al., "Cluster analysis and display of genome-wide expression patterns" PNAS Dec. 8, 1998 vol. 95 No. 25 14863-14868.
Evans and Kaufman, "Establishment in culture of pluripotential cells from mouse embryos." 1981, Nature 292 (5819): 154-156.
Evans MJ, et al., "Cellular and molecular characteristics of basal cells in airway epithelium." Exp. Lung Res. Jul. 2001;27(5):401-15.
Firth AL, et al., "Generation of multiciliated cells in functional airway epithelia from human induced pluripotent stem cells" Proceedings of the National Academy of Sciences. Apr. 29, 2014;111(17):E1723-30.
Ghaedi M, et al., "Human iPS cell-derived alveolar epithelium repopulates lung extracellular matrix." J. Clin. Invest. Nov. 1, 2013;123(11):4950-62.
Green MD, et al., "Generation of anterior foregut endoderm from human embryonic and induced pluripotent stem cells" Nat Biotechnol. Nature Publishing Group; Feb. 27, 2011:1-7.
Hebrok M, et al., "Notochord repression of endodermal Sonic hedgehog permits pancreas development." Genes & Development. Jun. 1, 1998;12(11):1705-13.
Hinz B, et al., "The myofibroblast: one function, multiple origins." The American Journal of Pathology. Jun. 2007;170 (6):1807-16.
Huang SXL, et al., "Efficient generation of lung and airway epithelial cells from human pluripotent stem cells" Nat Biotechnol; 2014; 32(1), 84-94.
Jiang D., et al., "Cluster Analysis for Gene Expression Data: A Survey" IEEE Trans. Knowl. Data Eng. Nov. 2004;16 (11):1370-86.
Kaji et al., 2009, "Virus-free induction of pluripotency and subsequent excision of reprogramming factors." Nature 458:771-775.
Kimura S, et al., "The T/ebp null mouse: thyroid-specific enhancer-binding protein is essential for the organogenesis of the thyroid, lung, ventral forebrain, and pituitary" Genes Dev. Jan. 1;10(1):60-927, 1996, pp. 60-69.
Klimanskaya et al., "Human embryonic stem cells derived without feeder cells" 2005, Lancet 365 (9471): 1636-1641.
Ko L., et al., "Alpha smooth muscle actin expression in developing and adult human lung." Differentiation. Aug. 1990;44(2):143-9.
Kroon E, et al. "Pancreatic endoderm derived from human embryonic stem cells generates glucose-responsive insulin-secreting cells in vivo." Nat Biotechnol. Feb. 20, 2008;26(4):443-52.
Kumar and Melton, "Pancreas specification: a budding question" Curr. Opin. Genet. Dev., 2003, 13,401-407.
Kuo, et al., "GATA4 transcription factor is required for ventral morphogenesis and heart tube formation." Genes Dev. 1997, 11,1048-1060.
Kusakabe T, et al., "Thyroid-specific enhancer-binding protein/NKX2.1 is required for the maintenance of ordered architecture and function of the differentiated thyroid." Mol. Endocrinol. 2006 g;20(8):1796-809.
Lancaster MA, et al., "Cerebral organoids model human brain development and microcephaly." Nature. Sep. 2013;501(7467):373-9.
Li Y, et al., "Sonic hedgehog signaling regulates Gli3 processing, mesenchymal proliferation, and differentiation during mouse lung organogenesis" Developmental Biology. Jun. 1, 2004;270(1):214-31.
Loh KM, et al., "Efficient endoderm induction from human pluripotent stem cells by logically directing signals controlling lineage bifurcations." Cell Stem Cell. Feb. 6, 2014;14(2):237-52.
Longmire TA, et al., "Efficient derivation of purified lung and thyroid progenitors from embryonic stem cells." Cell Stem Cell. Apr. 6, 2012;10(4):398-411.
Low RB, et al., "Lung smooth muscle differentiation." Int. J. Biochem. Cell Biol. Aug. 1998;30(8):869-83.
Mansouri A, et al., "Follicular cells of the thyroid gland require Pax8 gene function." Nat Genet. May 1998;19(1):87-90.
Martin "Teratocarcinomas and mammalian embryogenesis." 1980, Science 209 (4458):768-776.
Martinez Barbera, et al., "The homeobox gene Hex is required in definitive endodermal tissues for normal forebrain, liver and thyroid formation." Development, 2000, 127,2433-2445.
McCracken KW, et al., "Generating human intestinal tissue from pluripotent stem cells in vitro. Nature Protocols." Nature Protocols; Nov. 10, 2011;6(12)1920-8.
McCracken KW, et al., "Modelling human development and disease in pluripotent stem-cell-derived gastric organoids" Nature; Oct. 29, 2014;:1-19; 7.
Meyer JS, et al., "Optic vesicle-like structures derived from human pluripotent stem cells facilitate a customized approach to retinal disease treatment." Stem Cells. Aug. 2011;29(8):1206-18.
Min H, et al., "Fgf-10 is required for both limb and lung development and exhibits striking functional similarity to *Drosophila branchless.*" Genes & Development. Oct. 15, 1998;12(20):3156-61.

* cited by examiner

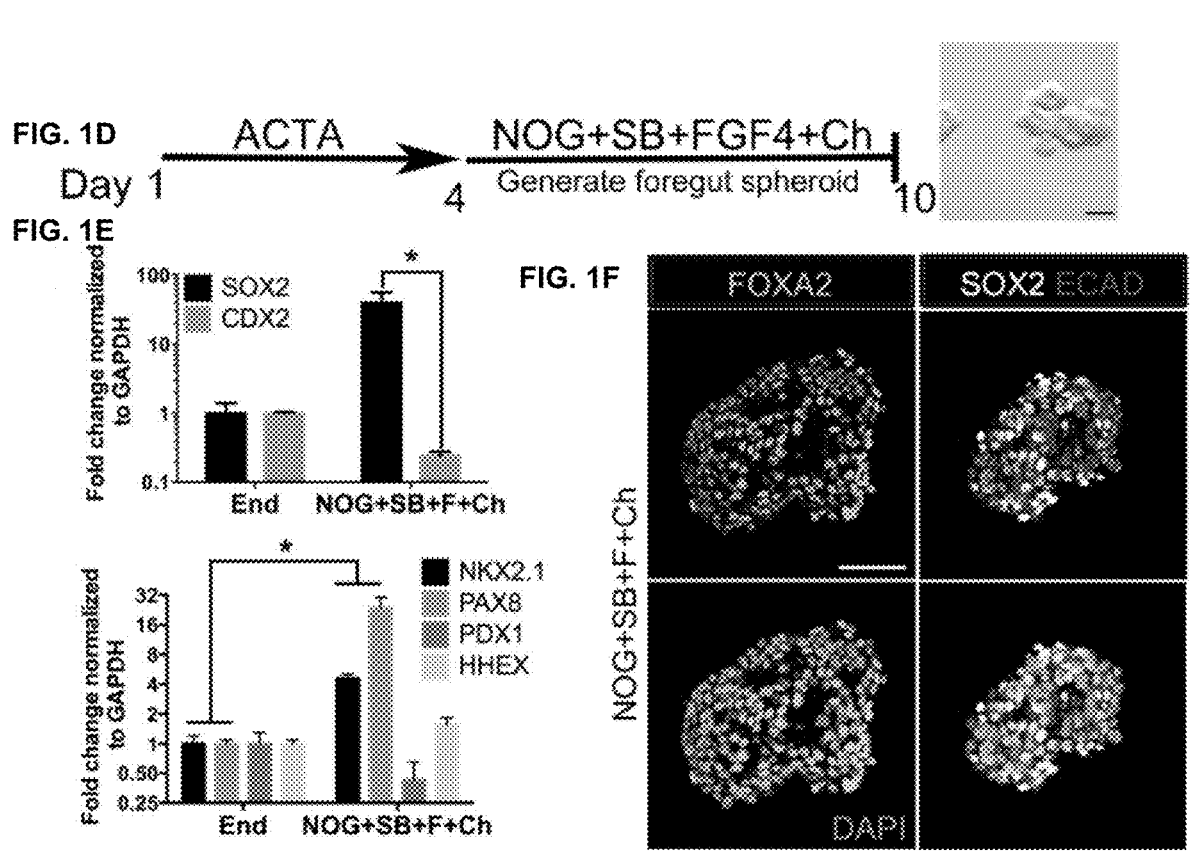

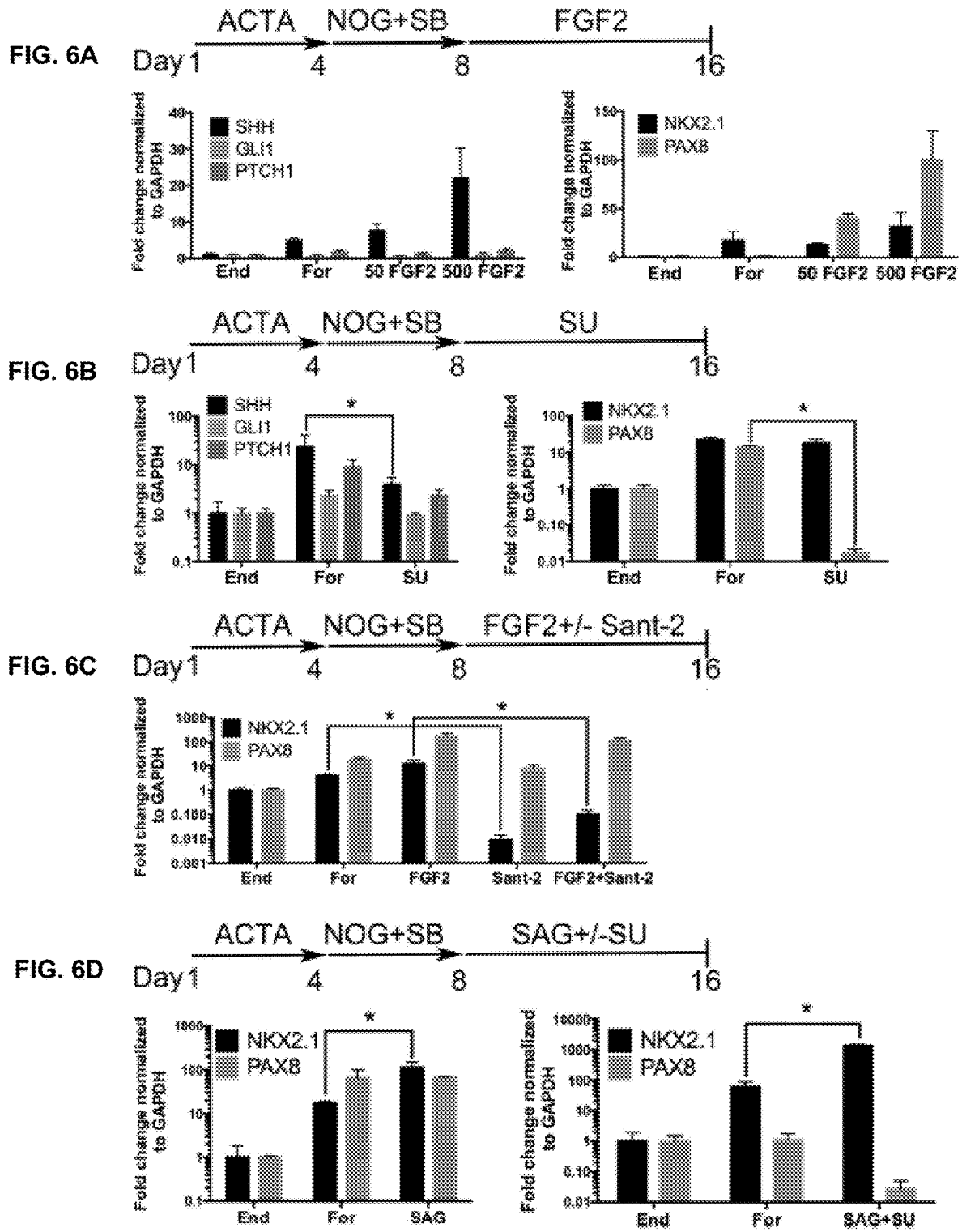

FIG. 10A
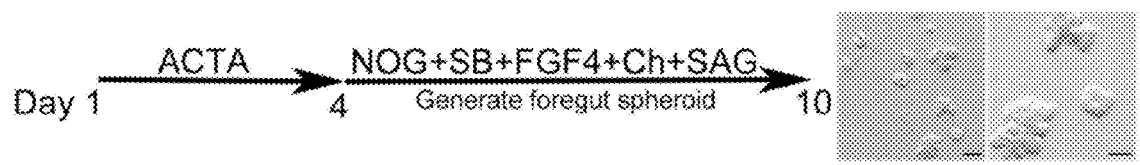
FIG. 10B
FIG. 10C
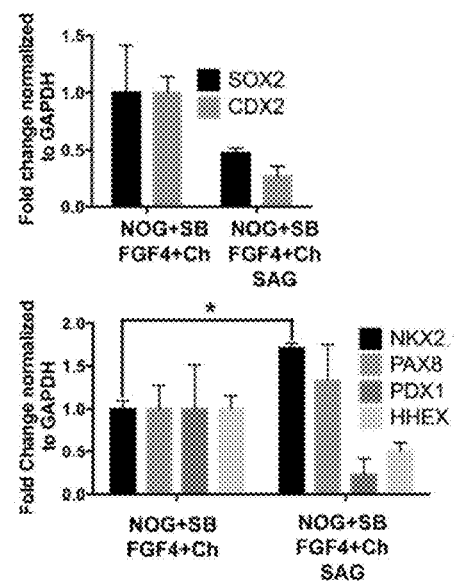
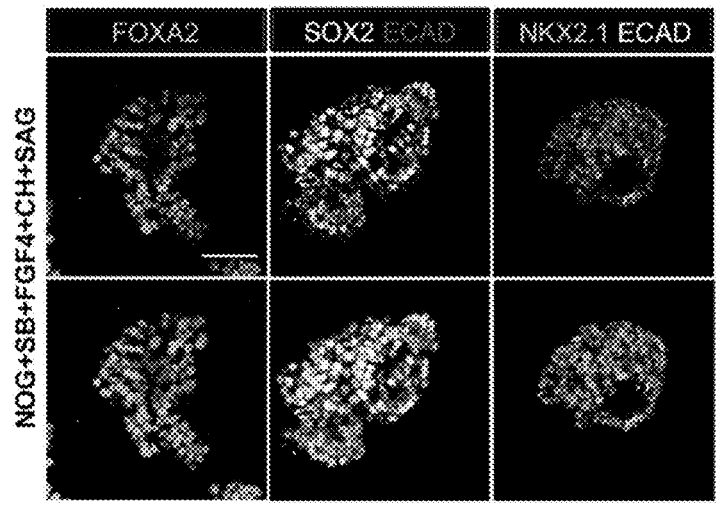

FIG. 18A
FIG 18B
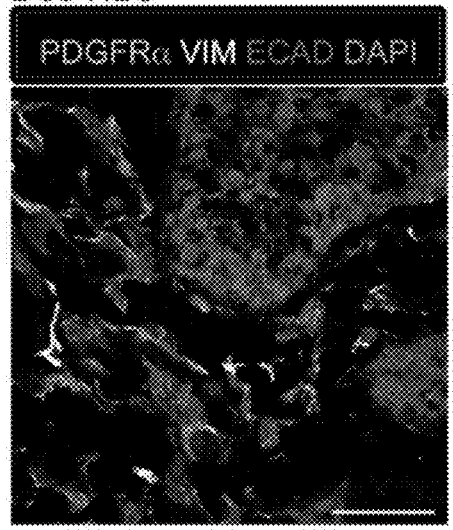
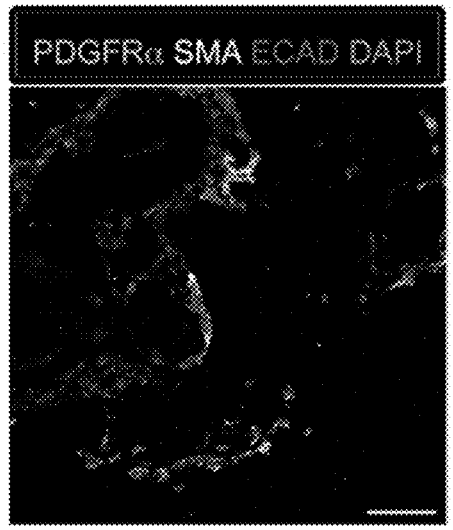
FIG. 18C
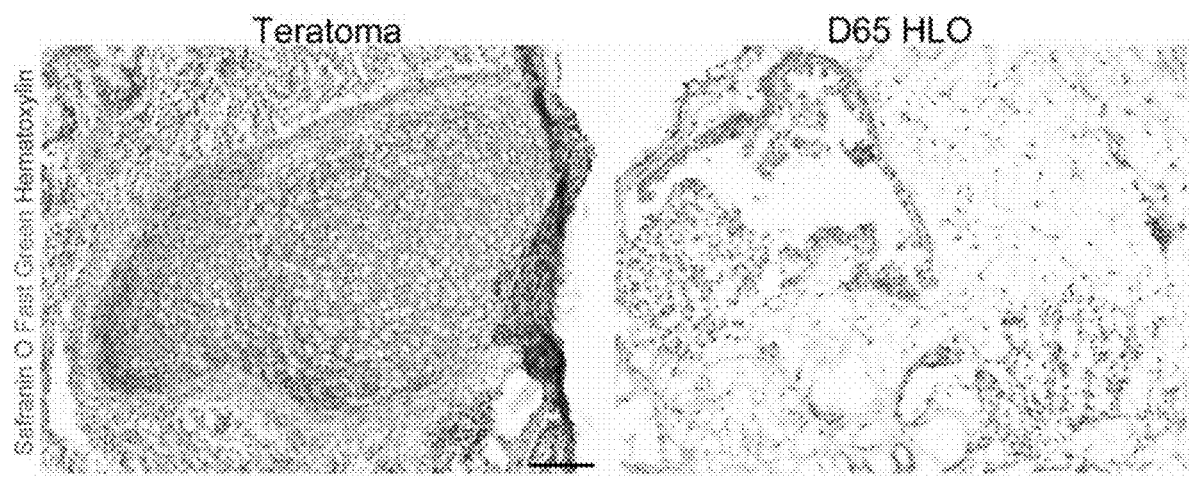

FIG. 21A
| Structural composition of HLOs | | |
|---|---|---|
|  | N | % |
| Proximal airway-like epithelium | 39/48 | 81% |
| Distal airway-like epithelium | 48/48 | 100% |
FIG. 21B
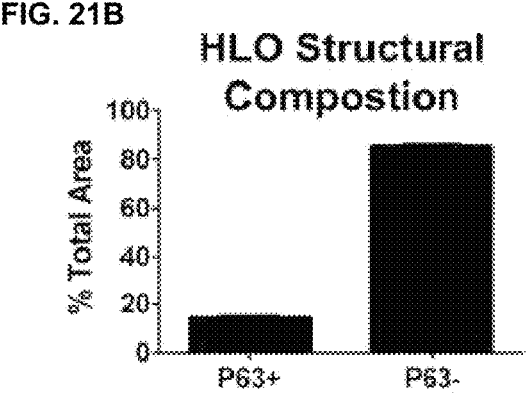
FIG. 21C
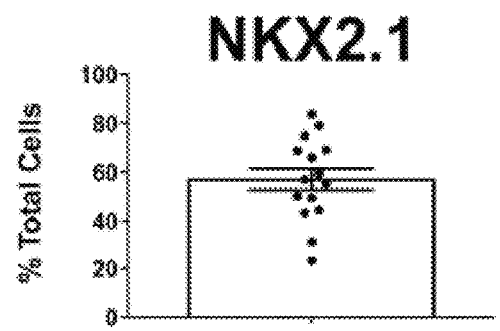
FIG. 21D
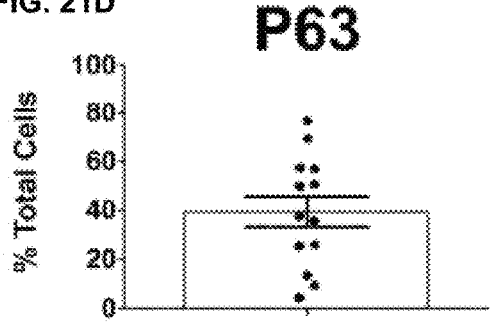
FIG. 21E
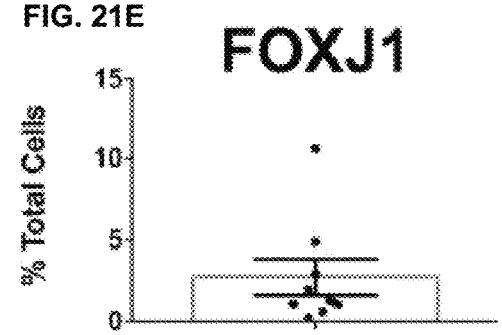
FIG. 21F
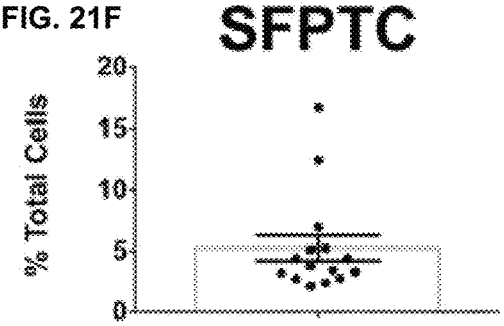
FIG. 21G
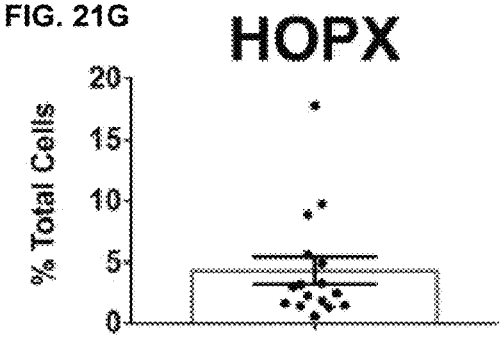

FIG. 22

| Table 1 | | | | |
|---|---|---|---|---|
| Sample Label | Description | Source | Donor ID | Accession # |
| Lung_A_1 | Adult Lung 3e | EMBL-EBI ArrayExpress | V80 | E-MTAB-1733 |
| Lung_A_2 | Adult Lung 3f | EMBL-EBI ArrayExpress | V81 | E-MTAB-1733 |
| Lung_A_3 | Adult Lung 4a | EMBL-EBI ArrayExpress | V130 | E-MTAB-1733 |
| Lung_A_4 | Adult Lung 4b | EMBL-EBI ArrayExpress | V131 | E-MTAB-1733 |
| Lung_A_5 | Adult Lung 4d | EMBL-EBI ArrayExpress | V133 | E-MTAB-1733 |
| Lung_A_6 | Fetal day 105, lung | GEO Datasets | H-24005 | GSM1101693 |
| Lung_F_2 | Fetal day 105, lung | GEO Datasets | H-24111 | GSM1101708 |
| Lung_F_3 | Fetal day 108, lung | GEO Datasets | H-23887 | GSM1101684 |
| Lung_F_4 | Fetal day 91, lung | GEO Datasets | H-23914 | GSM1101685 |
| Lung_F_5 | Fetal day 96, lung | GEO Datasets | H-24089 | GSM1101699 |
| Lung_F_6 | Fetal day 98, lung | GEO Datasets | H-23964 | GSM1101687 |

FIG. 24

| TABLE 2 | | | | |
|---|---|---|---|---|
| Primary Antibody | Source | Catalog # | Dilution | Clone |
| Chicken anti-GFP | Abcam | Ab13970 | 1:500 | polyclonal |
| Goat anti-β-Catenin (BCAT) | Santa Cruz Biotechnology | sc-1496 | 1:200 | C-18 |
| Goat anti-CC10 | Santa Cruz Biotechnology | sc-9770 | 1:200 | C-20 |
| Goat anti-E-Cadherin (ECAD) | R&D Systems | AF748 | 1:100 | N-19 |
| Goat anti-FOXA2 | Santa Cruz Biotechnology | sc-6554 | 1:100 | M-20 |
| Goat anti-SOX2 | Santa Cruz Biotechnology | sc-17320 | 1:100 | Y-17 |
| Goat anti-SOX9 | R&D Systems | AF3075 | 1:500 | polyclonal |
| Goat anti-SOX17 | R&D Systems | AF1924 | 1:500 | polyclonal |
| Goat anti-VIMENTIN (VIM) | Santa Cruz Biotechnology | sc-7558 | 1:100 | S-20 |
| Mouse anti-Acetylated Tubulin (ACTTUB) | Sigma-Aldrich | T7451 | 1:1000 | 6-11B-1 |
| Mouse anti-E-Cadherin (ECAD) | BD Transduction Laboratories | 610181 | 1:500 | 36/E-Cadherin |
| Mouse anti-FOXJ1 | eBioscience | 14-9965-82 | 1:500 | 2A5 |
| Rabbit anti-FOXA2 | Seven Hills Bioreagents | WRAB-FOXA2 | 1:1000 | aa7-58 |
| Rabbit anti-NKX2.1 | Abcam | ab76013 | 1:200 | EP1584Y |
| Rabbit anti-P63 | Santa Cruz Biotechnology | sc-8344 | 1:200 | H-129 |
| Rabbit anti-PAX8 | Proteintech Group | 10336-1-AP | 1:500 | Ag0306 |
| Rabbit anti-PDPN | Santa Cruz Biotechnology | sc-134482 | 1:200 | FL-162 |
| Rabbit anti-N-Terminal Pro SP-C (SFTPC) | Seven Hills Bioreagents | WRAB-9337 | 1:200 | aa1-35 |
| Rabbit anti-SOX2 | Seven Hills Bioreagents | WRAB-SOX2 | 1:500 | polyclonal |
| Cy3- Mouse anti Actin-alpha smooth muscle (SMA)* | Sigma | C6198 | 1:400 | MonoClonal |
| Rabbit anti-Surfactant Protein B (SFTPB) | Santa Cruz Biotechnology | sc-13979 | 1:200 | H-300 |
| Secondary Antibody | Source | Catalog # | Dilution | |
| Donkey anti-goat 488 | Jackson Immuno | 705-545-147 | 1:500 | |
| Donkey anti-goat 647 | Jackson Immuno | 705-605-147 | 1:500 | |
| Donkey anti-goat Cy3 | Jackson Immuno | 705-165-147 | 1:500 | |
| Donkey anti-mouse 488 | Jackson Immuno | 715-545-150 | 1:500 | |
| Donkey anti-mouse 647 | Jackson Immuno | 415-605-350 | 1:500 | |
| Donkey anti-mouse Cy3 | Jackson Immuno | 715-165-150 | 1:500 | |
| Donkey anti-rabbit 488 | Jackson Immuno | 711-545-152 | 1:500 | |
| Donkey anti-rabbit 647 | Jackson Immuno | 711-605-152 | 1:500 | |
| Donkey anti-rabbit Cy3 | Jackson Immuno | 711-165-152 | 1:500 | |
| Donkey anti-goat 488 | Jackson Immuno | 705-545-147 | 1:500 | |
| Donkey anti-goat 647 | Jackson Immuno | 705-605-147 | 1:500 | |
| Donkey anti-goat Cy3 | Jackson Immuno | 705-165-147 | 1:500 | |
| Donkey anti-mouse 488 | Jackson Immuno | 715-545-150 | 1:500 | |
| Donkey anti-mouse 647 | Jackson Immuno | 415-605-350 | 1:500 | |
| Donkey anti-mouse Cy3 | Jackson Immuno | 715-165-150 | 1:500 | |
| Donkey anti-rabbit 488 | Jackson Immuno | 711-545-152 | 1:500 | |
| Donkey anti-rabbit 647 | Jackson Immuno | 711-605-152 | 1:500 | |
| Donkey anti-rabbit Cy3 | Jackson Immuno | 711-165-152 | 1:500 | |

*Secondary antibody conjugated to the primary antibody

FIG. 25

| TABLE 3 | | | | |
|---|---|---|---|---|
| | | SEQ ID NO.: | | SEQ ID NO.: |
| Primer Name | Forward Sequence | | Reverse Sequence | |
| CDX2 | GGGCTCTCTGAGAGGCAGGT | 1 | GGTGACGGTGGGGTTTAGCA | 2 |
| ECADHERIN | TTGACGCCGAGAGCTACAC | 3 | GACCGGTGCAATCTTCAAA | 4 |
| FOXA2 | CGACTGGAGCAGCTACTATGC | 5 | TACGTGTTCATGCCGTTCAT | 6 |
| FOXJ1 | CAACTTCTGCTACTTCCGCC | 7 | CGAGGCACTTTGATGAAGC | 8 |
| HHEX | CCTCTGTACCCCTTCCCG | 9 | GGGGCTCCAGAGTAGAGGTT | 10 |
| HOPX | GCCTTTCCGAGGAGGAGAC | 11 | TCTGTGACGGATCTGCACTC | 12 |
| ID2 | GACAGCAAAGCACTGTGTGG | 13 | TCAGCACTTAAAAGATTCCGTG | 14 |
| MUC5AC* | GCACCAACGACAGGAAGGATGAG | 15 | CACGTTCCAGAGCCGGACAT | 16 |
| NKX2.1 | CTCATGTTCATGCCGCTC | 17 | GACACCATGAGGAACAGCG | 18 |
| NMYC | CACAGTGACCACGTCGATTT | 19 | CACAAGGCCCTCAGTACCTC | 20 |
| P63 | CCACAGTACACGAACCTGGG | 21 | CCGTTCTGAATCTGCTGGTCC | 22 |
| PAX8 | TGCCTCACAACTCCATCAGA | 23 | CAGGTCTACGATGCGCTG | 24 |
| PDPN | ACATCCTTTGTTTTTGCCCA | 25 | AGTGTCATCTTCTGGCTGGC | 26 |
| PDX1 | CGTCCGCTTGTTCTCCTC | 27 | CCTTTCCCATGGATGAAGTC | 28 |
| SCGB1A1 | ATGAAACTCGCTGTCACCCT | 29 | GTTTCGATGACACGCTGAAA | 30 |
| SFTPC | AGCAAAGAGGTCCTGATGGA | 31 | CGATAAGAAGGCGTTTCAGG | 32 |
| SOX2 | GCTTAGCCTCGTCGATGAAC | 33 | AACCCCAAGATGCACAACTC | 34 |
| SOX9 | GTACCCGCACTTGCACAAC | 35 | GTGGtCCTTCTTGTGCTGC | 36 |
| VIMENTIN | CTTCAGAGAGAGGAAGCCGA | 37 | ATTCCACTTTGCGTTCAAGG | 38 |

Note: All above primer sequences were obtained from http://primerdepot.nci.nih.gov/ and all annealing temperatures 55°C unless stated otherwise.

*MUC5AC Huang, SX et al. Efficient generation of lung and airway epithelial cells from human pluripotent stem cells. *Nature Biotechnol.* 1-11 (2013). doi:10.1038/nbt.2754 Annealing temperature 60°C

SEQUENCE LISTING

<160> NUMBER OF SEQ ID NOS: 38

<210> SEQ ID NO 1
<211> LENGTH: 20
<212> TYPE: DNA
<213> ORGANISM: Artificial Sequence
<220> FEATURE:
<223> OTHER INFORMATION: synthetic

<400> SEQUENCE: 1
gggctctctg agaggcaggt                                              20

<210> SEQ ID NO 2
<211> LENGTH: 20
<212> TYPE: DNA
<213> ORGANISM: Artificial Sequence
<220> FEATURE:
<223> OTHER INFORMATION: synthetic

<400> SEQUENCE: 2
ggtgacggtg gggtttagca                                              20

<210> SEQ ID NO 3
<211> LENGTH: 19
<212> TYPE: DNA
<213> ORGANISM: Artificial Sequence
<220> FEATURE:

```
<223> OTHER INFORMATION: synthetic

<400> SEQUENCE: 3
ttgacgccga gagctacac                                                  19

<210> SEQ ID NO 4
<211> LENGTH: 19
<212> TYPE: DNA
<213> ORGANISM: Artificial Sequence
<220> FEATURE:
<223> OTHER INFORMATION: synthetic

<400> SEQUENCE: 4
gaccggtgca atcttcaaa                                                  19

<210> SEQ ID NO 5
<211> LENGTH: 21
<212> TYPE: DNA
<213> ORGANISM: Artificial Sequence
<220> FEATURE:
<223> OTHER INFORMATION: synthetic

<400> SEQUENCE: 5
cgactggagc agctactatg c                                               21

<210> SEQ ID NO 6
<211> LENGTH: 20
<212> TYPE: DNA
<213> ORGANISM: Artificial Sequence
<220> FEATURE:
<223> OTHER INFORMATION: synthetic

<400> SEQUENCE: 6
tacgtgttca tgccgttcat                                                 20

<210> SEQ ID NO 7
<211> LENGTH: 20
<212> TYPE: DNA
<213> ORGANISM: Artificial Sequence
<220> FEATURE:
<223> OTHER INFORMATION: synthetic

<400> SEQUENCE: 7
caacttctgc tacttccgcc                                                 20

<210> SEQ ID NO 8
<211> LENGTH: 19
<212> TYPE: DNA
<213> ORGANISM: Artificial Sequence
<220> FEATURE:
<223> OTHER INFORMATION: synthetic

<400> SEQUENCE: 8
cgaggcactt tgatgaagc                                                  19

<210> SEQ ID NO 9
<211> LENGTH: 18
<212> TYPE: DNA
<213> ORGANISM: Artificial Sequence
<220> FEATURE:
<223> OTHER INFORMATION: synthetic

<400> SEQUENCE: 9
cctctgtacc ccttcccg                                                   18
```

```
<210> SEQ ID NO 10
<211> LENGTH: 20
<212> TYPE: DNA
<213> ORGANISM: Artificial Sequence
<220> FEATURE:
<223> OTHER INFORMATION: synthetic

<400> SEQUENCE: 10
ggggctccag agtagaggtt                                                  20

<210> SEQ ID NO 11
<211> LENGTH: 19
<212> TYPE: DNA
<213> ORGANISM: Artificial Sequence
<220> FEATURE:
<223> OTHER INFORMATION: synthetic

<400> SEQUENCE: 11
gcctttccga ggaggagac                                                   19

<210> SEQ ID NO 12
<211> LENGTH: 20
<212> TYPE: DNA
<213> ORGANISM: Artificial Sequence
<220> FEATURE:
<223> OTHER INFORMATION: synthetic

<400> SEQUENCE: 12
tctgtgacgg atctgcactc                                                  20

<210> SEQ ID NO 13
<211> LENGTH: 20
<212> TYPE: DNA
<213> ORGANISM: Artificial Sequence
<220> FEATURE:
<223> OTHER INFORMATION: synthetic

<400> SEQUENCE: 13
gacagcaaag cactgtgtgg                                                  20

<210> SEQ ID NO 14
<211> LENGTH: 22
<212> TYPE: DNA
<213> ORGANISM: Artificial Sequence
<220> FEATURE:
<223> OTHER INFORMATION: synthetic

<400> SEQUENCE: 14
tcagcactta aaagattccg tg                                               22

<210> SEQ ID NO 15
<211> LENGTH: 23
<212> TYPE: DNA
<213> ORGANISM: Artificial Sequence
<220> FEATURE:
<223> OTHER INFORMATION: synthetic

<400> SEQUENCE: 15
gcaccaacga caggaaggat gag                                              23

<210> SEQ ID NO 16
<211> LENGTH: 20
<212> TYPE: DNA
<213> ORGANISM: Artificial Sequence
<220> FEATURE:
<223> OTHER INFORMATION: synthetic
```

<400> SEQUENCE: 16
cacgttccag agccggacat                                                    20

<210> SEQ ID NO 17
<211> LENGTH: 18
<212> TYPE: DNA
<213> ORGANISM: Artificial Sequence
<220> FEATURE:
<223> OTHER INFORMATION: synthetic

<400> SEQUENCE: 17
ctcatgttca tgccgctc                                                      18

<210> SEQ ID NO 18
<211> LENGTH: 19
<212> TYPE: DNA
<213> ORGANISM: Artificial Sequence
<220> FEATURE:
<223> OTHER INFORMATION: synthetic

<400> SEQUENCE: 18
gacaccatga ggaacagcg                                                     19

<210> SEQ ID NO 19
<211> LENGTH: 20
<212> TYPE: DNA
<213> ORGANISM: Artificial Sequence
<220> FEATURE:
<223> OTHER INFORMATION: synthetic

<400> SEQUENCE: 19
cacagtgacc acgtcgattt                                                    20

<210> SEQ ID NO 20
<211> LENGTH: 20
<212> TYPE: DNA
<213> ORGANISM: Artificial Sequence
<220> FEATURE:
<223> OTHER INFORMATION: synthetic

<400> SEQUENCE: 20
cacaaggccc tcagtacctc                                                    20

<210> SEQ ID NO 21
<211> LENGTH: 20
<212> TYPE: DNA
<213> ORGANISM: Artificial Sequence
<220> FEATURE:
<223> OTHER INFORMATION: synthetic

<400> SEQUENCE: 21
ccacagtaca cgaacctggg                                                    20

<210> SEQ ID NO 22
<211> LENGTH: 21
<212> TYPE: DNA
<213> ORGANISM: Artificial Sequence
<220> FEATURE:
<223> OTHER INFORMATION: synthetic

<400> SEQUENCE: 22
ccgttctgaa tctgctggtc c                                                  21

<210> SEQ ID NO 23
<211> LENGTH: 20

```
<212> TYPE: DNA
<213> ORGANISM: Artificial Sequence
<220> FEATURE:
<223> OTHER INFORMATION: synthetic

<400> SEQUENCE: 23
tgcctcacaa ctccatcaga                                               20

<210> SEQ ID NO 24
<211> LENGTH: 18
<212> TYPE: DNA
<213> ORGANISM: Artificial Sequence
<220> FEATURE:
<223> OTHER INFORMATION: synthetic

<400> SEQUENCE: 24
caggtctacg atgcgctg                                                 18

<210> SEQ ID NO 25
<211> LENGTH: 20
<212> TYPE: DNA
<213> ORGANISM: Artificial Sequence
<220> FEATURE:
<223> OTHER INFORMATION: synthetic

<400> SEQUENCE: 25
acatcctttg tttttgccca                                               20

<210> SEQ ID NO 26
<211> LENGTH: 20
<212> TYPE: DNA
<213> ORGANISM: Artificial Sequence
<220> FEATURE:
<223> OTHER INFORMATION: synthetic

<400> SEQUENCE: 26
agtgtcatct tctggctggc                                               20

<210> SEQ ID NO 27
<211> LENGTH: 18
<212> TYPE: DNA
<213> ORGANISM: Artificial Sequence
<220> FEATURE:
<223> OTHER INFORMATION: synthetic

<400> SEQUENCE: 27
cgtccgcttg ttctcctc                                                 18

<210> SEQ ID NO 28
<211> LENGTH: 20
<212> TYPE: DNA
<213> ORGANISM: Artificial Sequence
<220> FEATURE:
<223> OTHER INFORMATION: synthetic

<400> SEQUENCE: 28
cctttcccat ggatgaagtc                                               20

<210> SEQ ID NO 29
<211> LENGTH: 20
<212> TYPE: DNA
<213> ORGANISM: Artificial Sequence
<220> FEATURE:
<223> OTHER INFORMATION: synthetic

<400> SEQUENCE: 29
```
atgaaactcg ctgtcaccct                                              20

<210> SEQ ID NO 30
<211> LENGTH: 20
<212> TYPE: DNA
<213> ORGANISM: Artificial Sequence
<220> FEATURE:
<223> OTHER INFORMATION: synthetic

<400> SEQUENCE: 30
gtttcgatga cacgctgaaa                                              20

<210> SEQ ID NO 31
<211> LENGTH: 20
<212> TYPE: DNA
<213> ORGANISM: Artificial Sequence
<220> FEATURE:
<223> OTHER INFORMATION: synthetic

<400> SEQUENCE: 31
agcaaagagg tcctgatgga                                              20

<210> SEQ ID NO 32
<211> LENGTH: 20
<212> TYPE: DNA
<213> ORGANISM: Artificial Sequence
<220> FEATURE:
<223> OTHER INFORMATION: synthetic

<400> SEQUENCE: 32
cgataagaag gcgtttcagg                                              20

<210> SEQ ID NO 33
<211> LENGTH: 20
<212> TYPE: DNA
<213> ORGANISM: Artificial Sequence
<220> FEATURE:
<223> OTHER INFORMATION: synthetic

<400> SEQUENCE: 33
gcttagcctc gtcgatgaac                                              20

<210> SEQ ID NO 34
<211> LENGTH: 20
<212> TYPE: DNA
<213> ORGANISM: Artificial Sequence
<220> FEATURE:
<223> OTHER INFORMATION: synthetic

<400> SEQUENCE: 34
aaccccaaga tgcacaactc                                              20

<210> SEQ ID NO 35
<211> LENGTH: 19
<212> TYPE: DNA
<213> ORGANISM: Artificial Sequence
<220> FEATURE:
<223> OTHER INFORMATION: synthetic

<400> SEQUENCE: 35
gtacccgcac ttgcacaac                                               19

<210> SEQ ID NO 36
<211> LENGTH: 19
<212> TYPE: DNA
<213> ORGANISM: Artificial Sequence

```
<220> FEATURE:
<223> OTHER INFORMATION: synthetic

<400> SEQUENCE: 36
gtggtccttc ttgtgctgc                                                    19

<210> SEQ ID NO 37
<211> LENGTH: 20
<212> TYPE: DNA
<213> ORGANISM: Artificial Sequence
<220> FEATURE:
<223> OTHER INFORMATION: synthetic

<400> SEQUENCE: 37
cttcagagag aggaagccga                                                   20

<210> SEQ ID NO 38
<211> LENGTH: 20
<212> TYPE: DNA
<213> ORGANISM: Artificial Sequence
<220> FEATURE:
<223> OTHER INFORMATION: synthetic

<400> SEQUENCE: 38
attccacttt gcgttcaagg                                                   20
```

US 10,557,124 B2

COMPOSITIONS AND METHODS FOR OBTAINING STEM CELL DERIVED LUNG TISSUE, AND RELATED USES THEREOF

CROSS REFERENCE TO RELATED APPLICATIONS

The present invention claims priority to U.S. Provisional Patent Application 62/151,238, filed Apr. 22, 2015, which is incorporated by reference in its entirety.

STATEMENT REGARDING FEDERALLY SPONSORED RESEARCH OR DEVELOPMENT

This invention was made with government support under HL115372 awarded by the National Institutes of Health. The Government has certain rights in the invention.

FIELD OF THE INVENTION

The invention disclosed herein generally relates to methods and systems for converting stem cells into specific tissue(s) or organ(s) through directed differentiation. In particular, the invention disclosed herein relates to methods and systems for promoting definitive endoderm formation from pluripotent stem cells. The invention disclosed herein further relates to methods and systems for promoting ventral-anterior foregut spheroid tissue formation, 3-dimensional lung tissue formation, and lung organoid tissue formation produced in vitro from the described methods

INTRODUCTION

Pluripotent stem cells (PSCs) are the descendants of totipotent cells and can differentiate into nearly all cells, i.e., cells derived from any of the three germ layers, including endoderm (interior stomach lining, gastrointestinal tract, the lungs), mesoderm (muscle, bone, blood, urogenital), and ectoderm (epidermal tissues and nervous system).

Embryonic and induced pluripotent stem cells have had an unprecedented impact on the ability to study human diseases and to generate replacement tissues that are therapeutically effective in animal models.

In developmental biology, cellular differentiation is the process by which a less specialized cell becomes a more specialized cell type. Most successful efforts to direct the differentiation of human PSCs into therapeutic cell types have been based on studies of embryonic organ development. Examples include the generation of liver hepatocytes and pancreatic endocrine cells, which have shown functional potential in animal models of liver disease and diabetes. Similarly, differentiation of PSCs into lung tissue may provide therapeutic benefit for diseases such as end stage lung disease.

Pluripotent stem cells have the potential to differentiate into any of the three germ layers: endoderm (interior stomach lining, gastrointestinal tract, the lungs), mesoderm (muscle, bone, blood, urogenital), and ectoderm (epidermal tissues and nervous system). As such, pluripotent stem cells can give rise to any fetal or adult cell type. However, the fate of the particular pluripotent stem cells is controlled by numerous cellular signaling pathway and numerous factors. Further, the pluripotent stem cells alone cannot develop into a fetal or adult animal because they lack the potential to contribute to extraembryonic tissue, such as the placenta.

What is needed in the art are methods and systems for accurately controlling the destination of the pluripotent stem cells in order to create the specific type of tissue or organism of desire.

SUMMARY OF THE INVENTION

Breakthroughs in 3-dimensional (3D) organoid cultures for many organ systems have led to new physiologically complex in vitro models to study human development and disease. Experiments conducted during the course of developing embodiments for the present invention demonstrate step-wise differentiation of human pluripotent stem cells (hPSCs) (embryonic and induced) into lung organoids. Indeed, it was shown that by manipulating developmental signaling pathways hPSCs generate ventral-anterior foregut spheroids, which are then expanded into human lung organoids (HLOs). Such HLOs were shown to consist of epithelial and mesenchymal compartments of the lung, organized with structural features similar to the native lung. Such HLOs were shown to possess upper airway-like epithelium with basal cells and immature ciliated cells surrounded by smooth muscle and myofibroblasts, as well as an alveolar-like domain with appropriate cell types. Moreover, using RNA-sequencing, it was shown that HLOs are remarkably similar to human fetal lung based on global transcriptional profiles, thereby indicating that HLOs are an excellent model to study human lung development, maturation and disease.

Accordingly, the invention disclosed herein generally relates to methods and systems for converting stem cells into specific tissue(s) or organ(s) through directed differentiation. In particular, the invention disclosed herein relates to methods and systems for promoting definitive endoderm formation from pluripotent stem cells. The invention disclosed herein further relates to methods and systems for promoting ventral-anterior foregut spheroid tissue formation, 3-dimensional lung tissue formation, and lung organoid tissue formation produced in vitro from the described methods In certain embodiments, the present invention provides methods of inducing formation of lung organoid tissue, comprising culturing definitive endoderm cells in vitro, wherein the culturing results in differentiation of the definitive endoderm cells into tissue comprising ventral-anterior foregut spheroid tissue, wherein the culturing comprises activating and/or inhibiting one or more signaling pathways within the definitive endoderm cells, wherein the one or more signaling pathways are selected from the group consisting of the Wnt signaling pathway, the FGF signaling pathway, the BMP signaling pathway, and the TGFβ signaling pathway; obtaining ventral-anterior foregut spheroid tissue from the cultured definitive endoderm cells; culturing the obtained ventral-anterior foregut spheroid tissue in vitro, wherein the culturing results in differentiation of the obtained ventral-anterior foregut spheroid tissue into tissue comprising 3-dimensional lung tissue, wherein the culturing comprising activating the Hedgehog signaling pathway; obtaining 3-dimensional lung tissue from the cultured tissue comprising ventral-anterior foregut spheroid tissue; culturing the obtained 3-dimensional lung tissue in vitro, wherein the culturing results in differentiation of the obtained tissue comprising 3-dimensional lung tissue into tissue lung organoid tissue, wherein the culturing comprising activating the FGF signaling pathway; and obtaining lung organoid tissue from the cultured 3-dimensional lung tissue.

In certain embodiments, the present invention provides methods of inducing formation of 3-dimensional lung tissue, comprising culturing definitive endoderm cells in vitro, wherein the culturing results in differentiation of the definitive endoderm cells into tissue comprising ventral-anterior foregut spheroid tissue, wherein the culturing comprises activating and/or inhibiting one or more signaling pathways within the definitive endoderm cells, wherein the one or more signaling pathways are selected from the group consisting of the Wnt signaling pathway, the FGF signaling pathway, the BMP signaling pathway, and the TGFβ signaling pathway; obtaining ventral-anterior foregut spheroid tissue from the cultured definitive endoderm cells; culturing the obtained ventral-anterior foregut spheroid tissue in vitro, wherein the culturing results in differentiation of the obtained ventral-anterior foregut spheroid tissue into tissue comprising 3-dimensional lung tissue, wherein the culturing comprising activating the Hedgehog signaling pathway; and obtaining 3-dimensional lung tissue from the cultured tissue comprising ventral-anterior foregut spheroid tissue.

In certain embodiments, the present invention provides methods of inducing formation of ventral-anterior foregut spheroid tissue, comprising culturing definitive endoderm cells in vitro, wherein the culturing results in differentiation of the definitive endoderm cells into tissue comprising ventral-anterior foregut spheroid tissue, wherein the culturing comprises activating and/or inhibiting one or more signaling pathways within the definitive endoderm cells, wherein the one or more signaling pathways are selected from the group consisting of the Wnt signaling pathway, the FGF signaling pathway, the BMP signaling pathway, and the TGFβ signaling pathway; obtaining ventral-anterior foregut spheroid tissue from the cultured definitive endoderm cells.

Such methods are not limited to activating a particular signaling pathway within the definitive endoderm cells. In some embodiments, the activated signaling pathway is one or more of the Wnt and FGF signaling pathways.

Such methods are not limited to inhibiting a particular signaling pathway within the definitive endoderm cells. In some embodiments, the inhibited signaling pathway is one or both of the BMP and TGF-β signaling pathways.

In some embodiments, such methods comprise activating the Wnt and FGF signaling pathways and inhibiting the BMP and TGFβ signaling pathways within the definitive endoderm cells.

Such methods are not limited to a particular manner of activating the Wnt signaling pathway within the definitive endoderm cells. In some embodiments, activating the Wnt signaling pathway within the definitive endoderm cells comprises culturing the definitive endoderm cells with a small molecule or agonist that activates the Wnt signaling pathway. In some embodiments, the small molecule or agonist that activates the Wnt signaling pathway is CHIR99021. In some embodiments, activating the Wnt signaling pathway occurs through culturing the definitive endoderm cells with one or more molecules configured to activate a Wnt protein, wherein the Wnt protein is selected from the group consisting of Wnt1, Wnt2, Wnt2b, Wnt3, Wnt3a, Wnt4, Wnt5a, Wnt5b, Wnt6, Wnt7a, Wnt7b, Wnt8a, Wnt8b, Wnt9a, Wnt9b, Wnt10a, Wnt10b, Wnt11, and Wnt16. In some embodiments, activating the Wnt signaling pathway comprises culturing the definitive endoderm cells with a small molecule or other agonist that stimulates Wnt signaling. In some embodiments, the Wnt agonist is CHIR99021.

Such methods are not limited to a particular manner of activating the FGF signaling pathway within the definitive endoderm cells. In some embodiments, activating the FGF signaling pathway occurs through culturing the definitive endoderm cells with one or more molecules configured to activate a FGF protein, wherein the FGF protein is selected from the group consisting of FGF1, FGF2, FGF3, FGF4, FGF10, FGF11, FGF12, FGF13, FGF14, FGF15, FGF16, FGF17, FGF18, FGF19, FGF20, FGF21, FGF22, and FGF23. In some embodiments, activating the FGF signaling pathway within the definitive endoderm cells comprises culturing the definitive endoderm cells with a small molecule or agonist that activates the FGF signaling pathway. In some embodiments, the small molecule or agonist that activates the FGF signaling pathway is FGF4.

Such methods are not limited to a particular manner of inhibiting the BMP signaling pathway within the definitive endoderm cells. In some embodiments, inhibiting the BMP signaling pathway within the definitive endoderm cells comprises culturing the definitive endoderm cells with a small molecule or antagonist that inhibits the BMP signaling pathway. In some embodiments, the small molecule or antagonist that inhibits the BMP signaling pathway is Noggin.

Such methods are not limited to a particular manner of inhibiting the TGFβ signaling pathway within the definitive endoderm cells. In some embodiments, inhibiting the TGFβ signaling pathway within the definitive endoderm cells comprises culturing the definitive endoderm cells with a small molecule or antagonist that inhibits the TGFβ signaling pathway. In some embodiments, the small molecule or antagonist that inhibits the TGFβ signaling pathway is SB431542.

In some embodiments, activating and/or inhibiting one or more signaling pathways within the definitive endoderm cells comprises culturing the definitive endoderm cells with a Wnt signaling pathway agonist, a FGF signaling pathway agonist, a BMP signaling pathway inhibitor, and a TGFβ signaling pathway inhibitor.

In some embodiments, activating and/or inhibiting one or more signaling pathways within the definitive endoderm cells comprises culturing the definitive endoderm cells with CHIR99021, FGF4, Noggin, and SB431542.

In some embodiments, activating and/or inhibiting one or more signaling pathways within the definitive endoderm cells occurs over a specified temporal period.

In some embodiments, activating and/or inhibiting one or more signaling pathways within the definitive endoderm cells occurs comprises activating and/or inhibiting two or more signaling pathways. In some embodiments, the activating and/or inhibiting two or more signaling pathways occurs simultaneously. In some embodiments, the activating and/or inhibiting two or more signaling pathways does not occur simultaneously.

In some embodiments, the definitive endoderm cells are derived from pluripotent stem cells. In some embodiments, the pluripotent stem cells are embryonic stem cells and/or induced pluripotent stem cells. In some embodiments, the definitive endoderm cells are derived by contacting the pluripotent stem cell with Activin A. In some embodiments, the pluripotent stem cells are human pluripotent stem cells.

Such methods are not limited to a particular manner of activating the Hedgehog signaling pathway within the obtained ventral-anterior foregut spheroid tissue. In some embodiments, culturing the obtained ventral-anterior foregut spheroid tissue occurs through activating the Hedgehog signaling pathway occurs through culturing the obtained ventral-anterior foregut spheroid tissue with a small molecule or agonist that activates the Hedgehog signaling pathway. In some embodiments, the small molecule or agonist that activates the Hedgehog signaling pathway is smoothened agonist (SAG).

Such methods are not limited to a particular manner of activating the FGF signaling pathway within the obtained 3-dimensional lung tissue. In some embodiments, culturing the obtained 3-dimensional lung tissue through activating the FGF signaling pathway occurs through culturing the obtained 3-dimensional lung tissue with a small molecule or agonist that activates the FGF signaling pathway. In some embodiments, the small molecule or agonist that activates the FGF signaling pathway is selected from FGF1, FGF2, FGF3, FGF4, FGF10, FGF11, FGF12, FGF13, FGF14, FGF15, FGF16, FGF17, FGF18, FGF19, FGF20, FGF21, FGF22, and FGF23. In some embodiments, the small molecule or agonist that activates the FGF signaling pathway is FGF10.

In some embodiments, the culturing and obtaining steps are conducted in vitro.

In some embodiments, the obtained lung organoid tissue comprises one or more of upper airway-like epithelium with basal cells, immature ciliated cells surrounded by smooth muscle and myofibroblasts, and alveolar-like cells.

In certain embodiments, the present invention provides compositions comprising or consisting of ventral-anterior foregut spheroid tissue produced in vitro from the described methods.

In certain embodiments, the present invention provides compositions comprising or consisting of 3-dimensional lung tissue produced in vitro from the described methods.

In certain embodiments, the present invention provides compositions comprising or consisting of lung organoid tissue produced in vitro from the described methods.

In certain embodiments, the present invention provides compositions comprising or consisting of ventral-anterior foregut spheroid tissue, and/or 3-dimensional lung tissue, and/or lung organoid tissue produced in vitro from the described methods.

In certain embodiments, the present invention provides kits comprising ventral-anterior foregut spheroid tissue produced in vitro from the described methods.

In certain embodiments, the present invention provides kits comprising 3-dimensional lung tissue produced in vitro from the described methods.

In certain embodiments, the present invention provides kits comprising lung organoid tissue produced in vitro from the described methods.

In certain embodiments, the present invention provides kits comprising or consisting of ventral-anterior foregut spheroid tissue, and/or 3-dimensional lung tissue, and/or lung organoid tissue produced in vitro from the described methods.

BRIEF DESCRIPTION OF DRAWINGS

FIG. 1A-F: Generation of three-dimensional ventral anterior foregut spheroids from endoderm monolayers. (A) hESCs were differentiated into foregut endoderm by treating cells with 4 days of Activin A (ACTA) followed by 4 days of NOG+SB. (B) Foregut endoderm (NOG+SB) had high expression of the foregut marker SOX2 while the hindgut marker CDX2 was significantly reduced compared to untreated endoderm controls (End). NOG+SB monolayer had high expression of ventral anterior foregut genes NKX2.1 and PAX8 while the posterior foregut marker PDX1 was reduced. The foregut marker HHEX is expressed in the developing liver, biliary system, and thyroid and remained unchanged. (C) The majority of cells in NOG+SB treated cultures were SOX2 positive (gray-scaled green) compared to the control, in which only scattered clusters of cells were SOX2 positive. Scale bar represents 200 µm. (D) hESCs were differentiated into foregut spheroids by treating cells with 4 days of ACTA and then additional 4 to 6 days of NOG+SB+FGF4+Ch. Representative images of a spheroid in a matrigel droplet shown as whole mount image. Scale bar represents 100 µm. (E) Foregut spheroids (NOG+SB+FGF4+Ch) had high expression of the foregut marker SOX2 while the hindgut marker CDX2 was significantly reduced compared to untreated endoderm control (End) (top panel). Spheroids had high expression of anterior foregut genes NKX2.1 and PAX8 while the posterior foregut marker PDX1 was reduced and HHEX was unchanged (bottom panel). *p<0.05, error bars represent SEM. (F) The majority of cells in foregut spheroids are FOXA2+ (gray-scaled green, left panel) and SOX2+ (white, right panel) and ECAD+ (gray-scaled red, right panel). Scale bar represent 50 µm.

FIG. 6A-D: Induction of NKX2.1 in anterior foregut endoderm by modulating FGF and HH signaling. (A) hESCs were differentiated into endoderm (End) or anterior foregut with NOG+SB (For). Anterior foregut was treated with low (50 ng/mL) and high (500 ng/mL) concentrations of FGF2. FGF2 caused a dose dependent increase in SHH and PAX8 expression with a modest increase in NKX2.1 expression compared to untreated endoderm controls. Note that NKX2.1 expression is increased by NOG+SB exposure alone (no FGF2). (B) Addition of the FGF inhibitor SU5402 (SU) to NOG+SB foregut cultures (For) caused a significant reduction of SHH and PAX8 expression, but NKX2.1, GLI1, and PTCH1 were not significantly different compared to the foregut controls, in which no growth factors were added after SB+NOG. (C) Addition of the HH inhibitor Sant-2 caused a significant reduction in NKX2.1 compared to foregut control. Similarly when FGF2 (500 ng/mL) and Sant-2 were added simultaneously, the modest NKX2.1 induction caused by FGF2 was significantly reduced whereas PAX8 expression remained unchanged. (D) Foregut endoderm treated with SAG or SAG+SU for 8 days had a 6.5 fold and 21 fold increase of NKX2.1 expression, respectively, compared to untreated foregut controls. PAX8 expression was unchanged in the SAG treated cultures whereas SAG+SU treated cultures demonstrated a 41 fold decrease in PAX8 expression. End=endoderm; For=foregut in all panels. *p<0.05, error bars represent SEM.

FIG. 10A-E: HH-induced ventral foregut spheroids give rise to lung organoids. (A) hESCs were differentiated into foregut spheroids by treating cells with 4 days of ACTA and then additional 4 to 6 days of NOG+SB+FGF4+Ch with the addition of the HH agonist SAG. Representative whole mount images of spheroids in a matrigel droplet are shown at low (left, scale bar 200 μm) and high magnification (right, scale bar 100 μm). (B) The addition of SAG to the NOG+SB+FGF4+Ch spheres caused a reduction in SOX2 and CDX2 transcripts (top panel) and a significant increase of NKX2.1 transcript (bottom panel) compared to NOG+SB+FGF4+Ch spheres (without SAG). Other foregut lineages (PAX8, PDX1, HHEX) were not significantly different when SAG was added. (C) The majority of the cells in NOG+SB+FGF4+Ch+SAG spheres expressed FOXA2, SOX2 and NKX2.1 protein. Scale bars represent 50 μm. (D) Timeline showing NOG+SB+FGF4+Ch+SAG induced foregut spheroids grown and maintained in FGF10. Note that Day 1 is the day spheroids were plated in Matrigel. Scale bar represents 100 μm. (E) Organoids express lung markers in a manner consistent with mouse lung development. All expression is shown relative to undifferentiated pluripotent stem cells (hPSC), and adult human lung is shown as a reference. Lung progenitor markers NMYC and ID2 were very low in adult lung, and were expressed at high levels in early organoid cultures, but were reduced over time (D=Days in culture), whereas NKX2.1 expression remained relatively constant. In contrast, SFTPC is known to be expressed at low levels in distal lung progenitors, but increases and is highly expressed in AECII cells. Consistently, SFTPC is highly expressed in adult human lungs and increases over time in organoid cultures and the AECI marker HOPX is also highly expressed in adult human lung and increases over time in organoids. *p<0.05. All error bars represent SEM.

Figure 1A:
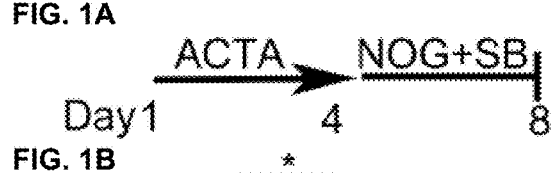

(white) as separate domains in the epithelium labeled by ECAD (gray-scaled red). Z-stack images are shown every 40 μm sections through the HLO. Scale bar represents 200 μm.

FIG. 15A-E: (A) Genes expressed in the proximal airway were examined in organoids across time. The proximal airway cell marker SOX2 decreased over time in HLOs cultures compared to D10 HLOs. Compared to undifferentiated hPSCs, organoids expressed high levels of the basal cell marker P63 at all time points, while the club cell marker SCGB1A1 and ciliated cell marker FOXJ1 had a significant increase of expression in prolonged cultures (compared to D10 HLOs). There was an increasing but non-significant trend in goblet cell MUC5AC expression over time in culture. (B) D65 HLOs had structures resembling the proximal airway, in which the epithelium (β-catenin, gray-scaled red) possesses P63+ basal cells (gray-scaled green), and is surrounded by SMA+ (white, upper and lower left panel) mesenchymal tissue. Adjacent to the P63 positive basal cell layer (gray-scaled green, lower, right panel) were FOXJ1 positive cells (white). Scale bars represent 50 μM (top) and 10 μM (bottom). (C) Proximal airway-like epithelium (β-catenin, gray-scaled green) co-stained for ACTTUB on the apical side of the cell (gray-scaled red). Scale bars represent 50 μM (top) and 10 μM (bottom). (D). Proximal airway-like epithelium (E-cadherin, gray-scaled red) also co-stained with Club cell marker CC10 (white, right panel). Scale bars represent 50 μM (top) and 10 μM (bottom). (E) Acellular human lung matrix was seeded with spheroids and cultured for 40 days (D40). Matrices had abundant proximal airway-like structures that had multi-ciliated cells on the apical surfaced labeled by ACTTUB (gray-scaled red, top panel) in low (scale bar 50 μM) and high magnification (scale bar 10 μM). Serial sections showed that cells were also FOXJ1 positive (white, lower panel) with the epithelium outlined in ECAD (gray-scaled green) in low (scale bar 50 μM) and high magnification (scale bar 10 μM). (B-D) 1' in high magnification images indicates the lumen. *p<0.05. All error bars represent SEM.

Figure 16A:
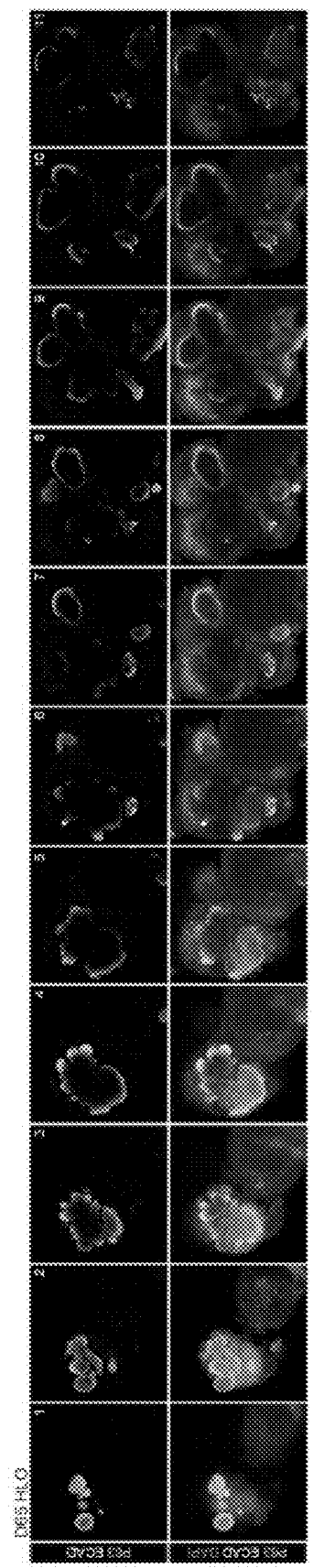
Figure 16B:
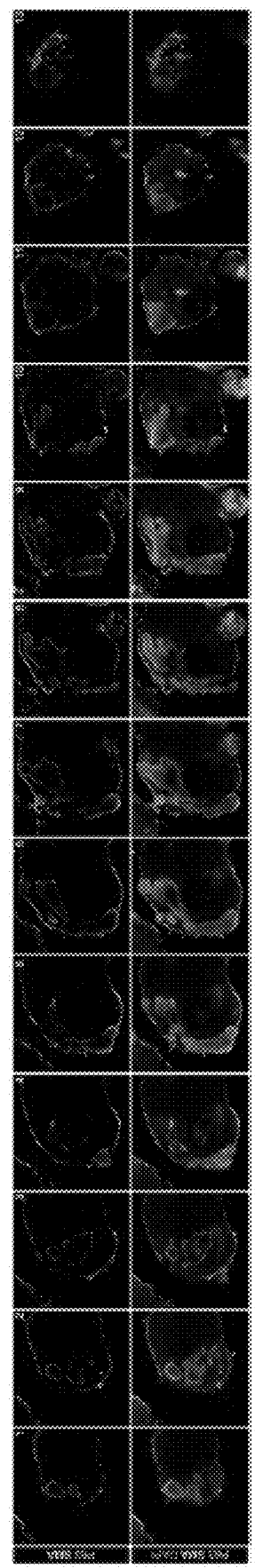

FIG. 16A-B: Lung organoids have P63+ epithelium throughout the organoid. (A) Confocal Z-slices taken at every 40 μm show P63+ (gray-scaled green) and ECAD+ (white) structures through the D65 HLO. (B) Z-slices taken at every 40 μm show SMA (white) surrounding the periphery the HLO with P63 (gray-scaled green) staining within the HLO. Scale bars represent 200 μm.

Figure 17A:
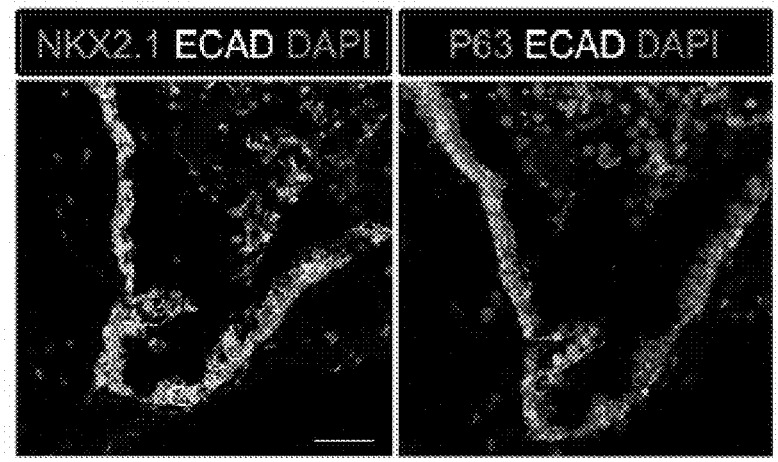
Figure 17B:
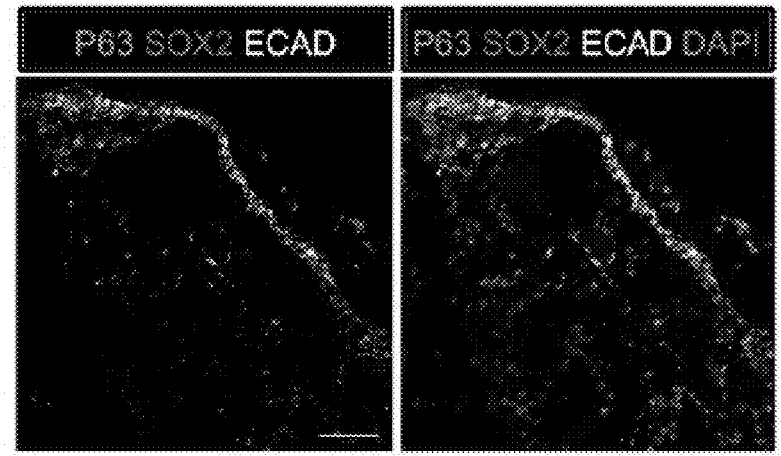

FIG. 17A-B: P63+ cells have an NKX2.1+ lung identity. (A) Serial sections were stained with NKX2.1 and P63 respectively. The adjacent sections expressed ECAD (white) and NKX2.1 (gray-scaled green) in the first section and P63 (gray-scaled green) in the second section. (B) P63+ cells (gray-scaled green) co-expressed the proximal lung marker SOX2 (gray-scaled red) in the epithelium labeled by ECAD (white). Scale bars represent 50 μm.

FIG. 18A-C: Lung organoids possess multiple types of mesenchymal cells. (A) D65 HLOs have PDGFRα+ (gray-scaled green) VIM+ (white) double-positive myofibroblasts and PDGFRα-/VIM+ fibroblasts. Scale bar represents 50 μm. (B) D65 HLOs also possesses PDGFRα+ (gray-scaled green) SMA+ (white) double-positive myofibroblasts and PDGFRα-/SMA+ smooth muscle and myofibrblasts. Scale bar represents 50 μm. (C) D65 HLO do not contain any cartilage whereas positive control iPSC derived teratoma had clear SafraninO staining specific to cartilage. Fast gray-scaled green marks the cytoplasm and hematoxylin the nuclei of both tissues. Scale bar represents 100 μm.

FIG. 19A-D: Lung organoids possess abundant distal bipotent progenitor cells. (A) The expression of the distal progenitor marker SOX9 remained unchanged over time and the AECI marker PDPN had low expression in HLO cultures. (B) The majority of SFTPC+ cells (gray-scaled green, left panel) co-expressed SOX9 (gray-scaled red). Similarly, many cells expressing the AECI early marker HOPX+ (gray-scaled green, right panel) co-expressed SOX9 (gray-scaled red). Few, scattered cells expressed the late AECII marker SFTPB (white, second panel) or the AECI marker, PDPN (third panel, white). Few PDPN+ cells also showed elongated, squamous morphology seen in the adult lung. (C) Human lung AECII cells labeled with SFTPC (gray-scaled green, left panel) did not co-express SOX9. SFTPB+ cells (white, second panel) in the adult human lung have similar morphology to SFTPB+ cells in HLOs. Human lung AECI cells expressed PDPN (white, third panel), and show characteristic AECI cell shape. Human AECI cells express HOPX (gray-scaled green, right panel), but did not co-express SOX9. (B-C) Scale bar in lower magnification images in B (upper panel) represent 50 μM and higher magnification in B,C (lower panel) represent 10 μM. (D) D50 HLOs contain lamellar bodies which are organelles specific to AECII cells. Scale bars represent 500 nm.

Figure 20:
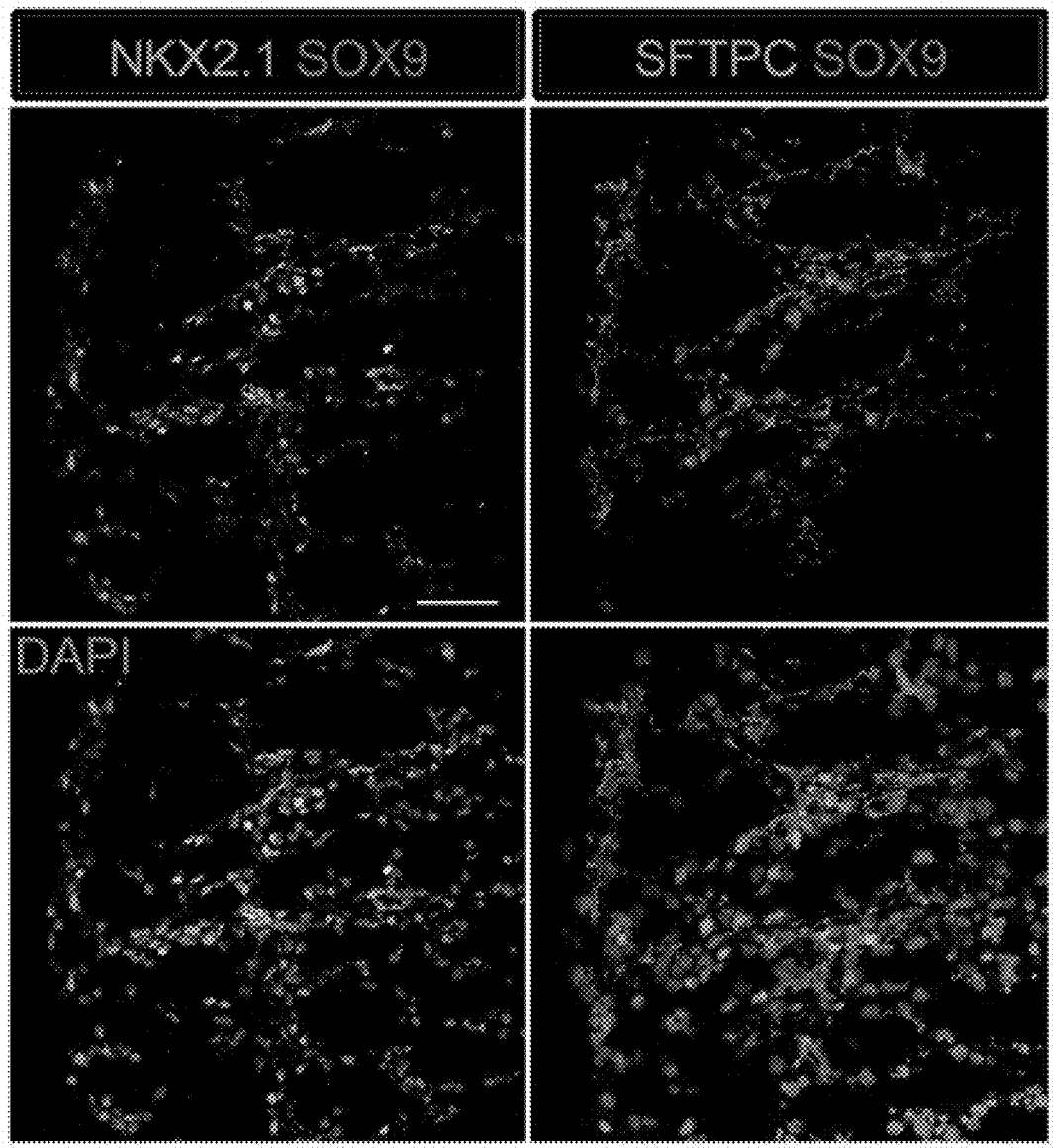
Figure 23A:
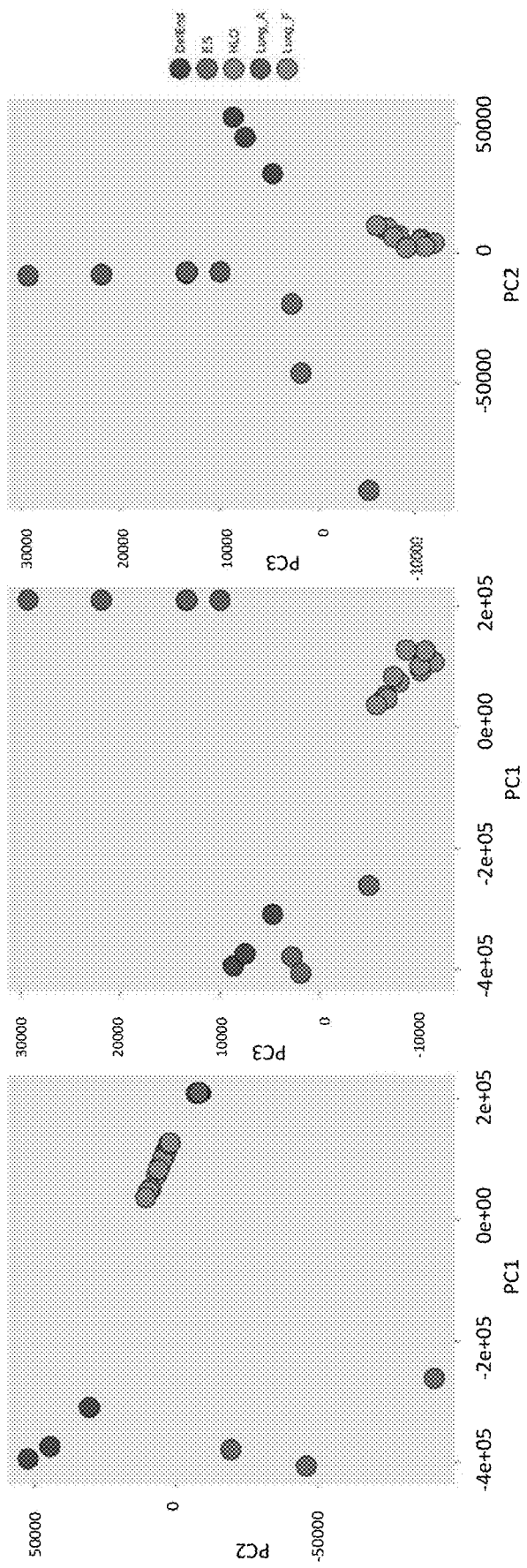
Figure 23B:
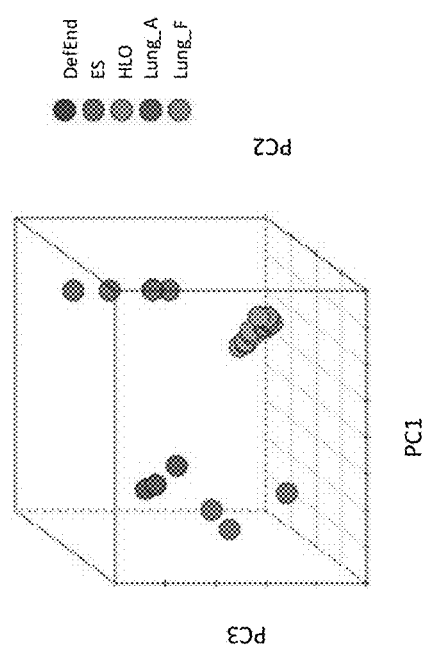
Figure 23C:
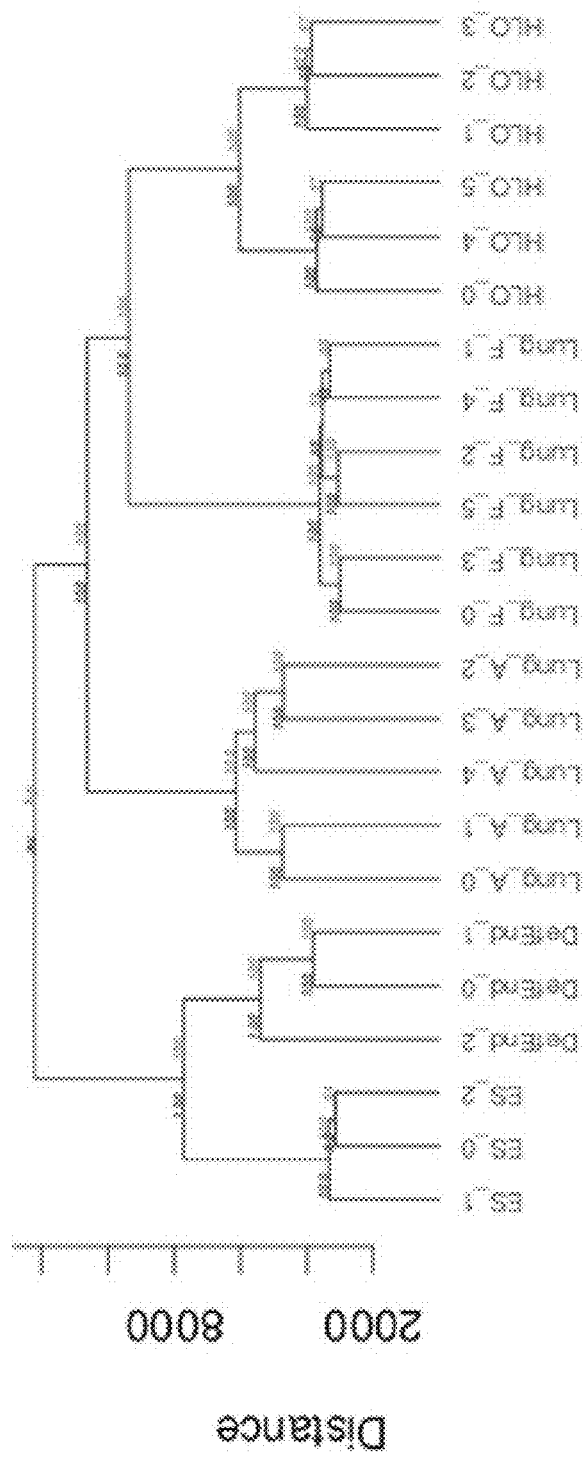
Figure 23D:
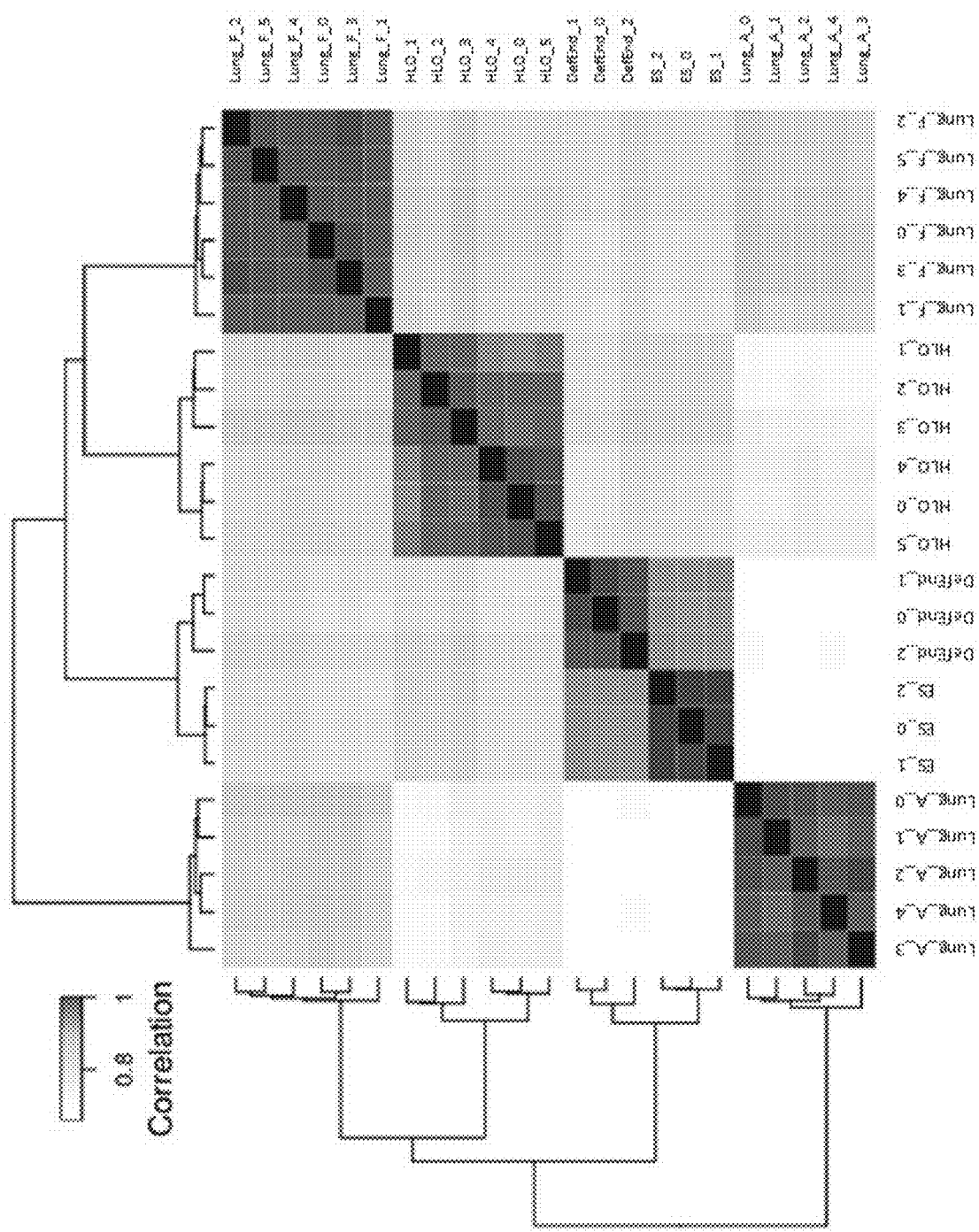

FIG. 20: SFTPC+ cells express lung specific markers. D65 HLOs express lung epithelial markers NKX2.1 (gray-scaled green) and SOX9 (gray-scaled red) and the adjacent section expresses SFTPC (gray-scaled green) and SOX9 (gray-scaled red). Scale bar represents 50 μm.

FIG. 21A-G: Quantitative assessment of the composition of lung organoids. (A) HLOs were assessed for proximal airway-like structures (P63+) and distal airway-like structures (P63-/SFTPC+). 81% of HLOs have proximal airway-like epithelium while 100% have distal airway-like epithelium (n=48 individual HLOs). (B) The average cross-sectional area within an HLO that is comprised of P63+ proximal airway-like and P63- distal airway-like epithelium was calculated. Proximal structures comprised 14.5% (+/- 0.6%) of the entire area of the HLO (P63+), whereas 85.5% (+/-0.6%) of HLO was distal-like epithelium and mesenchyme (P63-). (C-G) The percent of specific cell markers present in an organoid was determined by dividing by the total number of Dapi+ nuclei within the same section (n=15 individual HLOs). Each point represents the data from an individual HLO while the open bar represents the average percent of cells. (C) On average, 57% of all cells in the HLOs were NKX2.1+, (D) 39% of all cells were P63+, (E) 3% were FOXJ1+, (F) 5% were SFTPC+, (G) 4% of all cells were HOPX+. (B-G) Error bars represent SEM.

FIG. 22: A table showing publicly available RNAseq datasets utilized for human fetal lung representing a range of gestational stages, and for adult human lung (see, Example VII).

FIG. 23A-D: RNA sequencing analysis associates HLOs with fetal lung tissue. 6 HLOs (n=3 D65 HLOs and n=3 D110 HLOs) were compared to the undifferentiated H9 stem cells (SC) and definitive endoderm (Def End) and publicly available datasets of adult and fetal human lungs (see Supplemental Table 1). (A-B) Principle component (PC) analysis, (C) hierarchical clustering, and (D) Spearman's correlation all demonstrate that HLOs are most closely related to the fetal lung.

FIG. 24: A table providing antibody information and dilutions as described in Example VIII.

FIG. 25: A table providing a list of primer sequences utilized in RNA extraction and qRT-PCR as described in Example VIII.

DEFINITIONS

As used herein, the term "pluripotent stem cells (PSCs)," also commonly known as PS cells, encompasses any cells that can differentiate into nearly all cells, i.e., cells derived from any of the three germ layers (germinal epithelium), including endoderm (interior stomach lining, gastrointestinal tract, the lungs), mesoderm (muscle, bone, blood, urogenital), and ectoderm (epidermal tissues and nervous system). PSCs can be the descendants of totipotent cells, derived from embryonic stem cells (including embryonic germ cells) or obtained through induction of a non-pluripotent cell, such as an adult somatic cell, by forcing the expression of certain genes.

As used herein, the term "embryonic stem cells (ESCs)," also commonly abbreviated as ES cells, refers to cells that are pluripotent and derived from the inner cell mass of the blastocyst, an early-stage embryo. For purpose of the present invention, the term "ESCs" is used broadly sometimes to encompass the embryonic germ cells as well.

As used herein, the term "induced pluripotent stem cells (iPSCs)," also commonly abbreviated as iPS cells, refers to a type of pluripotent stem cells artificially derived from a normally non-pluripotent cell, such as an adult somatic cell, by inducing a "forced" expression of certain genes.

As used herein, the term "precursor cell" encompasses any cells that can be used in methods described herein, through which one or more precursor cells acquire the ability to renew itself or differentiate into one or more specialized cell types. In some embodiments, a precursor cell is pluripotent or has the capacity to becoming pluripotent. In some embodiments, the precursor cells are subjected to the treatment of external factors (e.g., growth factors) to acquire pluripotency. In some embodiments, a precursor cell can be a totipotent (or omnipotent) stem cell; a pluripotent stem cell (induced or non-induced); a multipotent stem cell; an oligopotent stem cells and a unipotent stem cell. In some embodiments, a precursor cell can be from an embryo, an infant, a child, or an adult. In some embodiments, a precursor cell can be a somatic cell subject to treatment such that pluripotency is conferred via genetic manipulation or protein/peptide treatment.

In developmental biology, cellular differentiation is the process by which a less specialized cell becomes a more specialized cell type. As used herein, the term "directed differentiation" describes a process through which a less specialized cell becomes a particular specialized target cell type. The particularity of the specialized target cell type can be determined by any applicable methods that can be used to define or alter the destiny of the initial cell. Exemplary methods include but are not limited to genetic manipulation, chemical treatment, protein treatment, and nucleic acid treatment.

As used herein, the term "cellular constituents" are individual genes, proteins, mRNA expressing genes, and/or any other variable cellular component or protein activities such as the degree of protein modification (e.g., phosphorylation), for example, that is typically measured in biological experiments (e.g., by microarray or immunohistochemistry) by those skilled in the art. Significant discoveries relating to the complex networks of biochemical processes underlying living systems, common human diseases, and gene discovery and structure determination can now be attributed to the application of cellular constituent abundance data as part of the research process. Cellular constituent abundance data can help to identify biomarkers, discriminate disease subtypes and identify mechanisms of toxicity.

As used herein, the term "organoid" is used to mean a 3-dimensional growth of mammalian cells in culture that retains characteristics of the tissue in vivo, e.g. prolonged tissue expansion with proliferation, multilineage differentiation, recapitulation of cellular and tissue ultrastructure, etc.

DETAILED DESCRIPTION OF THE INVENTION

Directed differentiation of human pluripotent stem cells (hPSCs), which include embryonic (hESCs) and induced (iPSCs), is one of the most efficient approaches to achieving differentiation of a cell or tissue of interest (see, e.g., Spence J R, et al., Nature. 2011 Feb. 3; 470(7332):105-9; D'Amour K A, et al., Nat Biotechnol. 2005 Oct. 28; 23(12):1534-41; Kroon E, et al., Nat Biotechnol. 2008 Feb. 20; 26(4):443-52; Si-Tayeb K, et al., Hepatology. 2009 Oct. 1; 51(1):297-305; Wong A P, et al., Nat Biotechnol. 2012 Aug. 26). Using this approach, differentiation of hPSCs into lung lineages has been achieved using diverse methodology with varying degrees of success (see, e.g., Wong A P, et al., Nat Biotechnol. 2012 Aug. 26; Huang S X L, et al., Nat Biotechnol; 2013 Dec. 1; 1-11; Firth A L, et al., Proceedings of the National Academy of Sciences. 2014 Apr. 29; 111(17):E1723-30; Mou H, et al., Cell Stem Cell. 2012 Apr. 6; 10(4):385-97; Ghaedi M, et al., J. Clin. Invest. 2013 Nov. 1; 123(11):4950-62; Kadzik R S, et al., Cell Stem Cell. 2012 Apr. 6; 10(4):355-61; Longmire T A, et al., Cell Stem Cell. 2012 Apr. 6; 10(4):398-411).

Thus far, the majority of efforts to differentiate lung lineages from hPSCs have focused on using 2-dimensional (2D) monolayer cultures. Several recent advances in generating 3-dimensional (3D) organ-like tissues, called "organoids", have been reported (see, e.g., Spence J R, et al., Nature. 2011 Feb. 3; 470(7332):105-9; Lancaster M A, et al., Nature. 2013 Sep. 19; 501(7467):373-9; Takebe T, et al., Nature. 2013 Jul. 25; 499(7459):481-4; Nakano T, et al., Cell Stem Cell. 2012 Jun. 14; 10(6):771-85; Meyer J S, et al., Stem Cells. 2011 August; 29(8):1206-18; McCracken K W, et al., Nature; 2014 Oct. 29; 1-19). Such 3D models offer several advantages; they often possess structural organization similar to the native organ, cell types from multiple germ layers (for example, mesoderm and endoderm (see, e.g., Spence J R, et al., Nature. 2011 Feb. 3; 470(7332):105-9; McCracken K W, et al., Nature; 2014 Oct. 29; 1-19; Wells J M, et al., Development. 2014 February; 141(4):752-60. PMCID: PMC3912826), and multiple cellular lineages making them a physiologically complex model to study developmental processes, tissue homeostasis and pathological conditions in vitro.

Previous work has demonstrated that activation of FGF and WNT signaling synergistically drives CDX2+ intestinal lineage commitment in hPSC-derived endoderm and also drives "morphogenesis in a dish", where the 2D tissue self-organizes into 3D spheroids comprised of mesenchymal and polarized epithelial layers that detach from the adherent cell layer (see, e.g., Spence J R, et al., Nature. 2011 Feb. 3; 470(7332):105-9). It has also been demonstrated that inhibition of BMP and TGFβ signaling is able to drive tissue into a SOX2+ foregut lineage (see, e.g., McCracken K W, et al., Nature; 2014 Oct. 29; 1-19; Green M D, et al., Nat Biotechnol; 2011 Feb. 27; 1-7).

Experiments conducted during the course of developing embodiments for the present invention demonstrated that simultaneous stimulation of WNT and FGF signaling while inhibiting BMP/TGFβ signaling pathways in hPSC-derived endoderm cultures prevents intestinal lineage commitment, and instead, favors a SOX2+ anterior foregut fate while also robustly generating SOX2+ anterior foregut 3D spheroid structures.

In order to further restrict foregut spheroids to the lung lineage, such experiments additionally focused on manipulating FGF and HH signaling. In the mouse, high levels of Fgf signaling have been shown to induce Shh expression in the lung endoderm (see, e.g., Rankin S A, et al., J Cell Biochem. 2014 Mar. 19; Hebrok M, et al., Genes & Development. 1998; Morrisey E E, et al., Developmental Cell. Elsevier Inc; 2010 Jan. 19; 18(1):8-23) which is accompanied by induction of the Nkx2.1+ lung progenitor field (see, e.g., Hebrok M, et al., Genes & Development. 1998; Serls A E; Development. 2004 Dec. 2; 132(1):35-47). Shh then signals from the endoderm to the mesoderm, and mutations in Shh, Gli2 or Gli3 lead to perturbed lung development, with Gli2/Gli3 double knockout mice showing lung agenesis (see, e.g., Motoyama J, et al., Nat Genet. 1998 September; 20(1):54-7; Li Y, et al., Developmental Biology. 2004 Jun. 1; 270(1):214-31; Bellusci S, et al., Development. 1997 January; 124(1):53-63).

Experiments conducted during the course of developing embodiments for the present invention demonstrated that FGF2 induces NKX2.1, PAX8, and SHH in human foregut endoderm cultures. By using pharmacological inhibitors of FGF and HH signaling SHH was shown to be required for NKX2.1 expression downstream of FGF2, and that FGF2 also induces PAX8 independently of HH signaling. These observations suggest a paradigm where $FGF^{Lo}/HH^{Hi}$ conditions preferentially induce $PAX8^{Lo}/NKX2.1^{Hi}$ lung progenitors and $FGF^{Hi}/HH^{Lo}$ conditions favor a $PAX8^{Hi}/NKX2.1^{Lo}$ fate. Given that Pax8 is required for thyroid development, experiments were conducted focusing on defining the most robust conditions to induce NKX2.1 while minimizing PAX8 expression (see, e.g., Li Y, et al., Developmental Biology. 2004 Jun. 1; 270(1):214-31; Kimura S, et al., Genes Dev. January 1; 10(1):60-927; Yuan B, et al., Dev. Dyn. 2000 February; 217(2):180-90; Narumi S, et al., Eur. J. Endocrinol. 2012 November; 167(5):625-32; Vilain C, et al., J. Clin. Endocrinol. Metab. 2001 January; 86(1):234-8; Mansouri A, et al., Nat Genet. 1998 May; 19(1):87-90; Kusakabe T, et al., Mol. Endocrinol. 2006 August; 20(8):1796-809; Cane A, et al., Hum. Mol. Genet. 2009 Jun. 15; 18(12):2266-76). By applying $HH^{Hi}$ conditions during generation of foregut spheroids NKX2.1 expression was shown to be enhanced in foregut spheroids and was shown to subsequently expand spheroids in media containing FGF10, allowing them to grow into organoids. Organoids persisted in culture for over 100 days and developed well-organized proximal-like airway epithelial structures that had many cell types found in the proximal lung epithelium, including basal and ciliated cells along with rare club cells. Moreover, proximal airway structures were often surrounded by smooth muscle actin (SMA) positive mesenchymal tissue. Organoids also possessed distal-like epithelial cells that co-expressed progenitor markers, SFTPC/SOX9 and HOPX/SOX9, consistent with early bipotent alveolar progenitor cells seen in mice (see, e.g., Desai T J, et al., Nature. 2014 Feb. 5; Treutlein B, et al., Nature. 2014 May 15; 509(7500):371-5). To support the idea that organoids may be more similar to a developing lung with abundant progenitor cells, RNA-sequencing was used to compare the global transcriptional profile of organoids to the human fetal and adult lung, undifferentiated hESCs and definitive endoderm. Principal component analysis, hierarchical clustering and Spearman's correlation all showed that organoids have striking similarity to the human fetal lung.

Taken together, such experiments demonstrate an efficient and robust in vitro system to generate complex, ventral-anterior foregut spheroid tissue formation, 3-dimensional lung tissue, and lung organoid tissue that are immature/fetal in nature.

In some embodiments, an important step is to obtain stem cells that are pluripotent or can be induced to become pluripotent. In some embodiments, pluripotent stem cells are derived from embryonic stem cells, which are in turn derived from totipotent cells of the early mammalian embryo and are capable of unlimited, undifferentiated proliferation in vitro. Embryonic stem cells are pluripotent stem cells derived from the inner cell mass of the blastocyst, an early-stage embryo. Methods for deriving embryonic stem cells from blastocytes are well known in the art. For example, three cell lines (H1, H13, and H14) have a normal XY karyotype, and two cell lines (H7 and H9) have a normal XX karyotype.

Additional stem cells that can be used in embodiments in accordance with the present invention include but are not limited to those provided by or described in the database hosted by the National Stem Cell Bank (NSCB), Human Embryonic Stem Cell Research Center at the University of California, San Francisco (UCSF); WISC cell Bank at the Wi Cell Research Institute; the University of Wisconsin Stem Cell and Regenerative Medicine Center (UW-SCRMC); Novocell, Inc. (San Diego, Calif.); Cellartis AB (Goteborg, Sweden); ES Cell International Pte Ltd (Singapore); Technion at the Israel Institute of Technology (Haifa, Israel); and the Stem Cell Database hosted by Princeton University and the University of Pennsylvania. Indeed, embryonic stem cells that can be used in embodiments in accordance with the present invention include but are not limited to SA01 (SA001); SA02 (SA002); ES01 (HES-1); ES02 (HES-2); ES03 (HES-3); ESO4 (HES-4); ES05 (HES-5); ES06 (HES-6); BG01 (BGN-01); BG02 (BGN-02); BG03 (BGN-03); TE03 (13); TE04 (14); TE06 (16); UC01 (HSF1); UC06 (HSF6); WA01 (H1); WA07 (H7); WA09 (H9); WA13 (H13); WA14 (H14).

In some embodiments, the stem cells are further modified to incorporate additional properties. Exemplary modified cell lines include but not limited to H1 OCT4-EGFP; H9 Cre-LoxP; H9 hNanog-pGZ; H9 hOct4-pGZ; H9 in GFPhES; and H9 Syn-GFP.

More details on embryonic stem cells can be found in, for example, Thomson et al., 1998, *Science* 282 (5391):1145-1147; Andrews et al., 2005, *Biochem Soc Trans* 33:1526-1530; Martin 1980, *Science* 209 (4458):768-776; Evans and Kaufman, 1981, *Nature* 292(5819): 154-156; Klimanskaya et al., 2005, *Lancet* 365 (9471): 1636-1641).

Alternative, pluripotent stem cells can be derived from embryonic germ cells (EGCs), which are the cells that give rise to the gametes of organisms that reproduce sexually. EGCs are derived from primordial germ cells found in the gonadal ridge of a late embryo, have many of the properties of embryonic stem cells. The primordial germ cells in an embryo develop into stem cells that in an adult generate the reproductive gametes (sperm or eggs). In mice and humans it is possible to grow embryonic germ cells in tissue culture under appropriate conditions. Both EGCs and ESCs are pluripotent. For purpose of the present invention, the term "ESCs" is used broadly sometimes to encompass EGCs.

In some embodiments, iPSCs are derived by transfection of certain stem cell-associated genes into non-pluripotent cells, such as adult fibroblasts. Transfection is typically achieved through viral vectors, such as retroviruses. Transfected genes include the master transcriptional regulators Oct-3/4 (Pouf51) and Sox2, although it is suggested that other genes enhance the efficiency of induction. After 3-4 weeks, small numbers of transfected cells begin to become morphologically and biochemically similar to pluripotent stem cells, and are typically isolated through morphological selection, doubling time, or through a reporter gene and antibiotic selection. As used herein, iPSCs include but are not limited to first generation iPSCs, second generation iPSCs in mice, and human induced pluripotent stem cells. In some embodiments, a retroviral system is used to transform human fibroblasts into pluripotent stem cells using four pivotal genes: Oct3/4, Sox2, Klf4, and c-Myc. In alternative embodiments, a lentiviral system is used to transform somatic cells with OCT4, SOX2, NANOG, and LIN28. Genes whose expression are induced in iPSCs include but are not limited to Oct-3/4 (e.g., Pou5fl); certain members of the Sox gene family (e.g., Sox1, Sox2, Sox3, and Sox15); certain members of the Klf family (e.g., Klf1, Klf2, Klf4, and Klf5), certain members of the Myc family (e.g., C-myc, L-myc, and N-myc), Nanog, and LIN28.

More details on induced pluripotent stem cells can be found in, for example, Kaji et al., 2009, *Nature* 458:771-775; Woltjen et al., 2009, *Nature* 458:766-770; Okita et al., 2008, *Science* 322(5903):949-953; Stadtfeld et al., 2008, *Science* 322(5903):945-949; and Zhou et al., 2009, *Cell Stem Cell* 4(5):381-384.

In some embodiments, examples of iPS cell lines include but not limited to iPS-DF19-9; iPS-DF19-9; iPS-DF4-3; iPS-DF6-9; iPS(Foreskin); iPS(IMR90); and iPS(IMR90).

The lungs of mammals including those of humans, have a soft, spongelike texture and are honeycombed with epithelium, having a much larger surface area in total than the outer surface area of the lung itself.

Breathing is largely driven by the muscular diaphragm at the bottom of the thorax. Contraction of the diaphragm pulls the bottom of the cavity in which the lung is enclosed downward, increasing volume and thus decreasing pressure, causing air to flow into the airways. Air enters through the oral and nasal cavities; it flows through the pharynx, then the larynx and into the trachea, which branches out into the main bronchi and then subsequent divisions. During normal breathing, expiration is passive and no muscles are contracted (the diaphragm relaxes). The rib cage itself is also able to expand and contract to some degree through the use of the intercostal muscles, together with the action of other respiratory and accessory respiratory muscles. As a result, air is transported into or expelled out of the lungs.

In humans, the trachea divides into two main bronchi that enter the roots of the lungs. The bronchi continue to divide within the lung, and after multiple divisions, give rise to bronchioles. The bronchial tree continues branching until it reaches the level of terminal bronchioles, which lead to alveolar sacs. Alveolar sacs, are made up of clusters of alveoli, like individual grapes within a bunch. The individual alveoli are tightly wrapped in blood vessels and it is here that gas exchange actually occurs. Deoxygenated blood from the heart is pumped through the pulmonary artery to the lungs, where oxygen diffuses into blood and is exchanged for carbon dioxide in the haemoglobin of the erythrocytes. The oxygen-rich blood returns to the heart via the pulmonary veins to be pumped back into systemic circulation.

Human lungs are located in two cavities on either side of the heart. Though similar in appearance, the two are not identical. Both are separated into lobes by fissures, with three lobes on the right and two on the left. The lobes are further divided into segments and then into lobules, hexagonal divisions of the lungs that are the smallest subdivision visible to the naked eye. The connective tissue that divides lobules is often blackened in smokers. The medial border of the right lung is nearly vertical, while the left lung contains a cardiac notch. The cardiac notch is a concave impression molded to accommodate the shape of the heart.

Each lobe is surrounded by a pleural cavity, which consists of two pleurae. The parietal pleura lies against the rib cage, and the visceral pleura lies on the surface of the lungs. In between the pleura is pleural fluid. The pleural cavity helps to lubricate the lungs, as well as providing surface tension to keep the lung surface in contact with the rib cage.

Lungs are to a certain extent "overbuilt" and have a tremendous reserve volume as compared to the oxygen exchange requirements when at rest. Such excess capacity is one of the reasons that individuals can smoke for years without having a noticeable decrease in lung function while still or moving slowly; in situations like these only a small portion of the lungs are actually perfused with blood for gas exchange. Destruction of too many alveoli over time leads to the condition emphysema, which is associated with extreme shortness of breath. As oxygen requirements increase due to exercise, a greater volume of the lungs is perfused, allowing the body to match its $CO_2/O_2$ exchange requirements. Additionally, due to the excess capacity, it is possible for humans to live with only one lung, with the one compensating for the other's loss.

The environment of the lung is very moist, which makes it hospitable for bacteria. Many respiratory illnesses are the result of bacterial or viral infection of the lungs. Inflammation of the lungs is known as pneumonia; inflammation of the pleura surrounding the lungs is known as pleurisy.

Vital capacity is the maximum volume of air that a person can exhale after maximum inhalation; it can be measured with a spirometer. In combination with other physiological measurements, the vital capacity can help make a diagnosis of underlying lung disease.

The lung parenchyma is strictly used to refer solely to alveolar tissue with respiratory bronchioles, alveolar ducts and terminal bronchioles. However, it often includes any form of lung tissue, also including bronchioles, bronchi, blood vessels and lung interstitium.

Following gastrulation (embryonic day E7.5 in mice), the definitive endoderm undergoes complex morphogenetic movements that ultimately lead to the formation of the primitive gut tube. The foregut represents the most anterior (cranial) region of this tube, while the midgut and hindgut are located at progressively more posterior regions, towards the caudal end of the embryo (see, e.g., Wells, et al., Annu. Rev. Cell Dev. Biol. 15,393-410). Transcription factor genes such as Foxa1, Foxa2, Gata4 and Gata6, which are expressed early in the endoderm, are crucial for the survival, differentiation and morphogenesis of the foregut (see, e.g., Kuo, et al., Genes Dev. 11, 1048-1060; Morrisey, et al., Genes Dev. 12, 3579-3590; Ang, et al., Cell 78, 561-574; Wan, et al., J. Biol. Chem. 280, 13809-13816). By E8.0-9.5, the local expression of transcription factors along the anteroposterior (AP) axis of the gut endoderm marks organ-specific domains (or fields). For example, the homeodomain protein gene Nkx2.1 [also known as thyroid transcription factor 1 (Titf1) or T/EBP] is expressed in the thyroid and respiratory fields (see, e.g., Kimura, et al., Genes Dev. 10, 60-69), Hex (hematopoietically expressed homeobox) is expressed in the thyroid and liver fields (see, e.g., Martinez Barbera, et al., Development 127, 2433-2445), and the Pdxl (pancreas-duodenal-associated homeobox gene) is expressed in the pancreatic and duodenal fields (see, e.g., Offield, et al., Development 122, 983-995). In addition, morphogenetic movements foster dynamic interactions between the endoderm and neighboring structures, such as the heart, notochord or the septum transversum (the mesodermal cells that give rise to the diaphragm). Exposure of the endoderm to diffusible signals from these structures at crucial developmental windows is essential for endodermal cell fate specification (see, e.g., Kumar and Melton, Curr. Opin. Genet. Dev. 13, 401-407; Bort, et al., Development 131, 797-80).

Fibroblast growth factor 4 (Fgf4), bone morphogenetic protein 2 (Bmp2) and retinoic acid (RA) are among the signals that confer AP identity to the early endoderm. They render the endoderm competent to respond to signals from the adjacent mesoderm or from nearby structures to initiate morphogenesis (see, e.g., Tiso, eta al., Mech. Dev. 118, 29-37; Stafford and Prince, Curr. Biol. 12, 1215-1220; Wells and Melton, Development 127, 1563-1572). In zebrafish, disrupted RA signaling during gastrulation results in the loss of liver and pancreatic (posterior) fates, while thyroid and pharynx (anterior) fates remain unaltered. Conversely, excess RA induces hepatic and pancreatic cell fates at more anterior domains (see, e.g., Stafford and Prince; Curr. Biol. 12, 1215-1220). In mice and rats, RA signaling initiates soon after gastrulation (see, e.g., Rossant, et al., Genes Dev. 5, 1333-1344), but does not seem to be as crucial for foregut AP identity as it is in the zebrafish.

The present invention provides methods for directing the differentiation of definitive endoderm (DE) into lung organoids in vitro.

In some embodiments, PSCs, such as ESCs and iPSCs, undergo directed differentiation in a step-wise manner first into definitive endoderm (DE), then into ventral-anterior foregut spheroid tissue (e.g., SOX2+ anterior foregut 3D spheroid structures), then into 3-dimensional lung tissue, and then into lung organoid tissue.

As such, in some embodiments, methods are provided for the directed differentiation of pluripotent cells (e.g., iPSCs or ESCs) into definitive endoderm, and the obtaining of such definitive endoderm. In some embodiments, methods are provided for the directed differentiation of the obtained definitive endoderm into ventral-anterior foregut spheroid tissue, and obtaining of such ventral-anterior foregut spheroid tissue. In some embodiments, methods are provided for the directed differentiation of the obtained ventral-anterior foregut spheroid tissue into 3-dimensional lung tissue, and the obtaining of such 3-dimensional lung tissue. In some embodiments, methods are provided for the directed differentiation of the obtained 3-dimensional lung tissue into lung organoid tissue, and the obtaining of such lung organoid tissue.

Such methods are not limited to a particular manner of accomplishing the directed differentiation of PSCs into definitive endoderm. Indeed, any method for producing definitive endoderm from pluripotent cells (e.g., iPSCs or ESCs) is applicable to the methods described herein. In some embodiments, pluripotent cells are derived from a morula. In some embodiments, pluripotent stem cells are stem cells. Stem cells used in these methods can include, but are not limited to, embryonic stem cells. Embryonic stem cells can be derived from the embryonic inner cell mass or from the embryonic gonadal ridges. Embryonic stem cells or germ cells can originate from a variety of animal species including, but not limited to, various mammalian species including humans. In some embodiments, human embryonic stem cells are used to produce definitive endoderm. In some embodiments, human embryonic germ cells are used to produce definitive endoderm. In some embodiments, iPSCs are used to produce definitive endoderm.

In some embodiments, one or more growth factors are used in the differentiation process from pluripotent stem cells to DE cells. The one or more growth factors used in the differentiation process can include growth factors from the TGF-β superfamily. In such embodiments, the one or more growth factors comprise the Nodal/Activin and/or the BMP subgroups of the TGF-β superfamily of growth factors. In some embodiments, the one or more growth factors are selected from the group consisting of Nodal, Activin A, Activin B, BMP4, Wnt3a or combinations of any of these growth factors.

In some embodiments, the embryonic stem cells or germ cells and iPSCs are treated with the one or more growth factors for 6 or more hours; 12 or more hours; 18 or more hours; 24 or more hours; 36 or more hours; 48 or more hours; 60 or more hours; 72 or more hours; 84 or more hours; 96 or more hours; 120 or more hours; 150 or more hours; 180 or more hours; or 240 or more hours.

In some embodiments, the embryonic stem cells or germ cells and iPSCs are treated with the one or more growth factors at a concentration of 10 ng/ml or higher; 20 ng/ml or higher; 50 ng/ml or higher; 75 ng/ml or higher; 100 ng/ml or higher; 120 ng/ml or higher; 150 ng/ml or higher; 200 ng/ml or higher; 500 ng/ml or higher; 1,000 ng/ml or higher; 1,200 ng/ml or higher; 1,500 ng/ml or higher; 2,000 ng/ml or higher; 5,000 ng/ml or higher; 7,000 ng/ml or higher; 10,000 ng/ml or higher; or 15,000 ng/ml or higher. In some embodiments, concentration of the growth factor is maintained at a constant level throughout the treatment. In other embodiments, concentration of the growth factor is varied during the course of the treatment. In some embodiments, the growth factor is suspended in media that include fetal bovine serine (FBS) with varying HyClone concentrations. One of skill in the art would understand that the regimen described herein is applicable to any known growth factors, alone or in combination. When two or more growth factors are used, the concentration of each growth factor may be varied independently.

In some embodiments, populations of cells enriched in definitive endoderm cells are used. In some embodiments, the definitive endoderm cells are isolated or substantially purified. In some embodiments, the isolated or substantially purified definitive endoderm cells express the SOX2+ marker.

Methods for enriching a cell population with definitive endoderm are also contemplated. In some embodiments, definitive endoderm cells can be isolated or substantially purified from a mixed cell population by contacting the cells with a reagent that binds to a molecule that is present on the surface of definitive endoderm cells but which is not present on the surface of other cells in the mixed cell population, and then isolating the cells bound to the reagent.

Additional methods for obtaining or creating DE cells that can be used in the present invention include but are not limited to those described in U.S. Pat. Nos. 7,510,876; 7,326,572; Kubol et al., 2004, Development 131:1651-1662; D'Amour et al., 2005, Nature Biotechnology 23:1534-1541; and Ang et al., 1993, Development 119:1301-1315.

In some embodiments, directed differentiation toward ventral-anterior foregut spheroid tissue, 3-dimensional lung tissue, and lung organoid tissue is achieved by selectively activating or inhibiting certain signaling pathways in the iPSCs and/or DE cells. In some embodiments, the activated and/or inhibited signaling pathways are those active in lung development, including but not limited to the BMP signaling pathway, the TGFβ signaling pathway, the Wnt signaling pathway, the FGF signaling pathway, and the Hedgehog signaling pathway in a step-wise manner.

In some embodiments, directed differentiation of definitive endoderm into lung organoid tissue is accomplished first through directed differentiation of definitive endoderm into ventral-anterior foregut spheroid tissue, then directed differentiation of the ventral-anterior foregut spheroid tissue into 3-dimensional lung tissue, and then directed differentiation of the 3-dimensional lung tissue into lung organoid tissue.

Such techniques are not limited to a particular manner of inducing formation of ventral-anterior foregut spheroid tissue from definitive endoderm. In some embodiments, inducing formation of ventral-anterior foregut spheroid tissue from definitive endoderm is accomplished through selectively activating the Wnt signaling pathway and the FGF signaling pathway, and inhibiting the BMP signaling pathway, and the TGFβ signaling pathway in the DE cells. In some embodiments, activating and/or inhibiting one or more signaling pathways within the definitive endoderm cells comprises culturing the definitive endoderm cells with a Wnt signaling pathway agonist, a FGF signaling pathway agonist, a BMP signaling pathway inhibitor, and a TGFβ signaling pathway inhibitor. In some embodiments, activating and/or inhibiting one or more signaling pathways within the definitive endoderm cells comprises culturing the definitive endoderm cells with CHIR99021, FGF4, Noggin, and SB431542.

Such techniques are not limited to a particular manner of inducing formation of 3-dimensional lung tissue from the ventral-anterior foregut spheroid tissue. In some embodiments, inducing formation of 3-dimensional lung tissue from the ventral-anterior foregut spheroid tissue occurs through activating the Hedgehog signaling pathway within the ventral-anterior foregut spheroid tissue. Such methods are not limited to a particular manner of activating the Hedgehog signaling pathway within the obtained ventral-anterior foregut spheroid tissue. In some embodiments, culturing the obtained ventral-anterior foregut spheroid tissue occurs through activating the Hedgehog signaling pathway occurs through culturing the obtained ventral-anterior foregut spheroid tissue with a small molecule or agonist that activates the Hedgehog signaling pathway. In some embodiments, the small molecule or agonist that activates the Hedgehog signaling pathway is smoothened agonist (SAG).

Such techniques are not limited to a particular manner of inducing formation of lung organoid tissue from the 3-dimensional lung tissue. In some embodiments, inducing formation of lung organoid tissue from the 3-dimensional lung tissue occurs through activating the FGF pathway within the 3-dimensional lung tissue. Such methods are not limited to a particular manner of activating the FGF signaling pathway within the obtained 3-dimensional lung tissue. In some embodiments, culturing the obtained 3-dimensional lung tissue through activating the FGF signaling pathway occurs through culturing the obtained 3-dimensional lung tissue with a small molecule or agonist that activates the FGF signaling pathway. In some embodiments, the small molecule or agonist that activates the FGF signaling pathway is selected from FGF1, FGF2, FGF3, FGF4, FGF10, FGF11, FGF12, FGF13, FGF14, FGF15, FGF16, FGF17, FGF18, FGF19, FGF20, FGF21, FGF22, and FGF23. In some embodiments, the small molecule or agonist that activates the FGF signaling pathway is FGF10.

In some embodiments, the obtained lung organoid tissue comprises upper airway-like epithelium with basal cells, immature ciliated cells surrounded by smooth muscle and myofibroblasts, and/or alveolar-like cells.

In some embodiments, selective inhibiting of the BMP signaling pathway is accomplished with a small molecule or antagonist that inhibits the BMP signaling pathway. BMPs bind as a dimeric ligand to a receptor complex consisting of two different receptor serine/threonine kinases, type I and type II receptors. The type II receptor phosphorylates the type I receptor, resulting in the activation of this receptor kinase. The type I receptor subsequently phosphorylates specific receptor substrates (SMAD), resulting in a signal transduction pathway leading to transcriptional activity.

A BMP inhibitor (e.g., a small molecule or antagonist that inhibits the BMP signaling pathway) is defined as an agent that binds to a BMP molecule to form a complex wherein the BMP activity is neutralized, for example by preventing or inhibiting the binding of the BMP molecule to a BMP receptor. Alternatively, said inhibitor is an agent that acts as an antagonist or reverse agonist. This type of inhibitor binds with a BMP receptor and prevents binding of a BMP to said receptor. An example of a latter agent is an antibody that binds a BMP receptor and prevents binding of BMP to the antibody-bound receptor.

A BMP inhibitor may be added to iPSCs and/or DE cells for purposes of directed differentiation of such cells toward lung organoids. In some embodiments, the amount of BMP inhibitor added to iPSCs and/or DE cells for purposes of directed differentiation of such cells toward lung organoids is any amount effective to inhibit a BMP-dependent activity in such cells to at most 90%, more preferred at most 80%, more preferred at most 70%, more preferred at most 50%, more preferred at most 30%, more preferred at most 10%, more preferred 0%, relative to a level of a BMP activity in the absence of said inhibitor, as assessed in the same cell type. As is known to a skilled person, a BMP activity can be determined by measuring the transcriptional activity of BMP, for example as exemplified in Zilberberg et al., 2007. BMC Cell Biol. 8:41.

Several classes of natural BMP-binding proteins are known, including Noggin (Peprotech), Chordin and chordin-like proteins (R&D systems) comprising chordin domains, Follistatin and follistatin-related proteins (R&D systems) comprising a follistatin domain, DAN and DAN-like proteins (R&D systems) comprising a DAN cysteine-knot domain, sclerostin/SOST (R&D systems), decorin (R&D systems), and alpha-2 macroglobulin (R&D systems).

In some embodiments, the BMP inhibitor is Noggin ("Nog"). In some embodiments, the amount of Noggin added to the iPSCs and/or DE cells for purposes of directed differentiation of such cells toward lung organoids is, for example, at a concentration of at least 10 ng/ml, more preferred at least 20 ng/ml, more preferred at least 50 ng/ml, more preferred at least 100 ng/ml. A still more preferred concentration is approximately 100 ng/ml or exactly 100 ng/ml.

In some embodiments, selective activation of the Wnt signaling pathway is accomplished with a Wnt agonist ("W").

The Wnt signalling pathway is defined by a series of events that occur when a Wnt protein binds to a cell-surface receptor of a Frizzled receptor family member. This results in the activation of Dishevelled family proteins which inhibit a complex of proteins that includes axin, GSK-3, and the protein APC to degrade intracellular β-catenin. The resulting enriched nuclear β-catenin enhances transcription by TCF/LEF family transcription factors.

A Wnt agonist (e.g., a small molecule or agonist that activates the Wnt signaling pathway) is defined as an agent that activates TCF/LEF-mediated transcription in a cell. Wnt agonists are therefore selected from true Wnt agonists that bind and activate a Frizzled receptor family member including any and all of the Wnt family proteins, an inhibitor of intracellular β-catenin degradation, and activators of TCF/LEF. Said Wnt agonist is added to the iPSCs and/or DE cells for purposes of directed differentiation of such cells toward lung organoids in an amount effective to stimulate a Wnt activity in a cell by at least 10%, more preferred at least 20%, more preferred at least 30%, more preferred at least 50%, more preferred at least 70%, more preferred at least 90%, more preferred at least 100%, relative to a level of said Wnt activity in the absence of said molecule, as assessed in the same cell type. As is known to a skilled person, a Wnt activity can be determined by measuring the transcriptional activity of Wnt, for example by pTOPFLASH and pFOP-FLASH Tcfluciferase reporter constructs (see, e.g., Korinek et al., 1997. Science 275:1784-1787).

A Wnt agonist may comprise a secreted glycoprotein including Wnt-1/Int-1; Wnt-2/Irp (Int-1-related Protein); Wnt-2b/13; Wnt-3/Int-4; Wnt-3a (R&D systems); Wnt-4; Wnt-5a; Wnt-5b; Wnt-6 (Kirikoshi H et al. 2001. Biochem Biophys Res Com 283: 798-805); Wnt-7a (R&D systems); Wnt-7b; Wnt-8a/8d; Wnt-8b; Wnt-9a/14; Wnt-9b/14b/15; Wnt-10a; Wnt-10b/12; Wnt-11; and Wnt-16. An overview of human Wnt proteins is provided in "THE WNT FAMILY OF SECRETED PROTEINS", R&D Systems Catalog, 2004.

Further Wnt agonists include the R-spondin family of secreted proteins, which is implicated in the activation and regulation of Wnt signaling pathway and which is comprised of 4 members (R-spondin 1 (NU206, Nuvelo, San Carlos, Calif.), R-spondin 2 ((R&D systems), R-spondin 3, and R-spondin-4); and Norrin (also called Norrie Disease Protein or NDP) (R&D systems), which is a secreted regulatory protein that functions like a Wnt protein in that it binds with high affinity to the Frizzled-4 receptor and induces activation of the Wnt signaling pathway (Kestutis Planutis et al. (2007) BMC Cell Biol. 8: 12).

Compounds that mimic the activity of R-spondin may be used as Wnt agonists of the invention. It has recently been found that R-spondin interacts with Lgr5. Thus, Lgr5 agonists such as agonistic anti-Lgr5 antibodies are examples of Wnt agonists that may be used in the invention.

A small-molecule agonist of the Wnt signaling pathway, an aminopyrimidine derivative, was identified and is also expressly included as a Wnt agonist (Liu et al. (2005) Angew Chem Int Ed Engl. 44, 1987-90).

Known GSK-inhibitors comprise small-interfering RNAs (siRNA; Cell Signaling), lithium (Sigma), kenpaullone (Biomol International; Leost, M. et al. (2000) Eur. J. Biochem. 267, 5983-5994), 6-Bromoindirubin-30-acetoxime (Meijer, L. et al. (2003) Chem. Biol. 10, 1255-1266), SB 216763 and SB 415286 (Sigma-Aldrich), and FRAT-family members and FRAT-derived peptides that prevent interaction of GSK-3 with axin. An overview is provided by Meijer et al., (2004) Trends in Pharmacological Sciences 25, 471-480. Methods and assays for determining a level of GSK-3 inhibition are known to a skilled person and comprise, for example, the methods and assay as described in Liao et al 2004, Endocrinology, 145(6): 2941-9.

In some embodiments the Wnt agonist is a Gsk3 inhibitor. In some embodiments, the Gsk3 inhibitor is selected from the group consisting of CHIR 99021, CHIR 98014, BIO-acetoxime, BIO, LiCl, SB 216763, SB 415286, AR A014418, 1-Azakenpaullone, and Bis-7-indolylmaleimide.

In some embodiments the Gsk3 inhibitor is CHIR 99021 or CHIR 98014 at a concentration of at least about 4 μM to about 10 μM i. In some embodiments the Gsk3 inhibitor comprises an RNAi targeted against Gsk3.

In some embodiments, the Wnt agonist added to the iPSCs and/or DE cells for purposes of directed differentiation of such cells toward lung organoids is CHIR 99021. In some embodiments, CHIR 99021 is preferably added to the iPSCs and/or DE cells for purposes of directed differentiation of such cells toward lung organoids at a concentration of at least 200

In some embodiments, selective activation of the FGF signaling pathway is accomplished with a FGF agonist ("F") (e.g., a small molecule or agonist that activates the FGF signaling pathway).

In some embodiments, the FGF agonist added to the iPSCs and/or DE cells for purposes of directed differentiation of such cells toward lung organoids is able to bind to FGFR2 or FGFR4. An FGF able to bind to FGFR2 (FGF receptor) or FGFR4 is preferably FGF4, FGF7 or FGF10, most preferably FGF10.

FGF10 is a protein that belongs to the fibroblast growth factor (FGF) family of proteins. FGF family members possess broad mitogenic and cell survival activities, and are involved in a variety of biological processes, including embryonic development, cell growth, morphogenesis, tissue repair, tumor growth and invasion. FGFs stimulate cells by interacting with cell surface tyrosine kinase receptors (FGFR). Four closely related receptors (FGFR1-FGFR4) have been identified. FGFR1-FGFR3 genes have been shown to encode multiple isoforms, and these isoforms can be critical in determining ligand specificity. Most FGFs bind more than one receptor (Ornitz J Biol. Chem. 1998 Feb. 27; 273 (9):5349-57). However, FGF10 and FGF7 are unique among FGFs in that they interact only with a specific isoform of FGFR2, designated FGFR2b which is expressed exclusively by epithelial cells (Igarashi, J Biol. Chem. 1998 273(21):13230-5). FGF10 is a preferred FGF able to bind to FGFR2 or FGFR4.

Preferred concentrations for FGF10 are 20, 50, 100, 500 ng/ml, not higher than 500 ng/ml. FGF (e.g., FGF10) is preferably added to the iPSCs and/or DE cells for purposes of directed differentiation of such cells toward lung organoids when required.

TGF-β signaling pathway is used to describe the downstream signaling events attributed to TGF-β and TGF-β like ligands. For example, in one signaling pathway a TGF-β ligand binds to and activates a Type II TGF-β receptor. The Type II TGF-β receptor recruits and forms a heterodimer with a Type I TGF-β receptor. The resulting heterodimer permits phosphorylation of the Type I receptor, which in turn phosphorylates and activates a member of the SMAD family of proteins. A signaling cascade is triggered, which is well known to those of skill in the art, and ultimately leads to control of the expression of mediators involved in cell growth, cell differentiation, tumorigenesis, apoptosis, and cellular homeostasis, among others. Other TGF-β signaling pathways are also contemplated for manipulation according to the methods described herein.

A TGF-β inhibitor (e.g., a small molecule or antagonist that inhibits the TGF-β signaling pathway) refers to inhibition of at least one of the proteins involved in the signal transduction pathway for TGF-β. It is contemplated herein that an inhibitor of the TGF-β signaling pathway can be, for example, a TGF-β receptor inhibitor (e.g., a small molecule, an antibody, an siRNA), a TGF-β sequestrant (e.g., an antibody, a binding protein), an inhibitor of receptor phosphorylation, an inhibitor of a SMAD protein, or a combination of such agents.

In some embodiments, a TGF-β inhibitor such as SB431542 (SB) is additionally added to the iPSCs and/or DE cells for purposes of directed differentiation of such cells toward lung organoids.

In some embodiments, the TGF-β signaling pathway inhibitor comprises or consists essentially of a TGF-β receptor inhibitor. One of skill in the art can easily test a compound to determine if it inhibits TGF-β receptor signaling by assessing, for example, phosphorylation status of the receptor or expression of downstream proteins controlled by TGF-β in cultured cells and comparing the results to cells not treated with a TGF-β receptor inhibitor. An agent is determined to be a TGF-β signaling pathway inhibitor if the level of phosphorylation of the Type I TGF-β receptor in a culture of cells is reduced by at least 20% compared to the level of phosphorylation of the Type I TGF-β receptor in cells that are cultured in the absence of a TGF-β signaling pathway inhibitor; preferably the level of phosphorylation is reduced by at least 30%, at least 40%, at least 50%, at least 60%, at least 70%, at least 80%, at least 90%, at least 95%, at least 99%, or even 100% (no phosphorylation) in the presence of a TGF-β signaling pathway inhibitor.

In some embodiments, a Hedgehog signaling pathway agonist (e.g., a small molecule or agonist that activates the Hedgehog signaling pathway) is additionally added to the iPSCs and/or DE cells for purposes of directed differentiation of such cells toward lung organoids. In some embodiments, the hedgehog signaling pathway agonist is any compound that activates the hedgehog receptor. In some embodiments, the hedgehog signaling pathway agonist is smoothened agonist (SAG).

In some embodiments, ventral-anterior foregut spheroid tissue and/or 3-dimensional lung tissue and/or lung organoid tissue produced in vitro from the described methods can be used to screen drugs for lung tissue uptake and mechanisms of transport. For example, this can be done in a high throughput manner to screen for the most readily absorbed drugs, and can augment Phase 1 clinical trials that are done to study drug lung tissue uptake and lung tissue toxicity. This includes pericellular and intracellular transport mechanisms of small molecules, peptides, metabolites, salts.

In some embodiments, ventral-anterior foregut spheroid tissue and/or 3-dimensional lung tissue and/or lung organoid tissue produced in vitro from the described methods can be used to identify the molecular basis of normal human lung development.

In some embodiments, ventral-anterior foregut spheroid tissue and/or 3-dimensional lung tissue and/or lung organoid tissue produced in vitro from the described methods can be used to identify the molecular basis of congenital defects affecting human lung development.

In some embodiments, 3 ventral-anterior foregut spheroid tissue and/or 3-dimensional lung tissue and/or lung organoid tissue produced in vitro from the described methods can be used to correct lung related congenital defects caused by genetic mutations. In particular, mutation affecting human lung development can be corrected using iPSC technology and genetically normal ventral-anterior foregut spheroid tissue and/or 3-dimensional lung tissue and/or lung organoid tissue produced in vitro from the described methods. In some embodiments, ventral-anterior foregut spheroid tissue and/or 3-dimensional lung tissue and/or lung organoid tissue produced in vitro from the described methods can be used to generate replacement tissue.

In some embodiments, ventral-anterior foregut spheroid tissue and/or 3-dimensional lung tissue and/or lung organoid tissue produced in vitro from the described methods can be used to generate replacement lung tissue for lung related disorders.

In some embodiments, a diagnostic kit or package is developed to include ventral-anterior foregut spheroid tissue and/or 3-dimensional lung tissue and/or lung organoid tissue produced in vitro from the described methods and based on one or more of the aforementioned utilities.

EXAMPLES

The following examples are illustrative, but not limiting, of the compounds, compositions, and methods of the present invention. Other suitable modifications and adaptations of the variety of conditions and parameters normally encountered in clinical therapy and which are obvious to those skilled in the art are within the spirit and scope of the invention.

Example 1

This example describes differentiation of hPSCs into anterior foregut spheroids.

Efficient induction of human endoderm using ActivinA has been described (see, e.g., Spence J R, et al., Nature. 2011 Feb. 3; 470(7332):105-9; D'Amour K A, et al., Nat Biotechnol. 2005 Oct. 28; 23(12):1534-41; Zhang M, et al., Histochem. Cell Biol. 2010 October; 134(4):327-35), and a further lineage restriction into SOX2+ anterior foregut endoderm using inhibition of BMP and TGFβ signaling has been described (see, e.g., Green M D, et al., Nat Biotechnol. Nature Publishing Group; 2011 Feb. 27:1-7; Loh K M, et al., Cell Stem Cell. 2014 Feb. 6; 14(2):237-52). It has been demonstrated that inhibition of BMP signaling during intestinal lineage induction with WNT and FGF ligands is sufficient to inhibit intestinal CDX2 and induce SOX2+ posterior foregut spheroids capable of giving rise to human gastric (antral) organoids (see, e.g., McCracken K W, et al., Nature; 2014 Oct. 29:1-19). Given that the lung is derived from the anterior foregut, experiments were conducted to define conditions to generate ventral anterior foregut spheroids. To do this, tests were conducted to determine if dual inhibition of BMP and TGFβ was able to anteriorize cultures, as previously described (see, e.g., Green M D, et al., Nat Biotechnol; 2011 Feb. 27:1-7). hESCs were treated with ActivinA (100 ng/mL) for four days to induce endoderm, followed by four days of Noggin (NOG, 200 ng/mL) and the small molecule TGFβ inhibitor, SB431542 (SB, 10 μM). It was confirmed that these conditions were able to induce robust mRNA and protein expression of SOX2, which co-expressed with endodermal marker FOXA2, while repressing the intestinal lineage marker CDX2 (see, FIG. 1A-C, FIG. 2A). QRT-PCR analysis also showed that compared to controls (in which endoderm was induced but was not exposed to NOG/SB), exposure to NOG/SB robustly induced ventral anterior foregut genes NKX2.1 and PAX8, while the posterior foregut transcript, PDX1 was reduced. HHEX, which is expressed in the developing liver, biliary system and thyroid, but is absent from the lung primordium, remained unchanged (see, FIG. 1B). Given that NKX2.1 is expressed in the lung and thyroid primordium, and PAX8 is expressed in the thyroid primordium, these results suggest that 4 day ActivinA treatment followed by a 4 day NOG/SB treatment biases the cultures towards ventral-anterior foregut lineages.

Figure 3A:
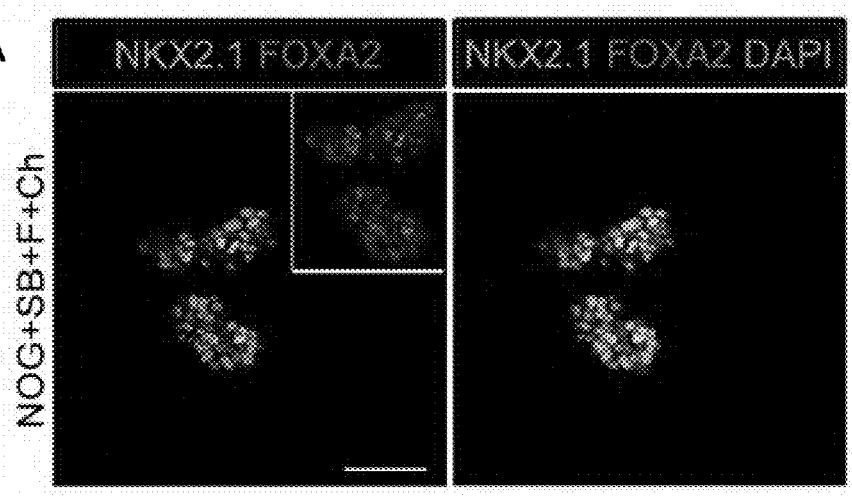
FIG. 3A-B: Foregut spheroids co-express endoderm and lung specific markers. (A) NOG/SB/FGF4/Ch spheroids have weak NKX2.1 (gray-scaled green) expression which co-expresses with endoderm marker FOXA2 (gray-scaled red). (B) The majority of cells in the spheroid express SOX2 (gray-scaled green) and co-stain with FOXA2 (gray-scaled red). Scale bars represent 50 µM.
Figure 3B:
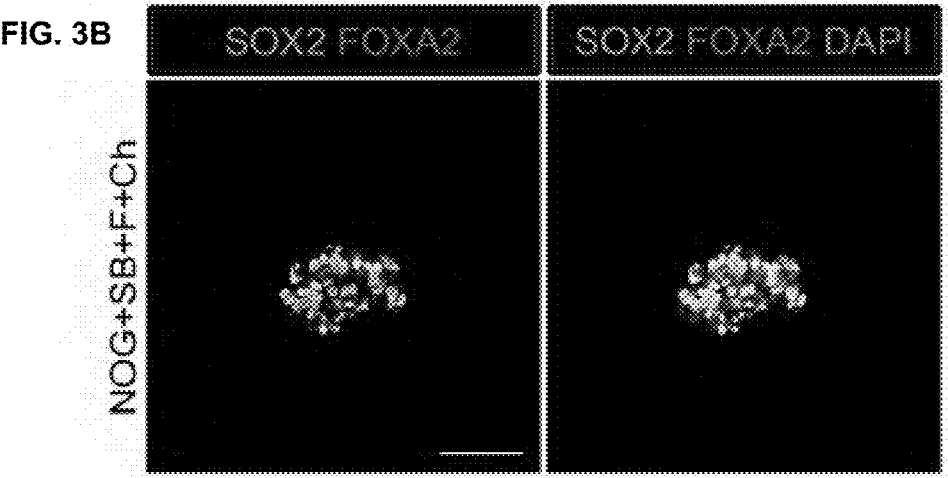
Figure 4:
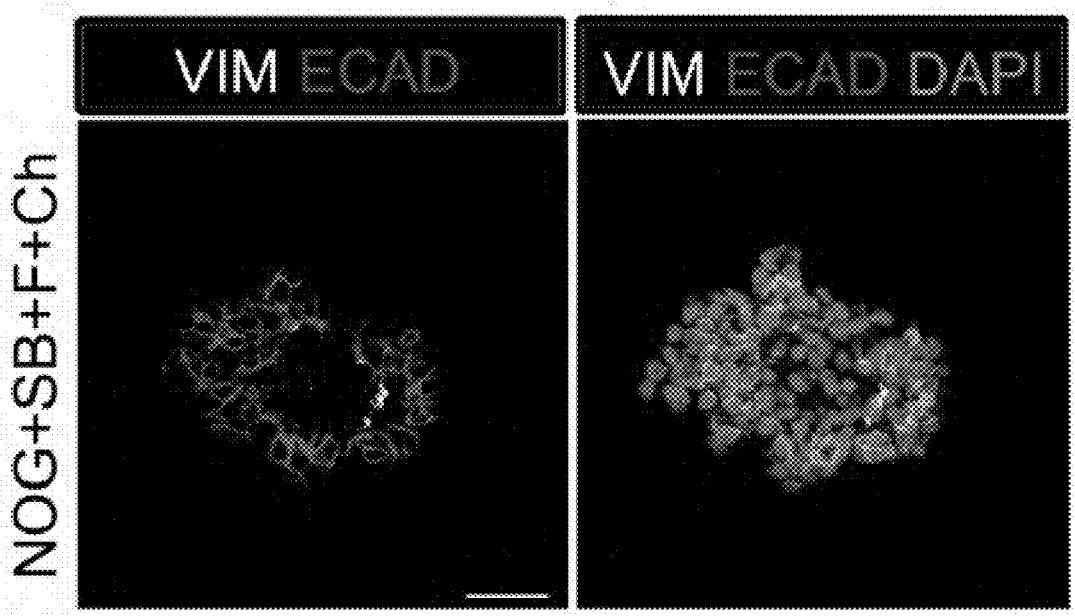
FIG. 4: Foregut spheroids consist of both epithelial and mesenchymal cells. NOG/SB/FGF4/Ch spheroids have a minor population of Vimentin (VIM, white) positive mesenchymal cells, while the majority of cells are epithelial and express ECAD (gray-scaled red). Scale bar represents 50 µM.
Figure 5:
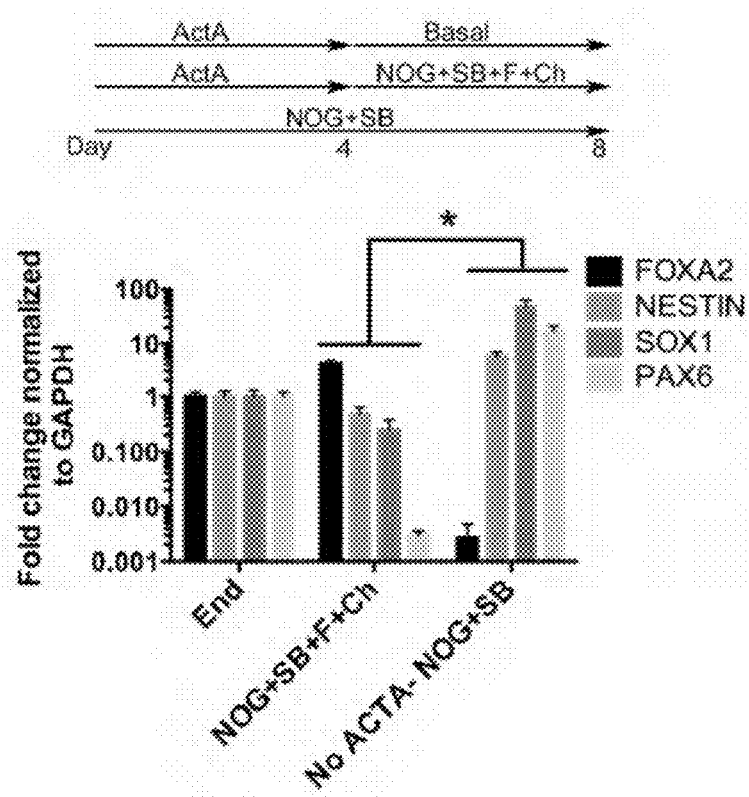
FIG. 5: NOG+SB+FGF4+Ch spheroids do not express neural markers. hESCs were differentiated into endoderm by treating with 4 days of ActivinA (ACTA) and spheroids were generated with an additional 4 days of NOG+SB+FGF4+Ch. Neural cultures were not treated with ACTA, but were treated with NOG+SB for 8 days. Compared to foregut spheroids (NOG+SB+FGF4+Ch), NOG+SB neural cultures had a significant increase in neural markers NESTIN, SOX1, and PAX6 and significant decrease in FOXA2, which is highly expressed in endoderm. *p<0.05, error bars represent SEM.

Addition of FGF4 plus WNT3A (or Chir99021, a GSK3β inhibitor that enhances β-catenin dependent WNT signaling) promotes CDX2 intestinal lineage commitment and 3D spheroid formation in endoderm cultures (see, e.g., Spence J R, et al., Nature. 2011 Feb. 3; 470(7332):105-9; Green M D, et al., Nature; 2011 Feb. 27; 1-7; Loh K M, et al., Cell Stem Cell. 2014 Feb. 6; 14(2):237-52; Xue X, et al., Gastroenterology. 2013 Jul. 13). Based on the results in FIG. 1B-C, it was hypothesized that combining FGF, Chir99021, NOG and SB would result in the generation of SOX2+ ventral-anterior foregut spheroids. To test this, endoderm was generated (4 days ACTA) and either no growth factors were added (Endoderm controls) or NOG, SB, FGF4, and Chir99021 (NOG/SB/F/Ch) added (FIG. 1D). Addition of all four factors resulted in the generation of 3-dimensional SOX2+, CDX2- spheroids (FIG. 1E, F). SOX2+ spheroids also expressed the endodermal protein FOXA2, and were epithelial, co-expressing E-Cadherin (ECAD) (FIG. 1F, FIG. 3). In addition to SOX2, spheroids exhibited higher mRNA expression of anterior foregut lineage markers NKX2.1 and PAX8 compared to endoderm controls, suggesting that they are ventral-anterior foregut spheroids (FIG. 1E), however, immunofluorescence revealed that levels of NKX2.1 protein were just above the detection threshold (FIG. 3). Spheroids also possess a minor population of cells that are mesodermal in origin staining positive for Vimentin protein (VIM) (FIG. 4). Given that neural tissues also express NKX2.1, PAX8, SOX2, and FOXA2, and that neural induction protocols use dual BMP and TGFβ inhibition, it was intended to exclude the possibility that spheroids were neural in nature. To do this, endoderm control cultures, foregut spheroids (ActivinA followed by NOG/SB/F/Ch), and induced neural tissue were generated by adding NOG/SB to hESC cultures that were not treated with ActivinA (see, e.g., Chambers S M, et al., Nat Biotechnol. 2009 Mar. 1; 27(3):275-80). By examining induction of the neural markers NESTIN, SOX1, and PAX6, it was confirmed that these transcripts were highly induced in dual NOG/SB neural cultures, but were low in ventral foregut spheroid cultures. In contrast, FOXA2, which is expressed in the foregut (see, e.g., Monaghan A P, et al., Development. 1993 November; 119(3):567-78; Ang S L, et al., Cell. 1994 Aug. 26; 78(4):561-74) and in some neural tissues (see, e.g., Spence J R, et al., Nature. 2011 Feb. 3; 470(7332):105-9; Kroon E, et al., Nat Biotechnol. 2008 Feb. 20; 26(4):443-52; Si-Tayeb K, et al., Hepatology. 2009 Oct. 1; 51(1):297-305; D'Amour K A, et al., Nat Biotechnol [Internet]. 2005 Oct. 28; 23(12):1534-41; Stott S R W, et al., Journal of Neuroscience. 2013 May 1; 33(18):8022-34; D'Amour K A, et al., Nat Biotechnol. 2006 November; 24(11):1392-401; DeLaForest A, et al., Development. 2011 October; 138(19):4143-53), had high expression in ventral foregut spheroids, but was significantly reduced in dual NOG/SB neural conditions (FIG. 5). Taken together, these results strongly suggest spheroids are indeed foregut, and not of neural origin.

Example II

This example shows induction of anterior foregut endoderm into a lung lineage through modulation of FGF and HH signaling.

Figure 1B:
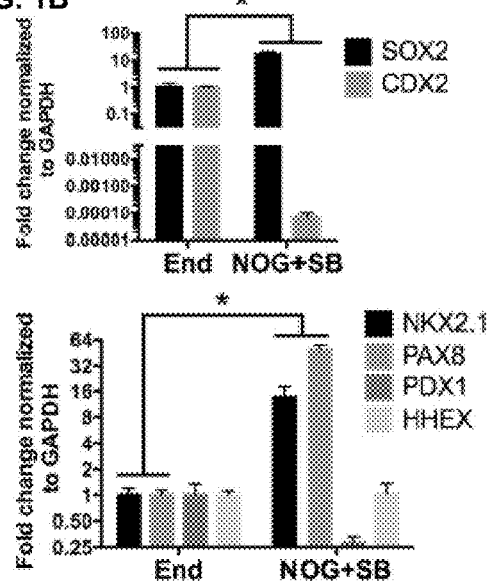
Figure 1C:
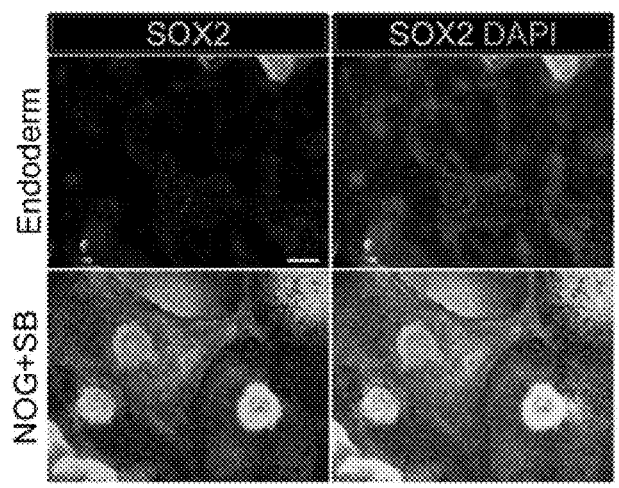

Many signaling pathways are important for lung induction and development (see, e.g., Wong A P, et al., Nat Biotechnol. 2012 Aug. 26; Huang S X L, et al., Nature; 2013 Dec. 1; 1-11; Firth A L, et al., Proceedings of the National Academy of Sciences. 2014 Apr. 29; 111(17):E1723-30; Mou H, et al., Cell Stem Cell. 2012 Apr. 6; 10(4):385-97; Ghaedi M, et al., J. Clin. Invest. 2013 Nov. 1; 123(11):4950-62; Longmire T A, et al., Cell Stem Cell. 2012 Apr. 6; 10(4):398-411; Rankin S A, Zorn A M. Gene Regulatory Networks Governing Lung Specification. J Cell Biochem. 2014 Mar. 19; Morrisey E E, et al., Developmental Cell. Elsevier Inc; 2010 Jan. 19; 18(1):8-23; Min H, et al., Genes & Development. 1998 Oct. 15; 12(20):3156-61; Weaver M, et al., Development. 2000 June; 127(12):2695-704). High levels of Fgf signaling have been shown to induce Shh and Nkx2.1 expression in the foregut endoderm in mice (see, e.g., Spence J R, et al., Nature. 2011 Feb. 3; 470(7332):105-9; D'Amour K A, et al., Nat Biotechnol. 2005 Oct. 28; 23(12):1534-41; Lancaster M A, et al., Nature. 2013 Sep. 19; 501(7467):373-9; Takebe T, et al., Nature. 2013 Jul. 25; 499(7459):481-4; Nakano T, et al., Cell Stem Cell. 2012 Jun. 14; 10(6):771-85; Meyer J S, et al., Stem Cells. 2011 August; 29(8):1206-18; Hebrok M, et al., Genes & Development. 1998; Serls A E.; Development. 2004 Dec. 2; 132(1):35-47); furthermore, Gli2/3 null mouse embryos fail to form lungs (see, e.g., Spence J R, et al., Nature. 2011 Feb. 3; 470(7332):105-9; Wells J M, et al., Development. 2014 February; 141(4):752-60; Motoyama J, et al., Nat Genet. 1998 September; 20(1):54-7) and Hh signaling is important for lung mesenchyme proliferation in vivo (see, e.g., Bellusci S, et al., Development. 1997 January; 124(1):53-63). These data confirm that Fgf and Hh signaling are critical for lung specification and ligands from both signaling pathways have been applied to hPSC derived lung lineages in 2D cultures (see, e.g., Spence J R, et al., Nature. 2011 Feb. 3; 470(7332):105-9; Wong A P, et al., Nat Biotechnol. 2012 Aug. 26; Huang S X L, et al., Nat Biotechnol; 2013 Dec. 1; 1-11). It has been reported that approximately 85-95% of cells are endoderm, but a portion of the remaining cells are mesodermal and this small mesodermal population is maintained in the spheroids and organoids (see, e.g., Spence J R, et al., Nature. 2011 Feb. 3; 470(7332):105-9; McCracken K W, et al., Nature; 2014 Oct. 29; 1-19; Green M D, et al., Nat Biotechnol.; 2011 Feb. 27; 1-7) (FIG. 4). Therefore, based on mouse and hPSC studies, it was hypothesized that FGF and/or HH signaling would induce an NKX2.1+ lung lineage in anterior foregut endoderm. To test this hypothesis experiments initially focused on adherent endoderm monolayer cultures to optimize induction conditions. Cultures were treated for 4 days with ActivinA followed by an additional 4 days with NOG/SB (referred to as Foregut). Controls consisted of ActivinA treatment only followed by no additional growth factors (Endoderm controls), or ActivinA followed by NOG/SB, followed by no additional factors (Foregut controls). All experimental groups were compared to both endoderm and foregut controls (FIG. 6). The ability of FGF2 to induce SHH, NKX2.1 and PAX8 was first tested by exposing foregut cultures to low and high concentrations of FGF2 (50,500 ng/mL) (FIG. 6A). A robust concentration dependent increase in SHH and PAX8 mRNA expression compared to foregut or endoderm controls was observed, and a modest increase of NKX2.1 expression at the highest dose of FGF2 (500 ng/mL) (FIG. 6A). It was also observed that dual NOG/SB inhibition in endoderm cultures induced robust NKX2.1 and PAX8 expression without adding FGF2 (FIG. 1B, 6A). Thus, it was desired to determine if NKX2.1 expression in foregut cultures was due to endogenous FGF and/or HH signaling. To test this, the FGF or HH pathway was inhibited with small molecules SU5402 (SU, 10 µm) and Sant-2 (10 µm) respectively (FIG. 6B-C). Treating foregut cultures with the FGF inhibitor SU caused a significant, robust reduction in PAX8 and a modest reduction in SHH, while NKX2.1 expression was unchanged compared to foregut control (FIG. 6B). Conversely, inhibition of HH signaling caused a significant reduction in NKX2.1 expression, but not PAX8 compared to untreated foregut. When FGF2 was added to the cultures, a modest increase in NKX2.1 expression was observed, and when FGF was added along with Sant-2, NKX2.1 expression was significantly reduced (FIG. 6C). Together these results suggest a hierarchy where FGF is upstream of SHH and PAX8, and where SHH is upstream of NKX2.1. To test if HH signaling was able to induce NKX2.1 in foregut cultures, the Smoothened agonist, SAG (1 µM), was added to foregut cultures. The addition of SAG induced a 6.5 fold increase of NKX2.1 expression above foregut controls (FIG. 6D). However, SAG alone did not reduce PAX8 expression.

Based on these results, it was further hypothesized that enhancing HH signaling would result in increased NKX2.1 expression downstream of FGF, and that simultaneous inhibition of FGF signaling would reduce PAX8 expression; therefore, endogenous FGF signaling was inhibited with SU while activating HH with SAG (FIG. 6D). This combination caused an additional increase in NKX2.1 expression (21 fold vs. 6.5 fold with SAG only, when compared to foregut) and a concomitant decrease in PAX8 mRNA (FIG. 6D).

Figure 2A:
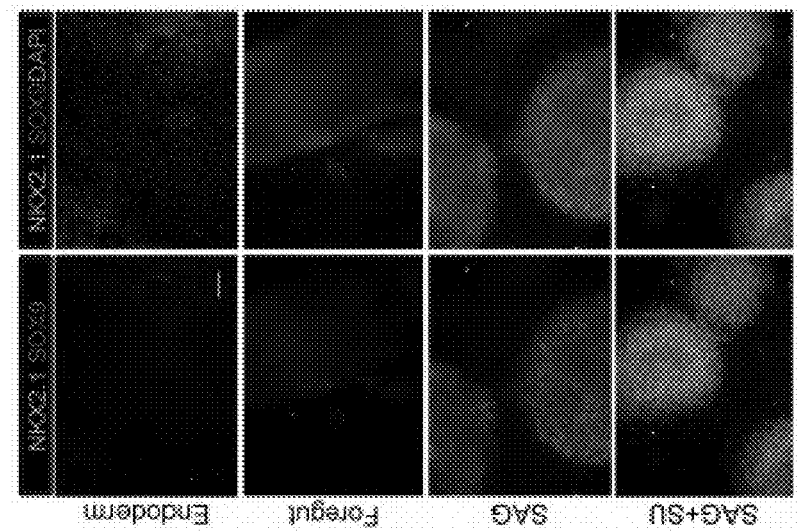
FIG. 2A-C: Monolayer cultures express lung specific markers. Immunohistochemistry for markers expressed in endoderm, ventral foregut or lung epithelium were assessed (50×2, FOXA2, NKX2.1, SOX9) in endoderm controls, foregut controls or foregut cultures treated with SAG or SAG+SU. (A) All conditions express endoderm marker FOXA2 (gray-scaled red), but the foregut (NOG+SB) control, SAG and SAG+SU treated cultures have co-expression of FOXA2 (gray-scaled red) and SOX2 (gray-scaled green) in the majority of cells. (B) All conditions expressed endoderm marker FOXA2 (gray-scaled red), but only foregut endoderm treated with SAG and SAG+SU have robust NKX2.1+ cells (gray-scaled green) that also express FOXA2 (gray-scaled red). (A-B) Scale bars represent 200 µm and apply to all images. (C) Only foregut endoderm treated with SAG and SAG+SU have robust NKX2.1+ cells (gray-scaled green) with the majority of cell co-expressing with lung epithelial marker SOX9 (gray-scaled red). Scale bar represents 100 µm.
Figure 2B:
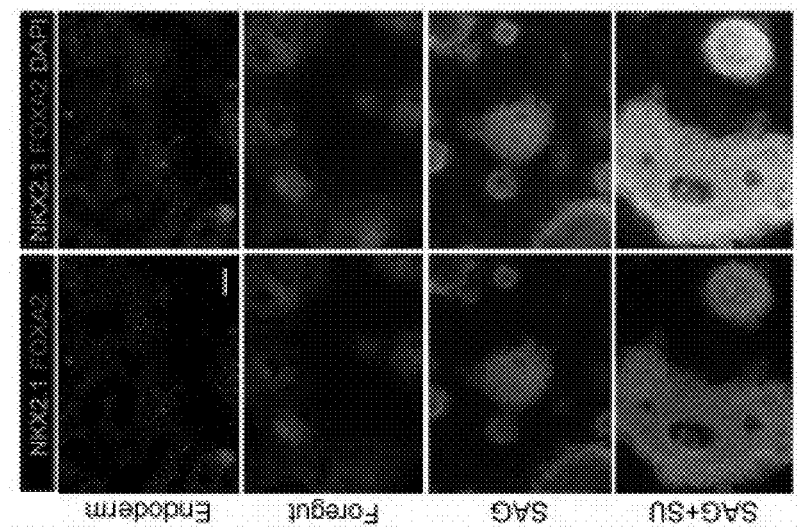
Figure 2C:
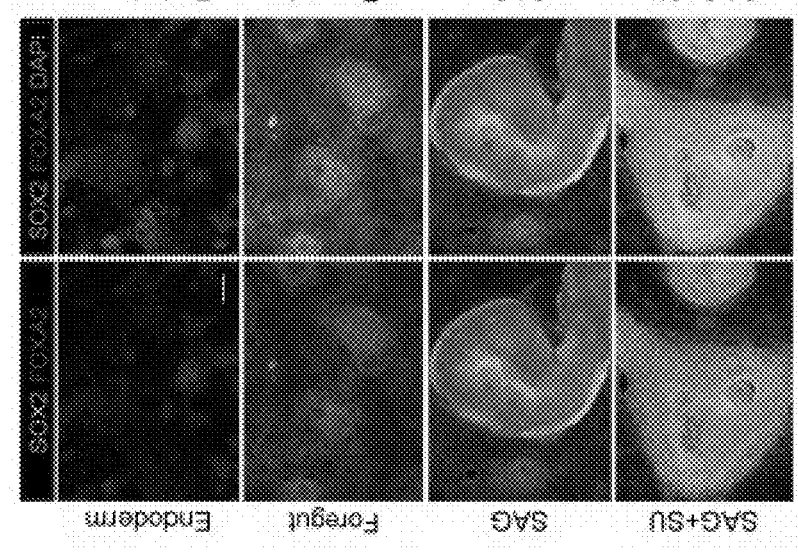
Figure 7A:
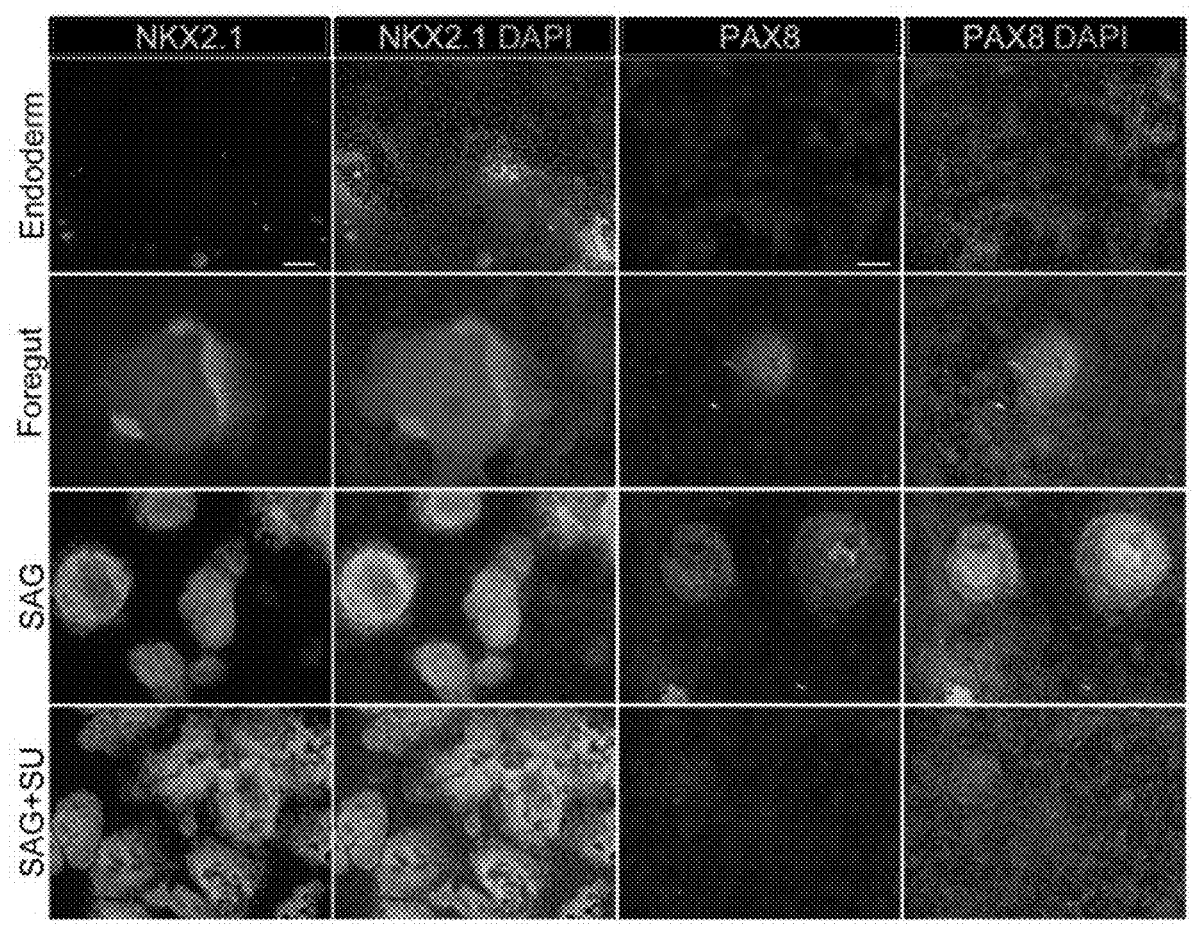
FIG. 7A-B: Robust induction of NKX2.1 in foregut endoderm with HH stimulation and FGF inhibition. (A) Immunohistochemistry of NKX2.1 and PAX8 in endoderm controls, foregut controls or foregut cultures treated with SAG or SAG+SU. Treatment of foregut cultures with SAG or SAG+SU resulted in more NKX2.1+ cells compared to endoderm and foregut controls. Scale bars represent 200 μm and apply to all images. (B) Quantification showed that 20%+/−4% of cells in foregut controls were NKX2.1+, whereas 72%+/−3% cells were positive in SAG+SU treated cultures (*p<0.05). All error bars represent SEM.
Figure 7B:
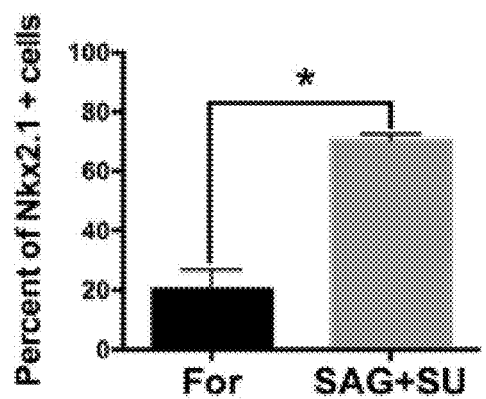

Importantly, immunofluorescence correlated with QRT-PCR data showing an increased number of NKX2.1+ cells with the addition of SAG only. SAG+SU treated cultures showed a further increase in the number of NKX2.1 expressing cells, with ~77% of all cells expressing NKX2.1 compared to ~20% in foregut controls, and nearly undetectable levels of PAX8 expressing cells (FIG. 7). SAG and SAG+SU treated cells also co-expressed FOXA2 and SOX2 confirming their endodermal origin (FIG. 2).

Example III

This example shows that HH-induced foregut spheroids give rise to human lung organoids (HLOs).

Figure 8:
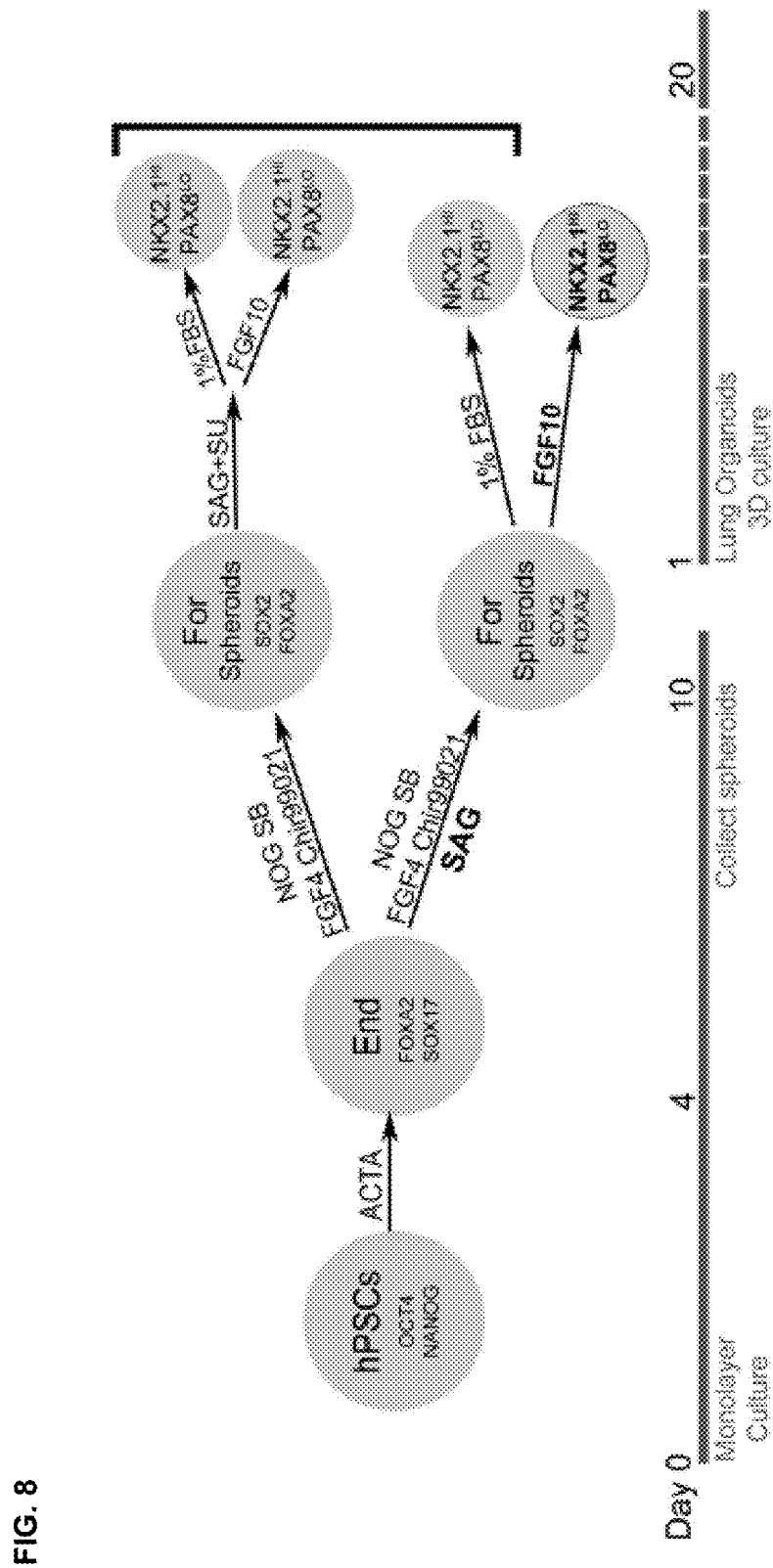
FIG. 8: Overview of conditions tested to generate human lung organoids. hPSCs are OCT4 and NANOG positive. After 4 days of 100 ng/mL Activin A, definitive endoderm (FOXA2 and SOX17 positive) was generated and then treated with two different conditions. In the top branch, NOG+SB+FGF4+Ch spheroids were generated, and different conditions were tested to promote lung organoid differentiation. In the bottom branch, NOG+SB+FGF4+Ch+SAG spheroids were generated, and different conditions were tested to promote lung organoid differentiation. Ultimately, it was determined that spheroids generated with NOG+SB+FGF4+Ch+SAG and that were subsequently embedded in Matrigel and expanded in FGF10 gave rise to "Human Lung Organoids" (HLOs).
Figure 10D:
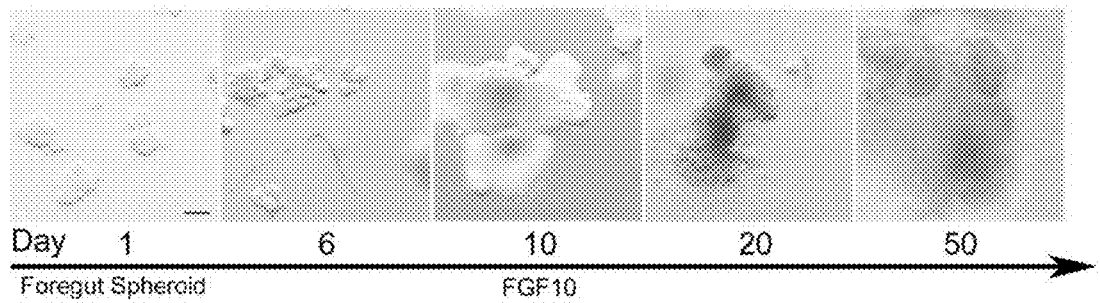
Figure 11A:
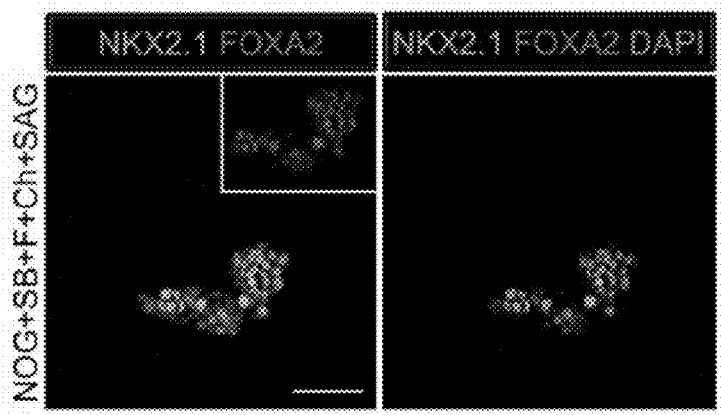
FIG. 11A-B: Foregut spheroids express lung and foregut specific markers. (A) NOG/SB/FGF4/Ch/SAG spheroids coexpress NKX2.1 (gray-scaled green) and the endoderm marker FOXA2 (gray-scaled red). (B) The majority of the cells in the spheroid co-expresses SOX2 (gray-scaled green) and FOXA2 gray-scaled (gray-scaled red). Scale bars represent 50 μM.
Figure 11B:
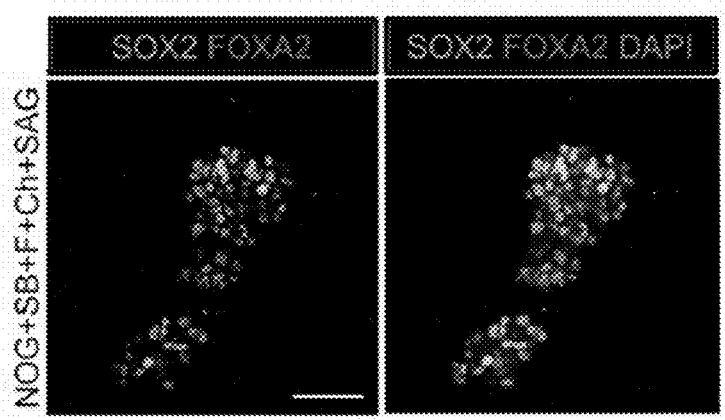

Based on the observations that stimulating HH and inhibiting FGF signaling strongly enhances NKX2.1 expression while reducing PAX8 expression (FIG. 5), multiple conditions of HH activation and FGF inhibition to induce NKX2.1$^{HI}$/PAX8$^{LO}$ foregut spheroids (NOG/SB/F/Ch) were tested (FIG. 8). Consistent with the important roles of FGF signaling in lung growth and branching morphogenesis (see, e.g., Rankin S A, et al., J Cell Biochem. 2014 Mar. 19; Hebrok M, et al., Genes & Development. 1998; Morrisey E E, et al., Developmental Cell.; 2010 Jan. 19; 18(1):8-23; Min H, et al., Genes & Development. 1998 Oct. 15; 12(20):3156-61; Weaver M, et al., Development. 2000 June; 127(12): 2695-704; Abler L L, et al., Dev. Dyn. 2009 August; 238(8):1999-2013), it was found that conditions where FGF inhibition was used led to a reduction of epithelial tissue relative to mesenchymal tissue, which could be due to a loss of epithelium or an overgrowth of mesenchyme; this suggests that endogenous FGF signaling is necessary to maintain the epithelial tissue in 3D cultures (FIG. 9). Therefore, several conditions were also tested that stimulated HH signaling using SAG only, without FGF inhibition. It was found that the most efficient method to enhance NKX2.1 expression was by adding SAG during the foregut spheroid phase (FIG. 10A). Comparing foregut spheroids (NOG/SB/F/Ch) with those treated with SAG (NOG/SB/F/Ch/SAG), a substantial decrease in SOX2 expression compared to NOG/SB/F/Ch spheroids was observed and a significant increase in NKX2.1 mRNA. Additionally, nuclear NKX2.1 protein expression was found in ECAD+ epithelium which co-expressed endoderm epithelial markers FOXA2 and SOX2 (FIG. 10B, C, FIG. 11). Interestingly, during lung specification in mice, the gut tube initially expresses Sox2 throughout the endoderm, but Sox2 is down-regulated in the lung field during lung specification and Nkx2.1 induction (see, e.g., Hebrok M, et al., Genes & Development. 1998; Serls A E.; Development. 2004 Dec. 2; 132(1):35-47; Domyan E T, et al., Development. 2011 Feb. 8; 138(5):971-81). Thus, concomitant down-regulation of SOX2 and increased NKX2.1 observed in SAG treated foregut spheroids is consistent with early transcriptional changes that occur during lung specification in mice.

Figure 12:
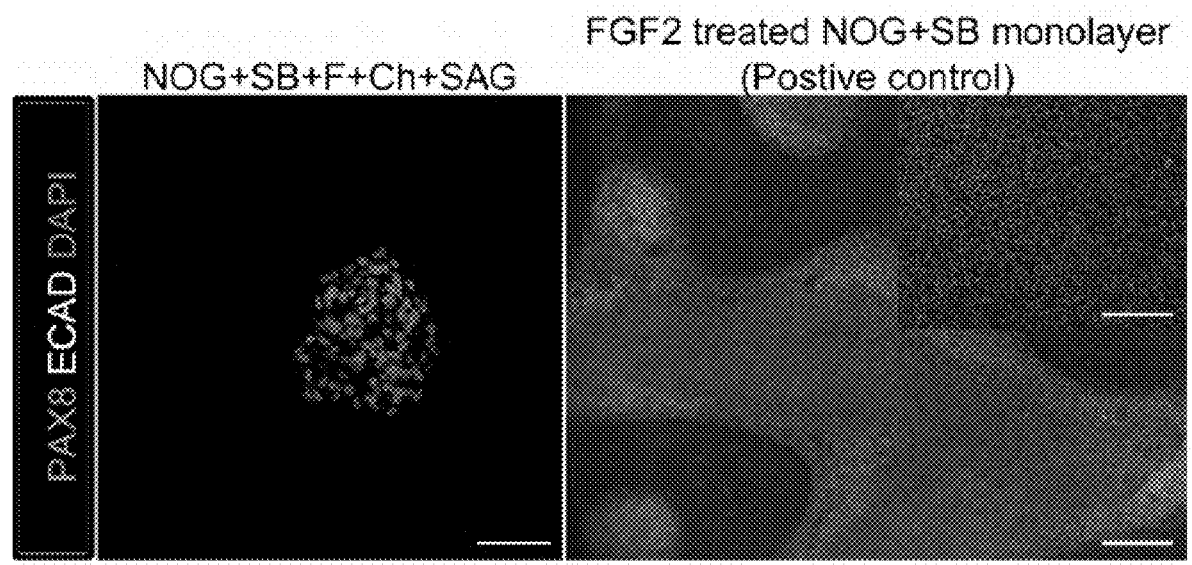
FIG. 12: Ventral foregut spheroids do not express appreciable levels of PAX8 protein. Although NOG+SB+FGF4+Ch+SAG ventral foregut spheroids expressed PAX8 mRNA (FIG. 10B), PAX8 protein was not detected in spheroids using immunofluorescence, whereas PAX8 protein in FGF2 8 day treated foregut monolayers (ACTA followed by NOG/SB) was readily detectable. Left panel: scale bar represents 50 μm. Right panel: scale bar represents 200 μm, inset scale bar represents 100 μm.
Figure 13:
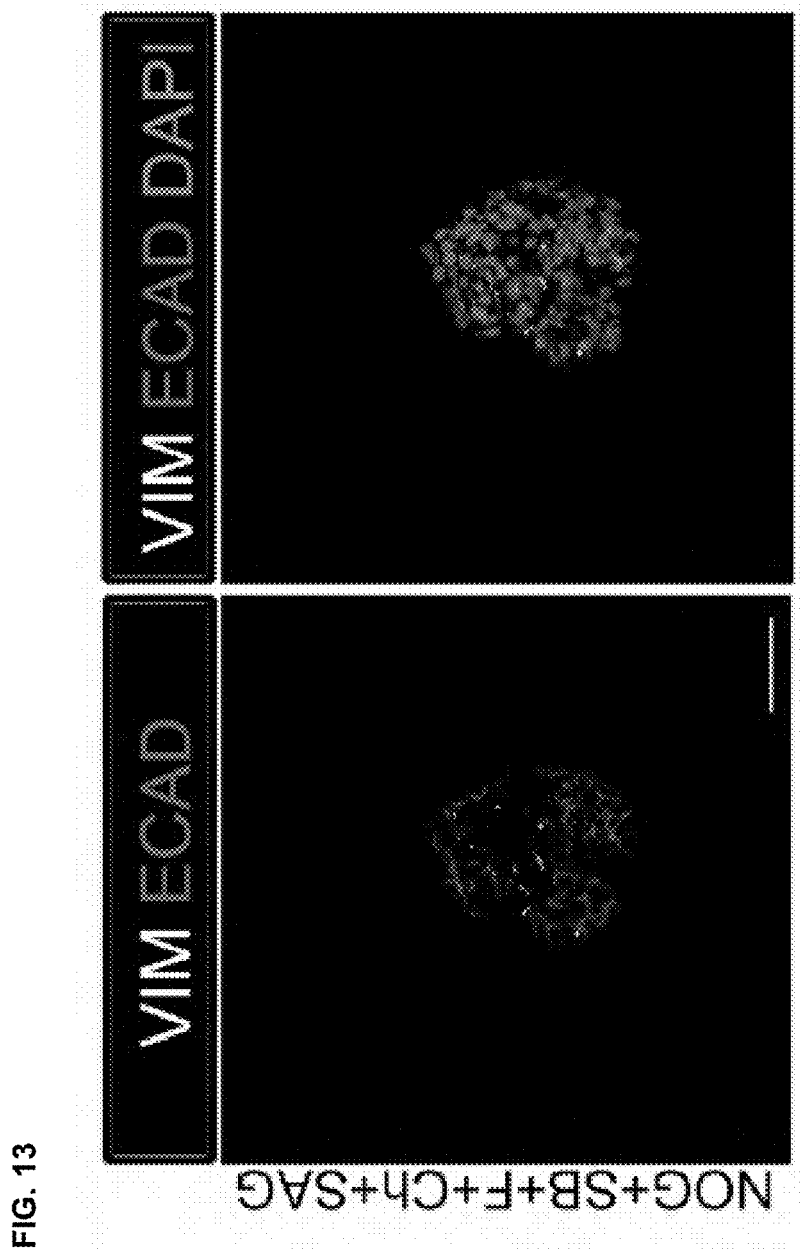
FIG. 13: Foregut spheroids consist of both epithelial and mesenchymal cells. NOG/SB/FGF4/Ch/SAG spheroids have a minor population of Vimentin (VIM, white) positive mesenchymal cells, while the majority of cells are epithelial and express ECAD (gray-scaled red). Scale bar represents 50 μM.

It was also observed a slight, but non-significant increase in PAX8 transcript level in NOG/SB/F/Ch/SAG treated foregut spheroids (FIG. 10B). Importantly, PAX8 protein expression was undetectable in NOG/SB/F/Ch/SAG treated foregut spheroids and expression remained low/undetectable throughout time in culture (FIG. 12). Similar to NOG/SB/F/Ch treated spheroids, the NOG/SB/F/Ch/SAG treated spheroids had a minor population of cells within the spheroids of mesodermal in origin, expressing Vimentin (VIM) (FIG. 13).

Figure 9A:
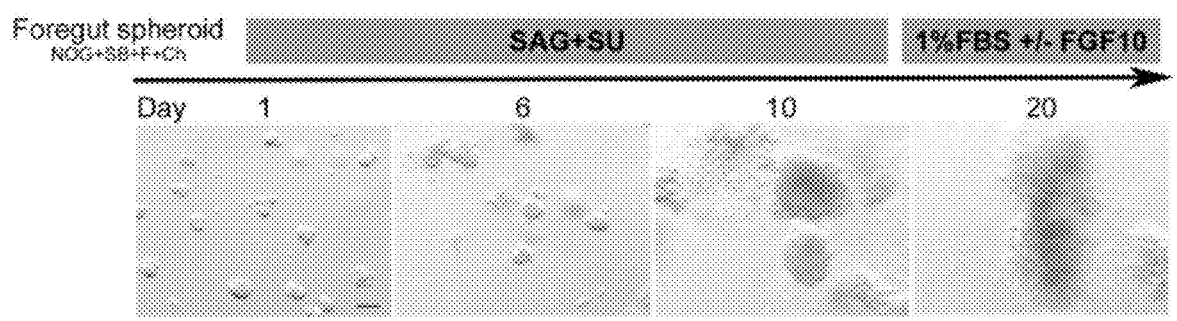
FIG. 9A-E: FGF-low culture conditions cause a loss of organoid epithelium over time. (A) NOG+SB+F+Ch foregut spheroids were generated and then cultured in SAG+SU for 10 days followed by 1% FBS+/−FGF10. Timeline images show organoids cultured in 1% FBS. By day 20, 3D structures appeared "fuzzy", which indicates an outgrowth of mesenchymal tissue. Scale bar represents 200 μm. (B) NOG+SB+F+Ch foregut spheroids treated with SAG+SU and maintained in 1% FBS showed an increase in Vimentin (VIM, gray-scaled green) immunofluorescence over time. Scale bar represents 50 μM. (C) NOG+SB+F+Ch foregut spheroids treated with SAG+SU and maintained in 1% FBS (upper panel) or 1% FBS+FGF10 (lower panel) had a significant increase of VIM expression starting at day 20 (D20) compared to hPSCs and showed very weak E-CAD-HERIN (CDH1) expression compared to D20 HLOS (optimized conditions, as described in FIG. 10). Lastly, both conditions appeared to lose NKX2.1 expression over time. (D) NOG+SB+F+Ch+SAG spheroids maintained in 1% FBS (basal media) also appear to lose epithelial structures over time. Scale bar represents 200 μm. (E) By day 20 (D20) the tissue had very few epithelial structures expressing ECAD (white, left panel) and there was robust VIM expression (gray-scaled green, right panel) at both time points. Scale bar represents 50 μm. HLO. *p<0.05. All error bars represent SEM.
Figure 9B:
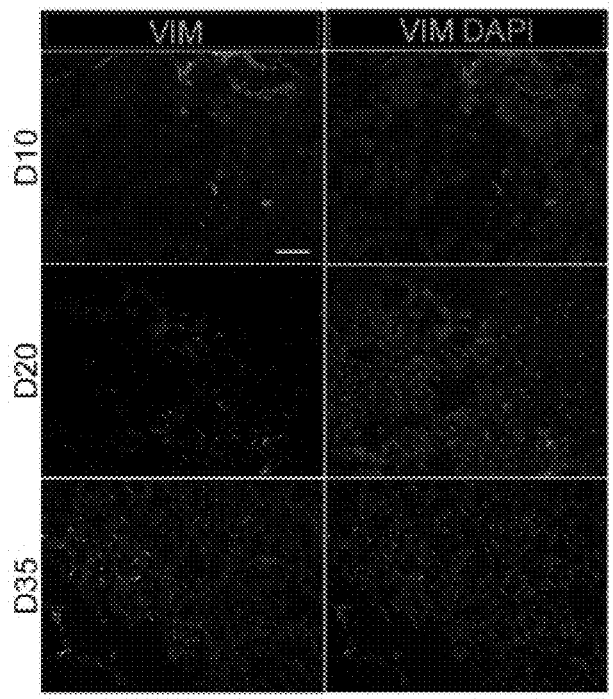
Figure 9C:
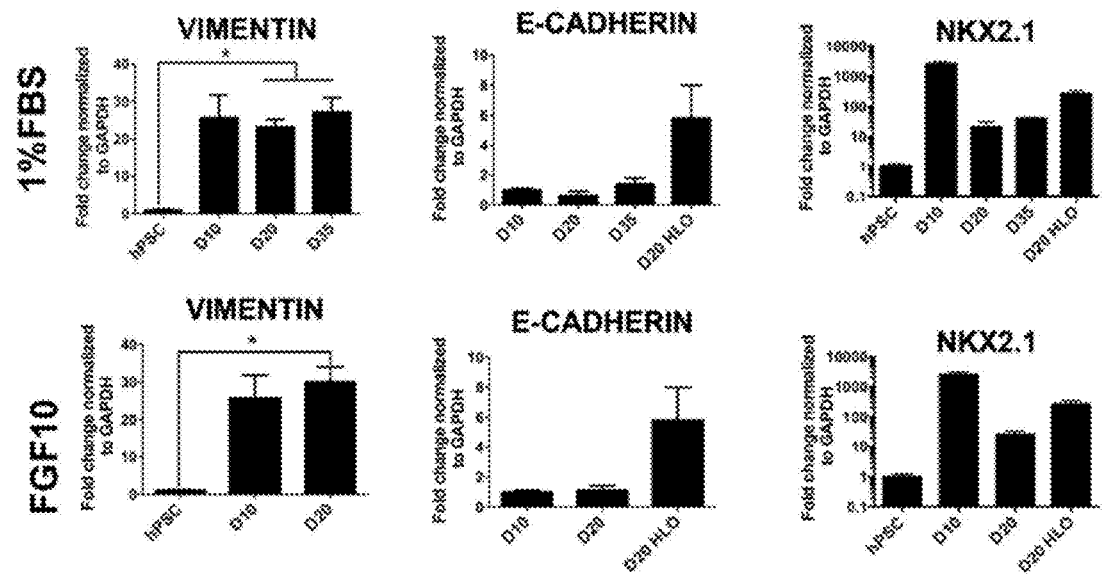
Figure 9D:
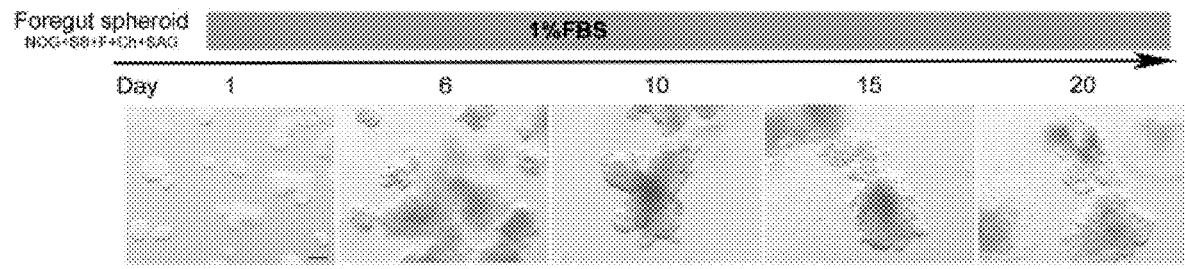
Figure 9E:
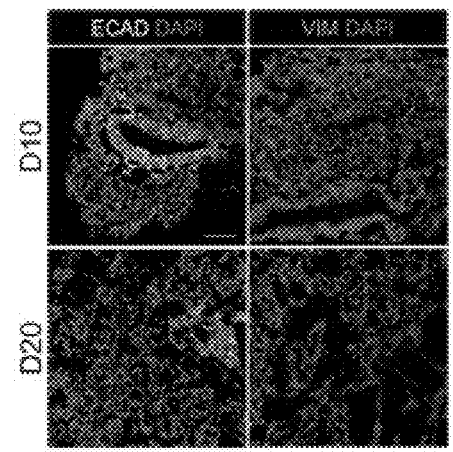
Figure 10E:
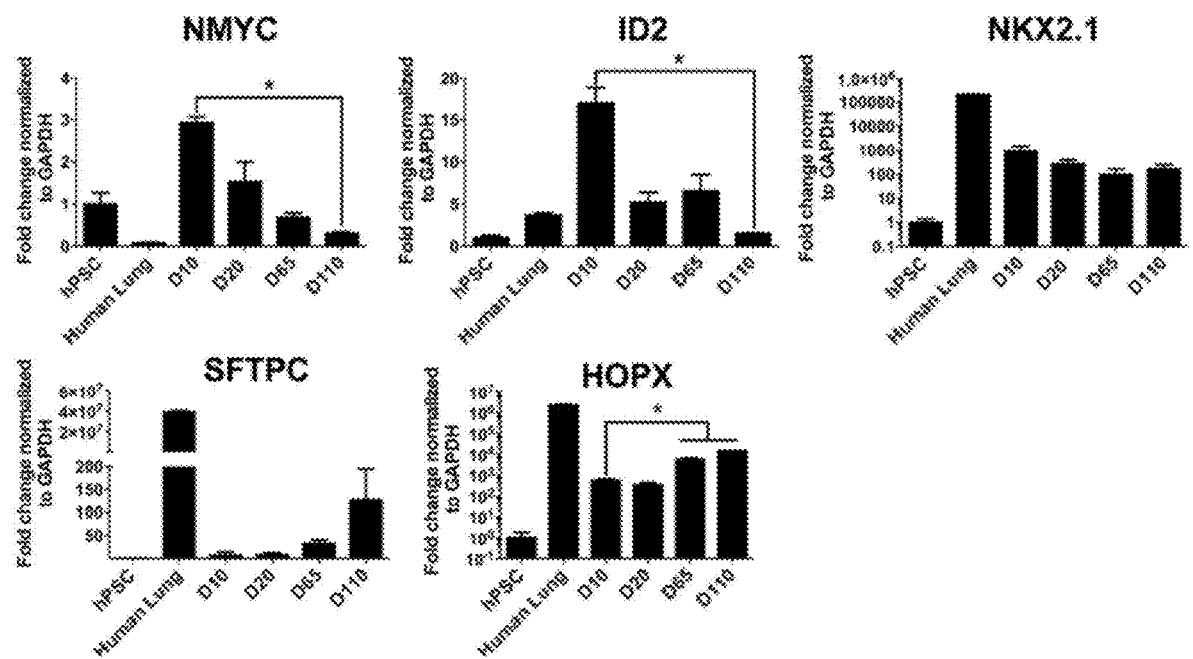
Figure 14:
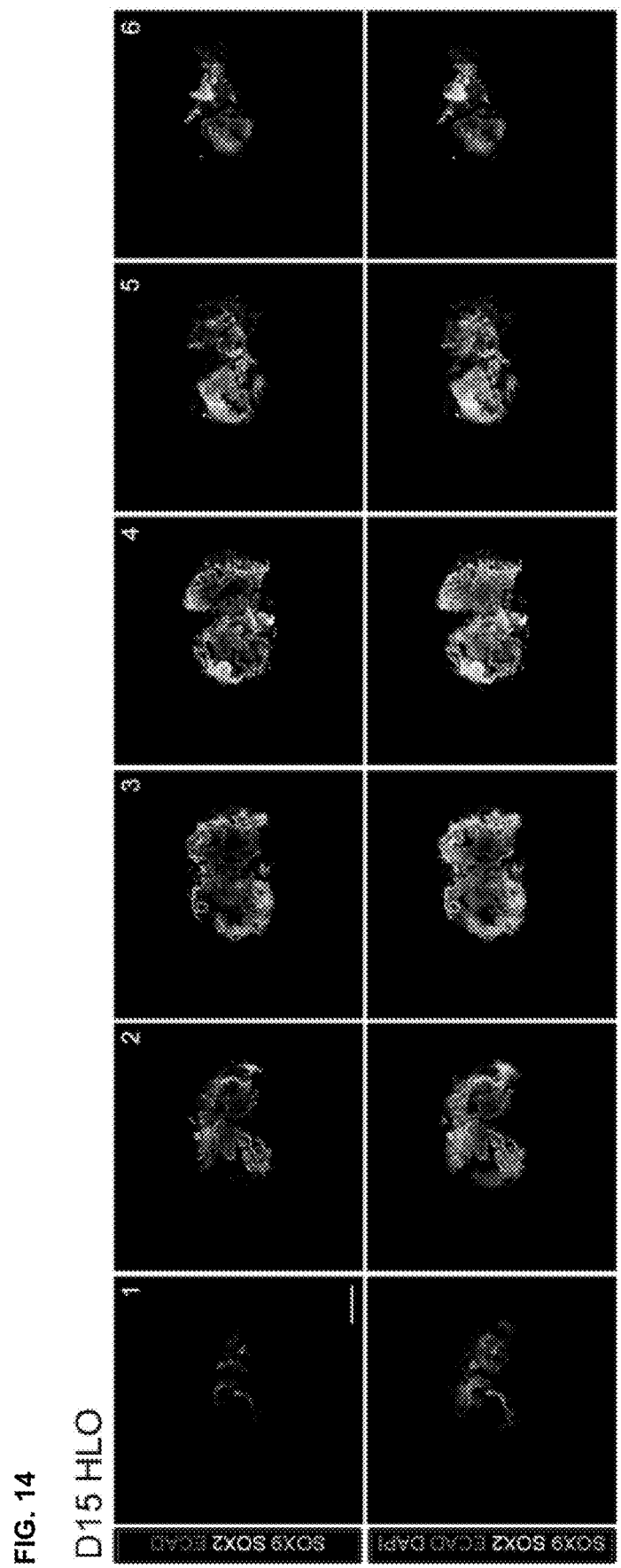
FIG. 14: Lung organoids contain both proximal and distal domains. NOG/SB/FGF4/Ch/SAG spheroids cultured for 15 days with FGF10 express the distal lung epithelium marker SOX9 (gray-scaled green) and proximal marker SOX2

NOG/SB/F/Ch/SAG treated foregut spheroids were embedded in Matrigel to provide a 3D growth environment. Spheroids maintained in basal media supplemented with 1% FBS lost ECAD+ epithelial structures and were mainly comprised of mesenchyme within 20 days of 3D culture (FIG. 9D,E). FGF10 is essential for branching morphogenesis and maintenance of lung progenitor cells during development as well as tissue homeostasis in the adult lung (see, e.g., Motoyama J, et al., Nat Genet. 1998 September; 20(1):54-7; Li Y, et al., Developmental Biology. 2004 Jun. 1; 270(1):214-31; Bellusci S, et al., Development. 1997 January; 124(1):53-63; Min H, et al., Genes & Development. 1998 Oct. 15; 12(20):3156-61; Weaver M, et al., Development. 2000 June; 127(12):2695-704; Agha El E, et al., Development. 2013 Dec. 18; Volckaert T, et al., Development 2013 September; 140(18):3731-42). It was observed that the addition of FGF10 (500 ng/mL) allowed spheroids to expand and be passaged for over 100 days. FGF10 promoted the maintenance of ECAD+ epithelial structures with less mesenchymal contributions compared to both basal and FGF inhibitor conditions (FIG. 10D). NOG/SB/F/Ch/SAG cultured for 15 days in FGF10 possessed abundant ECAD+ epithelium that expressed the proximal lung marker SOX2 and distal lung marker SOX9. SOX2+ domains and SOX9+ domains were distributed throughout the entire HLO as determined by whole mount immunofluorescence and confocal Z-sections (FIG. 14). FGF10 treated foregut spheroids maintained NKX2.1 expression over time; however, consistent with mouse development, distal progenitor markers, NMYC and 1D2 mRNA expression decreased over time while distal Alveolar Type I and II cell markers, HOPX and SFTPC increased over time (see, e.g., Li Y, et al., Developmental Biology. 2004 Jun. 1; 270(1):214-31; Kimura S, et al., Genes Dev. January 1; 10(1):60-9; Yuan B, et al., Dev. Dyn. 2000 February; 217(2):180-90; Narumi S, et al., Eur. J. Endocrinol. 2012 November; 167(5):625-32; Vilain C, et al., J. Clin. Endocrinol. Metab. 2001 January; 86(1):234-8; Mansouri A, et al., Nat Genet. 1998 May; 19(1):87-90; Kusakabe T, et al., Mol. Endocrinol. 2006 August; 20(8): 1796-809; Cane A, et al., Hum. Mol. Genet. 2009 Jun. 15; 18(12):2266-76; Okubo T.; Development. 2005 Feb. 9; 132(6):1363-74; Rawlins E L, et al., Development. 2009 November; 136(22):3741-5 (FIG. 10E). These data suggest that HLOs pass through a stage resembling early fetal lung development in mice.

Example IV

Figure 15A:
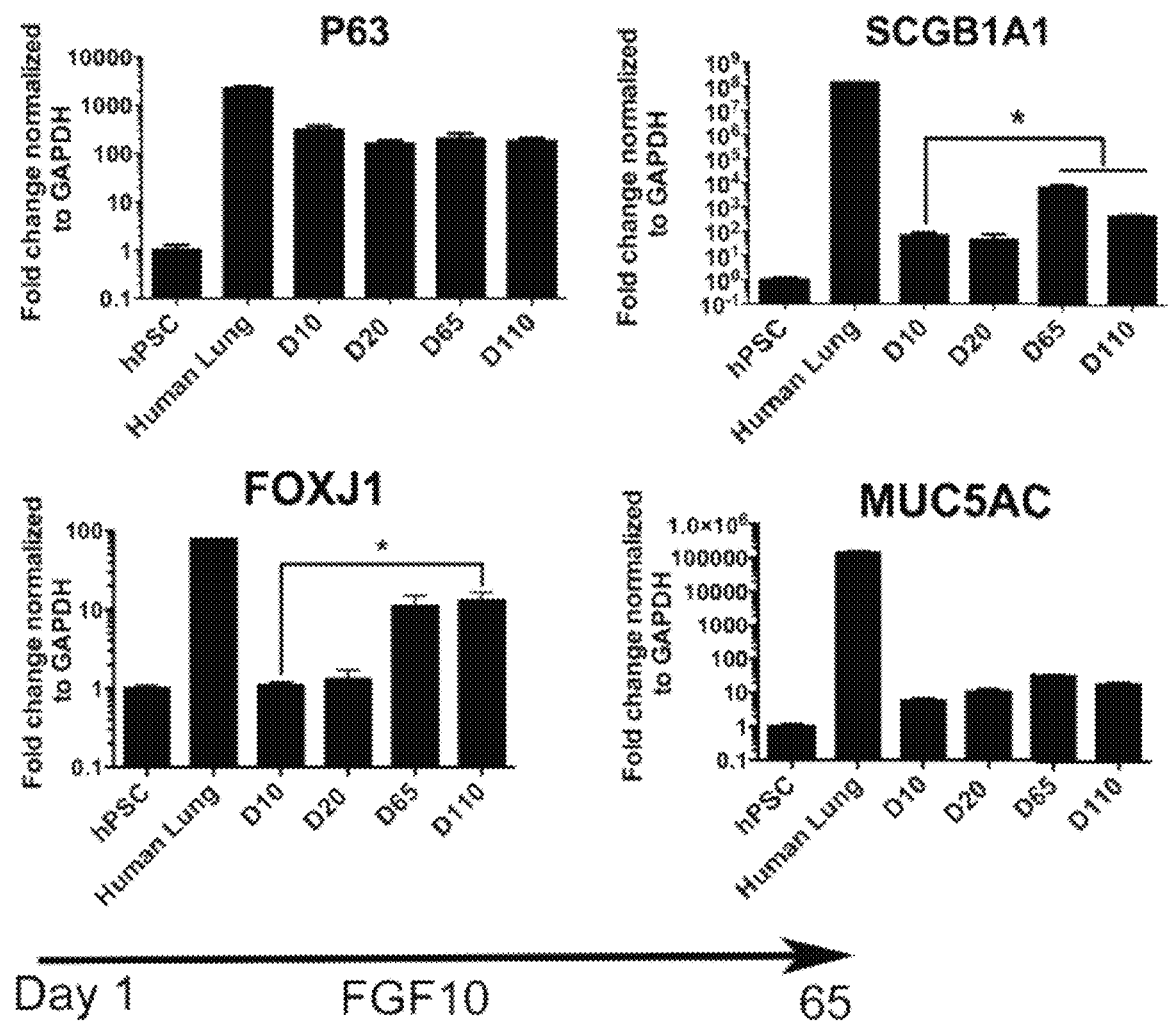
Figure 15B:
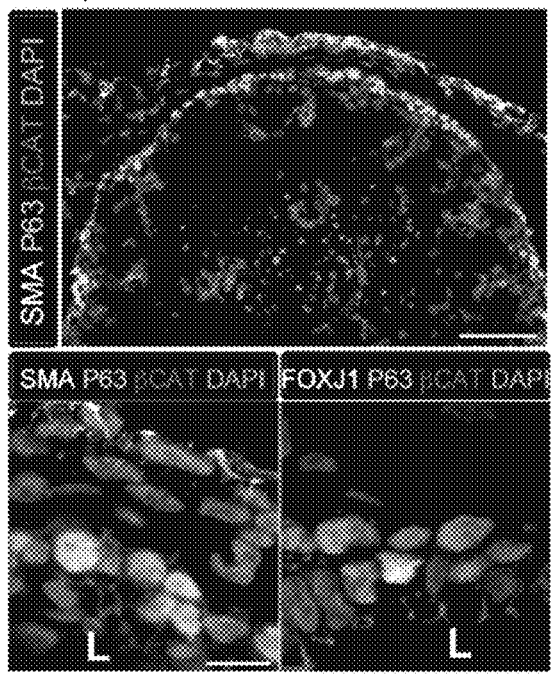
Figure 15C:
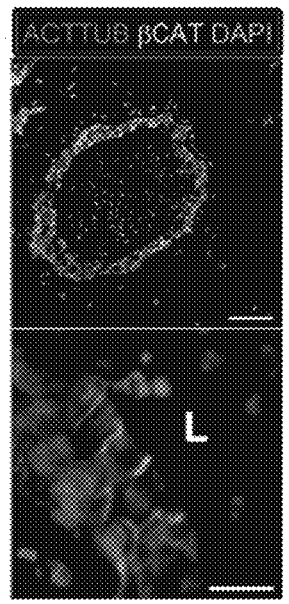
Figure 15D:
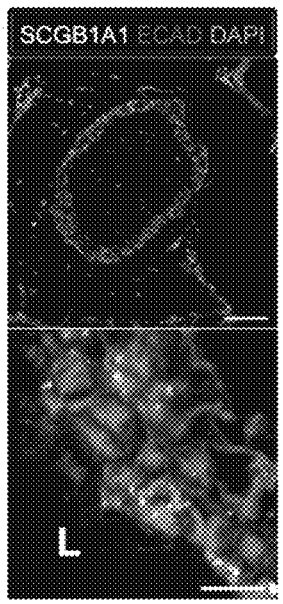

This example demonstrates that HLOs possess proximal airway-like structures. HLOs cultured longer than 2 months had striking epithelial structures resembling proximal airways, expressing proximal cell type-specific markers, including basal cells (P63), ciliated cells (FOXE, ACTTUB) and club cells (SCGB1A1) (FIG. 15). Proximal-like airway tissues were often surrounded by a smooth muscle actin positive (SMA+) mesenchyme compartment. Although P63 mRNA expression is maintained throughout culture (FIG. 15A), it is only in prolonged cultures (>2 months) where the P63+ cells are spatially arranged along the basal side of the epithelial tube-like structures, adjacent to SMA+ mesenchyme, similar to human bronchi and bronchioles (FIG. 15B) (see, e.g., Spence J R, et al., Nature. 2011 Feb. 3; 470(7332):105-9; D'Amour K A, et al., Nat Biotechnol. 2005 Oct. 28; 23(12):1534-41; Zhang M, Wang H, Teng H, Shi J, Zhang Y. Expression of SHH signaling pathway components in the developing human lung. Histochem. Cell Biol. 2010 October; 134(4):327-35; Evans M J, et al., Exp. Lung Res. 2001 July; 27(5):401-15; Rock J R, et al., Proceedings of the National Academy of Sciences. 2009 Aug. 4; 106(31):12771-5; Nakajima M, et al., Pathol. Int. 1998 December; 48(12):944-53; Boers J E, et al., American Journal of Respiratory and Critical Care Medicine. 1998 June; 157(6 Pt 1):2000-6). By 65 days in vitro (D65) proximal-like epithelial structures form a cyst-like structure that expresses P63, as determined by whole mount immunofluorescence staining and confocal z-stacks. Moreover, SMA expression is strongest at the periphery of the HLO (FIG. 16). P63+ proximal airway-like cells also co-express SOX2 and NKX2.1 as determined on serial sections (FIG. 17). Located on the luminal surface of HLO proximal airway-like structures are cells expressing the multi-ciliated cell transcription factor FOXJ1 (FIG. 15B). Very few cells expressed the club cell marker SCGB1A1, and this protein was observed in a pixilated expression pattern (FIG. 15D). Multi-ciliated and club cell specific mRNAs, FOXJJ and SCGB1A1 respectively, were significantly increased in prolonged HLO culture (FIG. 15A). Although the goblet cell marker MUC5AC mRNA expression was detected, protein expression was not detected by immunofluorescence (FIG. 15A).

Figure 15E:
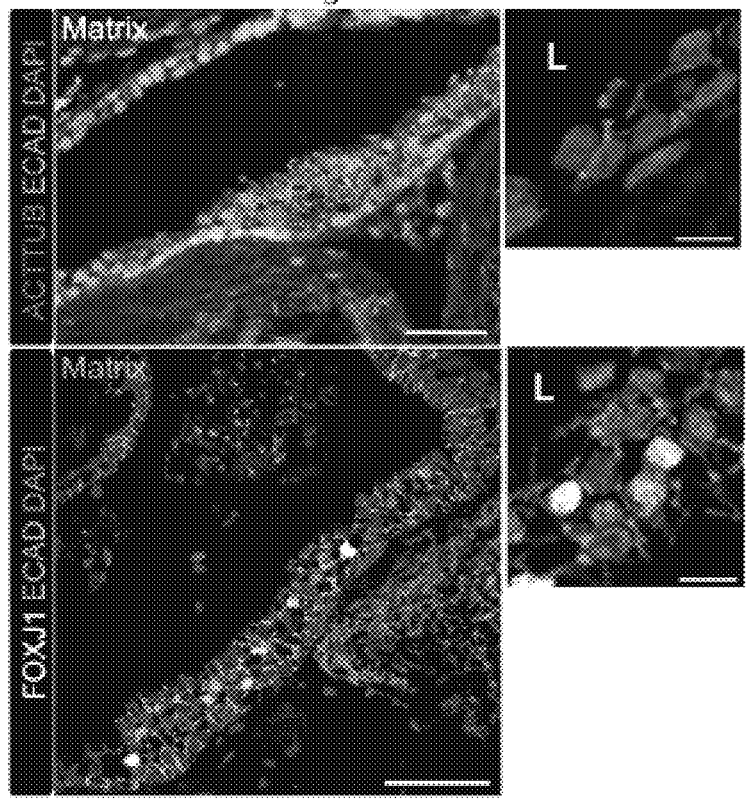

Although the multi-ciliated cell transcription factor FOXJ1 was abundant in proximal airway-like structures, it was observed that ACTTUB was localized to the apical side of these cells, but did not appear to be localized to cilia on the apical cell surface (FIG. 15C), suggesting that this may represent a cell that has not fully differentiated. It has been demonstrated that robust differentiation of multi-ciliated cells from hPSCs require modified culture conditions to promote differentiation of functional cell types (see, e.g., Firth A L, et al., Proceedings of the National Academy of Sciences. 2014 Apr. 29; 111(17); Green M D, et al., Nat Biotechnol; 2011 Feb. 27; 1-7; Loh K M, et al., Cell Stem Cell. 2014 Feb. 6; 14(2):237-52). Thus, it is possible that the HLO environment, such as Matrigel or media rich in FGF10, does not promote terminal differentiation of all cell types. In order to alter the HLO environment, seeded NOG/SB/F/Ch/SAG foregut spheroids were seeded onto an acellular human lung matrix (see, e.g., Green M D, et al., Nat Biotechnol. Nature Publishing Group; 2011 Feb. 27; 1-7; Booth A J, et al., American Journal of Respiratory and Critical Care Medicine. 2012 Nov. 1; 186(9):866-76). Spheroids seeded on slices of acellular lung matrix predominantly gave rise to proximal airway-like structures in which stereotypical tufts of ACTTUB positive ciliated structures on the apical surface of cells were observed facing into a lumen. In serial sections, these airways had abundant FOXJ1+ cells (FIG. 15E). Thus, HLOs have the capacity to generate more mature ciliated cells given the correct stimulus or environment.

As noted, proximal airways are often closely associated with the SMA+ mesenchyme (FIG. 15B) whereas in the adult murine lung, proximal airways are also associated with Pdgfrα+ and Vim+ mesenchymal cells (see, e.g., Chen L, et al., American Journal of Respiratory Cell and Molecular Biology. 2012 October; 47(4):517-27; Hinz B, et al., The American Journal of Pathology. 2007 June; 170(6):1807-16; Boucherat O, et al., American Journal of Respiratory and Critical Care Medicine. 2007 May 15; 175(10):1066-77). Thus, the mesenchymal population within the HLOs was investigated in more detail. Immunofluorescence revealed that D65 HLOs have both PDGFRα+NIM+ double positive and PDGFRα−/VIM+ cell populations, which indicative of myofibroblasts and fibroblasts respectively (FIG. 18A). Adult murine myofibroblasts also co-express Sma and Pdgfrα whereas differentiated smooth muscle is Sma+/Pdgfrα− (see, e.g., Chen L, et al., American Journal of Respiratory Cell and Molecular Biology. 2012 October; 47(4):517-27; Hinz B, et al., The American Journal of Pathology. 2007 June; 170(6):1807-16; Boucherat 0, et al., American Journal of Respiratory and Critical Care Medicine. 2007 May 15; 175(10):1066-77; Leslie K O, et al., Differentiation. 1990 August; 44(2):143-9; Low R B, et al., Int. J. Biochem. Cell Biol. 1998 August; 30(8):869-83), and PDGFRα+/SMA+ and PDGFRα−/SMA+ populations of cells were observed indicating that HLOs possess myofibroblasts and smooth muscle cells (FIG. 18B). The HLOs did not stain positive for SafraninO indicating there is no cartilage tissue, whereas iPSC derived teratomas had abundant cartilage (FIG. 18C). Taken together, the HLO mesenchymal population is diverse with myofibroblasts, fibroblasts, and smooth muscle cells.

Example V

This example demonstrates that HLOs possess immature alveolar airway-like structures.

Figure 19A:
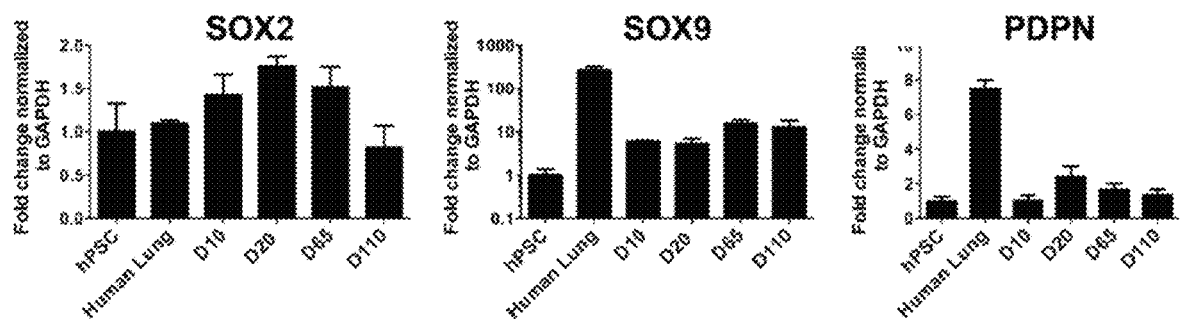

The distal lung epithelium in mouse and human make up the gas-exchanging alveoli, consisting of type I and type II alveolar epithelial cells (AECI, AECII). During development, the distal lung epithelium expresses progenitor markers including SOX9, ID2, and NMYC (see, e.g., Spence J R, et al., Nature. 2011 Feb. 3; 470(7332):105-9; Green M D, et al., Nat Biotechnol.; 2011 Feb. 27; 1-7; Xue X, et al., Gastroenterology. 2013 Jul. 13; Chen Y-J, et al., Cell Rep.; 2014 Mar. 4; 1-13; Okubo T; Development. 2005 Feb. 9; 132(6):1363-74; Rawlins E L, et al., Development. 2009 November; 136(22):3741-5; Rockich B E, et al., Proceedings of the National Academy of Sciences. 2013 Nov. 4; Chang D R, et al., Proceedings of the National Academy of Sciences. 2013 Sep. 20). All distal markers are present in the HLOs; however, ID2 and NMYC are expressed at high levels in early cultures, but are down regulated in prolonged culture (FIG. 10F) while SOX9 expression remains consistent across time in culture (FIG. 19A).

Figure 19B:
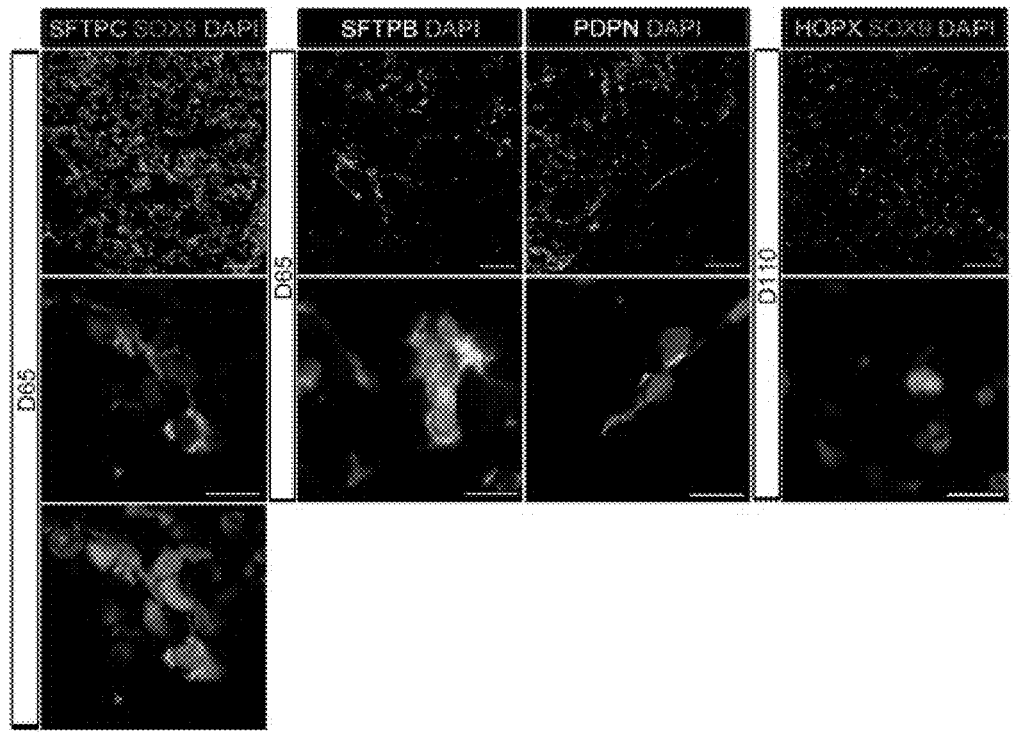
Figure 19C:
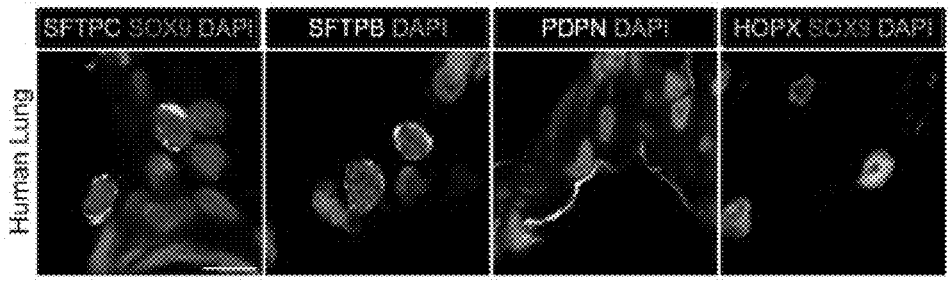
Figure 19D:
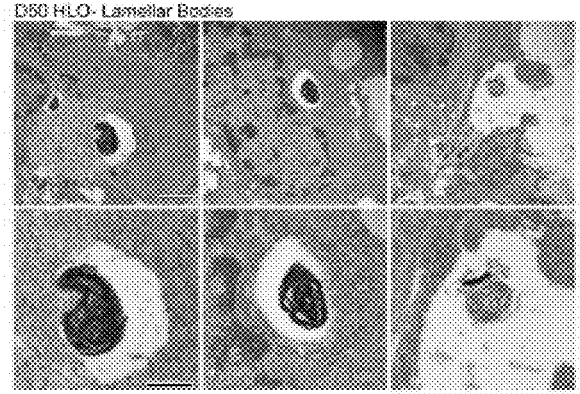

Recently, there have been major advances in mice toward defining a bipotent alveolar progenitor population during the late fetal/early neonatal period (see, e.g., Desai T J, et al., Nature. 2014 Feb. 5; Treutlein B, et al., Nature. 2014 May 15; 509(7500):371-5; Chambers S M, et al., Nat Biotechnol. 2009 Mar. 1; 27(3):275-80), and this work has highlighted the fact that many markers previously considered terminal differentiation markers are co-expressed in the bipotent progenitors. Specifically, the AECII marker SftpC and AECI marker Hopx can be co-expressed in a bipotent progenitor before becoming committed to one lineage or the other. Moreover, it has been shown that Sox9 marks an early progenitor population in the developing mouse lung and Sox9 also marks the bipotent progenitor in late fetal life (see, e.g., Treutlein B, et al., Nature. 2014 May 15; 509(7500): 371-5; Monaghan A P, et al., Development. 1993 November; 119(3):567-78; Ang S L, et al., Cell. 1994 Aug. 26; 78(4): 561-74; Rockich B E; et la., Proceedings of the National Academy of Sciences. 2013 Nov. 4). In HLOs grown in prolonged culture (>2 months), it was observed that AECII (SFTPC, SFTPB) and AECI (PDPN, HOPX) cell-type markers were present (FIG. 19A-B). However, it was also observed that SFTPC levels were very low (FIG. 10F), and that SFTPB+ cells were rare (FIG. 19B). This suggested that the distal airway cells present in HLOs might be a progenitor-like population. To test this possibility, SFTPC (AECII) or HOPX (AECI) was co-stained with SOX9 and abundant SFTPC/SOX9 and HOPX/SOX9 double positive cells were found (FIG. 19B). Co-staining in serial sections suggests that SFTPC/SOX9 double positive cells are also NKX2.1+ (FIG. 20). In contrast these co-expressing cells were not found in the adult human lung (FIG. 19C). Although rare, the few SFTPB+ observed in HLOs resemble AECII cells seen in the adult human lung, and PDPN+ cells resembled the elongated AECI cells in the human lung (FIG. 19B-C). In order to improve confidence that cells expressing AECII markers are AECII cells, transmission electron microscopy (TEM) was used to determine if HLOs possessed cells containing lamellar bodies, which are necessary for surfactant protein trafficking and secretion (see, e.g., Weaver T E, et al., Seminars in Cell & Developmental Biology. 2002 August; 13(4):263-70; Schmitz G, et al., J. Lipid Res. 1991 October; 32(10):1539-70; Stahlman M T, et al., Lab. Invest. 2000 March; 80(3):395-403). Using TEM, lamellar bodies were observed both in cells within HLOs, and in open spaces between cells, indicating that lamellar bodies are being secreted (FIG. 19D). Taken together, these data suggest that HLOs predominantly possess an undifferentiated alveolar progenitor cells with rare differentiated AECI and AECII cells interspersed throughout the distal-like tissue.

Example VI

This example provides a quantitative assessment of HLO composition.

It has been shown that HLOs have both proximal-like and distal-like epithelium in addition to surrounding mesenchymal tissue. In order to better gauge the composition of HLOs, a detailed quantitative analysis of cell types and structures was performed. 48 individual HLOs were sectioned and examined for P63+ proximal airway-like structures (FIG. 15B-D), and distal-airway like structures (FIG. 20). It was found that 39/48 (81%) of the HLOs have proximal airway epithelial structures while 48/48 (100%) of HLOs have distal airway-like structures (FIG. 21A). The average cross-sectional area comprised of P63+ proximal airway-like and P63– distal airway-like tissue were calculated and it was found that proximal structures comprised 14.5% (+/−0.6%) of the entire area of the HLO, whereas 85.5% (+/−0.6%) were distal in nature (including epithelium and mesenchyme) (FIG. 21B). To determine the percentage of certain cell types within an HLO, 15 individual HLOs (n=15) were sectioned and stained, cells positive for specific markers counted, and the total number of Dapi+ nuclei within a section determined (FIG. 217C-G). On average, 57% of all cells in the HLOs were NKX2.1+ (FIG. 21C), 39% of all cells were P63+, 3% were FOXJ1+, 5% were SFTPC+4% of all cells were HOPX+ (FIG. 21D-G).

Example VII

This example demonstrates that HLOs are globally similar to human fetal lung.

Accumulating evidence suggests that HLOs are immature. For example, distal progenitor markers are initially robustly expressed whereas SFTPC expression is very low across time in HLOs (FIG. 10E), FOXJ1+ cells do not appear to form mature multi-ciliated structures until placed onto a decelluarized lung matrix (FIG. 15B, E) and rare SCGB1A1+ cells do not resemble mature club cells (FIG. 15D). Moreover, the majority of the distal-like epithelium expresses bipotent progenitor markers (FIG. 19). In order to directly address the maturity of HLOs, RNA-sequencing (RNAseq) was conducted on HLOs (n=6; 3 D65 HLOs, 3 D110 HLOs), on undifferentiated hESCs, and on definitive endoderm. Publicly available RNAseq datasets were utilized for human fetal lung representing a range of gestational stages, and for adult human lung (FIG. 22). In order to determine global similarity among these tissues relative to HLOs, principal component (PC) analysis was conducted (FIG. 23A,B) (see e.g., Ringnér M.; Nat Biotechnol. 2008 March; 26(3):303-4), hierarchical clustering (FIG. 238C) (see, e.g., Eisen, et al., PNAS Dec. 8, 1998 vol. 95 no. 25 14863-14868), and Spearmans rank-order correlation matrix analysis (FIG. 23D) of the complete tabulated FPKM matrix generated from RNA sequences datasets and representing the total gene expression complement in each sample (see, e.g., Daxin Jiang, et al., IEEE Trans. Knowl. Data Eng. 2004 November; 16(11):1370-86). Consistent across all three types of informatics analysis, transcriptional activity in the HLOs shares the greatest degree of similarity to human fetal lung. These data strongly suggest that global transcription of HLOs is highly similar to human fetal lung, and support the idea that HLOs are in a less differentiated, fetal state when grown in the conditions described here.

Example VIII

This example provides the materials and methods relating to Examples I-VII.
Maintenance of hESCs Human ES cell lines H1 (NIH registry #0043) and H9 (NIH registry #0062) were obtained from WiCell Research Institute. Human ES line UM77-2 (NIH registry #0278) was obtained from the University of Michigan. iPSC lines 3-5 and 20-1 were generated at Cincinnati Children's Hospital and have been previously described (see, e.g., Spence J R, et al., Nature. 2011 Feb. 3; 470(7332):105-9). Stem cells were maintained on Matrigel (BD Biosciences) in mTesR1 medium (STEM CELL Technologies). HESCs were passaged as previously described (see, e.g., Spence J R, et al., Nature. 2011 Feb. 3; 470(7332):105-9).
Differentiation of PSCs into Definitive Endoderm Differentiation into definitive endoderm was carried out as previously described (see, e.g., Spence J R, et al., Nature. 2011 Feb. 3; 470(7332):105-9; D'Amour K A; et al., Nat Biotechnol [Internet]. 2005 Oct. 28; 23(12):1534-41). Briefly, a 4-day Activin A (R&D systems) differentiation protocol was used. Cells were treated with Activin A (100 ng ml$^{-1}$) for three consecutive days in RPMI 1640 media (Life Technologies) with increasing concentrations of 0%, 0.2% and 2% HyClone defined fetal bovine serum (dFBS, Thermo Scientific).

Differentiation of Definitive Endoderm into Anterior Foregut

After differentiation into definitive endoderm, foregut endoderm was differentiated, essentially as described (see, e.g., Green M D, et al., Nat Biotechnol. Nature Publishing Group; 2011 Feb. 27; 1-7). Briefly, cells were incubated in foregut media: Advanced DMEM/F12 plus N-2 and B27 supplement, 10 mM Hepes, lx L-Glutamine (200 mM), lx Penicillin-streptomycin (5,000 U/mL, all from Life Technologies) with 200 ng/mL Noggin (NOG, R&D Systems) and 10 µM SB431542 (SB, Stemgent) for 4 days. For long term maintenance, cultures were maintain in "basal" foregut media without NOG and SB, or in the presence of growth factors including 50, 500 ng/mL FGF2 (R&D systems), 10 µM Sant-2 (Stemgent), 10 µM SU5402 (SU, Stemgent), 100 ng/mL SHH (R&D systems), and 1 µM SAG (Enzo Life Sciences) for 8 days.

Directed Differentiation into Anterior Foregut Spheroids and Lung Organoids

After differentiation into definitive endoderm, cells were incubated in foregut media with NOG, SB, 500 ng/mL FGF4 (R&D Systems), and 2 µM CHIR99021 (Chiron, Stemgent) for 4-6 days. After 4 days with treatment of growth factors, three-dimensional floating spheroids were present in the culture. Three-dimensional spheroids were transferred into Matrigel to support 3D growth as previously described (see, e.g., McCracken K W, et al., Nature Protocols; 2011 Nov. 10; 6(12):1920-8). Briefly, spheroids were embedded in a droplet of Matrigel (BD Bioscience #356237) in one well of a 24 well plate, and incubated at room temperature for 10 minutes. After the Matrigel solidified, foregut media with 1% Fetal bovine serum (FBS, CAT#: 16000-044, Life Technologies) or other growth factors and small molecules were overlaid and replaced every 4 days. Organoids were transferred into new Matrigel droplets every 10 to 15 days.

Immunohistochemistry

Immunostaining was carried out as previously described (64,84). Antibody information and dilutions can be found in FIG. 24. All images were taken on a Nikon A1 confocal microscope or an Olympus IX71 epifluorescent microscope.

RNA Extraction and qRT-PCR

RNA was extracted from monolayers, spheroids, and organoids using a MagMAX-96 Total RNA Isolation Kit (Life Technologies) and MAG Max Express (Applied Biosystems). RNA quantity and quality were determined spectrophotometrically, using a Nano Drop 2000 (Thermoscientific). Reverse transcription was conducted using the SuperScript VILO kit (Invitrogen), according to manufacturer's protocol. Finally, qRT-PCR was carried out using Quantitect Sybr Green MasterMix (Qiagen) on a Step One Plus Real-Time PCR system (Life Technologies). A list of primer sequences is provided in FIG. 25.

Seeding Lung Spheroids on Decellularized Human Lung Matrices

Human lungs deemed to be unsuitable for lung transplantation were obtained from beating-heart (or warm autopsy) donors through Gift of Life Michigan and lungs were decellularized as previously described (see, e.g., Booth A J, et al., American Journal of Respiratory and Critical Care Medicine. 2012 Nov. 1; 186(9):866-76). Slices were prepared using a sterile tissue punch (Fisher) and sterilized with 0.18% peracetic acid and 4.8% EtOH. Matrix slices were placed in a 96 well plate and approximately 50 NOG+SB+F+Ch+SAG spheres were pipetted directly onto the matrices. Samples were centrifuged for 2 min at 2000 rpm and then incubated at 37 C for 30 min without media. Foregut media supplemented with 1% FBS and 500 ng/mL FGF10 was then added to the matrices. Media was changed daily.

Transmission Electron Microscopy

D50 HLOs were processed as previously described (see, e.g., Rockich B E, et al., Proceedings of the National Academy of Sciences. 2013 Nov. 4; Prasov L, et al., Neuroreport. 2012 Jul. 11; 23(10):631-4). 70 nm sections were sections were imaged using a Philips CM-100 electron microscope.

Area and Cell Quantification

HLOs with P63+ cells were counted as having proximal airway-like epithelium and HLOs with SFTPC+ cells were counted as having distal airway-like epithelium. The area of proximal epithelium was determined by P63+ECAD+ staining. Area was measured using ImageJ software. Cell quantification of NKX2.1, P63, and DAPI was counted by Metamorph cell counting software. FOXJ1, SFTPC, and HOPX were counted in ImageJ using the cell counter plugin.

Statistical Analysis and Experimental Replicates

All immunofluorescence and qRT-PCR experiments were carried out at least two times with three (n=3) independent biological samples per experiment. The only exceptions to this were experiments that included human adult lung samples in the analysis. For these experiments, n=1 biological human lung sample was used in statistical replicates (triplicates) whereas all other samples used biological replicates (n=3). For quantification in FIG. 21, a total of 48 different HLOs (n=48) were counted for HLO composition. For the proximal epithelial area, 29 different HLOs were counted (n=29). For cell quantification, 15 different HLOs were counted (n=15). Statistical differences between groups were assessed with Prism software, using multiple t tests. All error bars represent SEM. Results were considered statistically significant at $P<0.05$.

RNA Sequencing and Analysis

Sequencing of HLOs (n=3 D65, n=3 D110) was performed by the University of Michigan DNA Sequencing Core, using the Illumina Hi-Seq platform. Sequencing of H9 Stem Cells (SC) and Definitive Endoderm (DE) was performed by the University of California, San Francisco DNA Sequencing Core using the Illumina Hi-Seq platform. All sequences were deposited in the EMBL-EBI ArrayExpress database using Annotare 2.0 and are catalogued under the accession number E-MTAB-3339 for the HLOs and E-MTAB-3158 for SC and DE. The University of Michigan Bioinformatics Core obtained the reads files and concatenated those into a single .fastq file for each sample. The Bioinformatics Core also downloaded reads files from EBI-AE database (Adult lung Samples) and NCBI-GEO (SRA) database (Fetal lung samples) (FIG. 22). The quality of the raw reads data for each sample was evaluated using FastQC (version 0.10.1) to identify features of the data that may indicate quality problems (e.g. low quality scores, over-represented sequences, inappropriate GC content, etc.). Initial QC report indicated over-representation of Illumina adapter sequences in samples from EBI-AE data set and NCBI-GEO data set. Adapter sequences were trimmed from the reads using Cutadapt (version 0.9.5) see, e.g., Chen C, et al., Source Code Biol Med. 2014; 9:8). Briefly, reads were aligned to the reference transcriptome (UCSC hg19) using TopHat (version 2.0.9) and Bowtie (version 2.1.0.0) see, e.g., Langmead B, et al., Genome Biol. 2009; 10(3):R25). Cufflinks/CuffNorm (version 2.2.1) were used for expression quantitation and differential expression analysis (see, e.g., Trapnell C, et al., Nature Protocols. 2012 March;

7(3):562-78), using UCSC hg19.fa as the reference genome sequence and UCSC hg19.gtf as the reference transcriptome annotation. For this analysis, parameter settings: "-multi-read-correct" were used to adjust expression calculations for reads that map in more than one locus, as well as "-compatible-hits-norm" and "-upper-quartile-norm" for normalization of expression values. Normalized FPKM tables were generated using the CuffNorm function found in Cufflinks. Transcriptional quantitation analysis in Cufflinks was conducted using the 64-bit Debian Linux stable version 7.8 ("Wheezy") platform. The complete FPKM matrix, containing frequency counts for all 24,010 genes contained in the reference genome for all 23 RNAseq samples, was evaluated using unscaled principle component analysis (PCA) to visualize and quantify multi-dimensional variation between samples (see, e.g., Ringnér M.; Nat Biotechnol. 2008 March; 26(3):303-4). Of the 24,010 genes annotated in the reference genome, 2,815 (11.7%) were not detected in the RNAseq analysis of any of the 23 samples. Principle components were calculated using the function 'prcomp' found in the R (version 3.1.2) statistical programming language (http://www.R-project.org/) and plotted using the R package 'ggplot2' (see, e.g., Wickham H.; ggplot2: Elegant Graphics for Data Analysis—Hadley Wickham—Google Books. 2009). Hierarchical cluster analysis based on the Canberra distance (see, e.g., Eisen, et al., PNAS Dec. 8, 1998 vol. 95 no. 25 14863-14868) between FPKM vectors was used to classify discrete RNAseq samples according to the degree of total transcriptional dissimilarity indicated by the normalized FPKM values. Bootstrap analysis was used to assess the uncertainty in the assigned hierarchical clustering relationships. 10,000 bootstraping iterations were generated by repeatedly randomly sampling the FPKM dataset. The bootstrap probability (BP) of a cluster is defined as the frequency of a given relationship among the bootstrap replicates. Multiscale bootstrap resampling was used to calculate an approximately unbiased (AU) p-value for a given relationship, with AU>95 indicating a high degree of statistical significance. Analyses were conducted using R package 'pvclust' (see, e.g., Suzuki R, et al., Bioinformatics. 2006 Jun. 15; 22(12):1540-2). Spearman correlation was applied as an additional assessment of the cumulative degree of correlation among RNAseq datasets. In addition, Spearman rank correlation coefficients (p) in a pairwise manner among all 23 RNAseq samples using the complete normalized FPKM data. The Spearman coefficients were plotted as a heatmap using the function 'heatmap.2' in the R package 'gplots' (http://CRAN.R-project.org/package=gplots). Complete data analysis scripts are available at https://github.com/hilldr/HLO_eLife2015.

Having now fully described the invention, it will be understood by those of skill in the art that the same can be performed within a wide and equivalent range of conditions, formulations, and other parameters without affecting the scope of the invention or any embodiment thereof. All patents, patent applications and publications cited herein are fully incorporated by reference herein in their entirety.

INCORPORATION BY REFERENCE

The entire disclosure of each of the patent documents and scientific articles referred to herein is incorporated by reference for all purposes.

EQUIVALENTS

The invention may be embodied in other specific forms without departing from the spirit or essential characteristics thereof. The foregoing embodiments are therefore to be considered in all respects illustrative rather than limiting the invention described herein. Scope of the invention is thus indicated by the appended claims rather than by the foregoing description, and all changes that come within the meaning and range of equivalency of the claims are intended to be embraced therein.

What is claimed is:

1. A method for obtaining lung organoid tissue, comprising:
   (a) culturing definitive endoderm cells in vitro and differentiating the definitive endoderm cells into tissue comprising ventral-anterior foregut spheroid tissue by activating a Wnt signaling pathway with CHIR99021 or Wnt, activating an FGF signaling pathway with FGF, inhibiting a BMP signaling pathway with Noggin, and inhibiting a TGFβ signaling pathway with SB431542,
   (b) culturing the obtained ventral-anterior foregut spheroid tissue in vitro and differentiating the obtained ventral-anterior foregut spheroid tissue into tissue comprising 3-dimensional lung tissue by activating a Hedgehog signaling pathway with smoothened agonist (SAG), and
   (c) culturing the obtained 3-dimensional lung tissue in vitro and differentiating the obtained tissue comprising 3-dimensional lung tissue into lung organoid tissue by activating the FGF signaling pathway with FGF 10 to obtain a lung organoid tissue.

2. The method of claim 1, wherein the definitive endoderm cells are derived from pluripotent stem cells, wherein the pluripotent stem cells are embryonic stem cells and/or induced pluripotent stem cells.

3. The method of claim 2, wherein the definitive endoderm cells are derived by contacting the pluripotent stem cell with Activin A.

4. The method of claim 1, wherein the obtained lung organoid tissue comprises one or more of upper airway-like epithelium with basal cells, immature ciliated cells surrounded by smooth muscle and myofibroblasts, and alveolar-like cells.

* * * * *